US010305040B2

(12) United States Patent
Stoessel et al.

(10) Patent No.: US 10,305,040 B2
(45) Date of Patent: May 28, 2019

(54) SPIRO DIHYDROACRIDINE DERIVATIVES AND THE USE THEREOF AS MATERIALS FOR ORGANIC ELECTROLUMINESCENCE DEVICES

(71) Applicant: Merck Patent GmbH, Darmstadt (DE)

(72) Inventors: Philipp Stoessel, Frankfurt am Main (DE); Elvira Montenegro, Weinheim (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 699 days.

(21) Appl. No.: 14/358,824

(22) PCT Filed: Oct. 18, 2012

(86) PCT No.: PCT/EP2012/004362
§ 371 (c)(1),
(2) Date: May 16, 2014

(87) PCT Pub. No.: WO2013/083216
PCT Pub. Date: Jun. 13, 2013

(65) Prior Publication Data
US 2014/0316134 A1 Oct. 23, 2014

(30) Foreign Application Priority Data
Nov. 17, 2011 (EP) .................... 11009127

(51) Int. Cl.
H01L 51/54 (2006.01)
C09K 11/06 (2006.01)
H01L 51/00 (2006.01)
C07D 221/20 (2006.01)
C07F 9/6568 (2006.01)
C07D 491/107 (2006.01)
C07D 491/20 (2006.01)
C07D 495/10 (2006.01)
C07D 519/00 (2006.01)
C07F 9/6561 (2006.01)
C07F 5/02 (2006.01)
H05B 33/10 (2006.01)
H01L 51/50 (2006.01)

(52) U.S. Cl.
CPC ........ H01L 51/0054 (2013.01); C07D 221/20 (2013.01); C07D 491/107 (2013.01); C07D 491/20 (2013.01); C07D 495/10 (2013.01); C07D 519/00 (2013.01); C07F 5/025 (2013.01); C07F 9/6561 (2013.01); C07F 9/65683 (2013.01); C07F 9/65685 (2013.01); C09K 11/06 (2013.01); H01L 51/005 (2013.01); H01L 51/0052 (2013.01); H01L 51/0056 (2013.01); H01L 51/0061 (2013.01); H01L 51/0067 (2013.01); H01L 51/0071 (2013.01); H01L 51/0072 (2013.01); H01L 51/0073 (2013.01); H05B 33/10 (2013.01); C09K 2211/1007 (2013.01); C09K 2211/1011 (2013.01); C09K 2211/1014 (2013.01); C09K 2211/1029 (2013.01); C09K 2211/1044 (2013.01); C09K 2211/1059 (2013.01); C09K 2211/1088 (2013.01); C09K 2211/1092 (2013.01); H01L 51/5012 (2013.01); H01L 51/5016 (2013.01); Y02E 10/549 (2013.01)

(58) Field of Classification Search
CPC ...... Y02E 10/549; C07F 5/025; C07F 9/6565; C07F 9/65683; C07F 9/65685; C07D 221/20; C07D 491/00; C07D 491/10; C07D 491/107; C07D 491/20; C07D 495/00; C07D 495/10; C07D 519/00; C09K 11/06; C09K 2211/00; C09K 2211/1007; C09K 2211/1011; C09K 2211/1014; C09K 2211/1029; C09K 2211/1044; C09K 2211/1059; C09K 2211/1088; C09K 2211/1092; H01L 51/0032; H01L 51/005; H01L 51/0054; H01L 51/0052; H01L 51/0056; H01L 51/0062; H01L 51/0061; H01L 51/0067; H01L 51/0071; H01L 51/0072; H01L 51/0073; H01L 51/50; H01L 51/5012; H01L 51/5016
USPC ............. 257/40, 88–104, E51.001–E51.052; 252/301.16–301.35; 544/180, 230; 546/18; 428/690, 691, 917, 411.4, 336; 427/58, 66; 313/500–512
See application file for complete search history.

(56) References Cited

U.S. PATENT DOCUMENTS

| 2004/0109951 | A1* | 6/2004 | Irvin | ...................... C09K 11/02 428/690 |
|---|---|---|---|---|
| 2008/0024054 | A1 | 1/2008 | Itoh et al. | |
| 2008/0193797 | A1* | 8/2008 | Heil | ........................ C07C 13/62 428/690 |
| 2010/0019658 | A1 | 1/2010 | Lin et al. | |
| 2010/0219406 | A1* | 9/2010 | Kahle | .................. H01L 51/0061 257/40 |

(Continued)

FOREIGN PATENT DOCUMENTS

| CN | 1338499 A | 3/2002 |
|---|---|---|
| CN | 101659638 A | 3/2010 |

(Continued)

OTHER PUBLICATIONS

International Search Report for PCT/EP2012/004362 dated Mar. 25, 2013.

Primary Examiner — Andrew K Bohaty
(74) Attorney, Agent, or Firm — Drinker Biddle & Reath LLP

(57) ABSTRACT

The present invention relates to compounds of formulae (1), (2) or (3) that are suitable for use in electronic devices, and to electronic device, in particular organic electroluminescence devices, containing these compounds.

18 Claims, No Drawings

(56) References Cited

U.S. PATENT DOCUMENTS

| | | |
|---|---|---|
| 2011/0272684 A1 | 11/2011 | Parham et al. |
| 2012/0223276 A1 | 9/2012 | Parham et al. |
| 2014/0091265 A1 | 4/2014 | Stoessel et al. |
| 2014/0138670 A1 | 5/2014 | Nakagawa et al. |

FOREIGN PATENT DOCUMENTS

| | | |
|---|---|---|
| JP | 2002265938 A | 9/2002 |
| JP | 2008511970 A | 4/2008 |
| JP | 2000344761 A | 12/2012 |
| JP | 2014520096 A | 8/2014 |
| KR | 20110110508 A | 10/2011 |
| KR | 20110111093 A | 10/2011 |
| KR | 20110113469 A | 10/2011 |
| KR | 20110120075 A | 11/2011 |
| WO | WO-2010083872 A2 | 7/2010 |
| WO | WO-2011057706 A2 | 5/2011 |
| WO | WO-2013011954 A1 | 1/2013 |

\* cited by examiner

SPIRO DIHYDROACRIDINE DERIVATIVES AND THE USE THEREOF AS MATERIALS FOR ORGANIC ELECTROLUMINESCENCE DEVICES

CROSS-REFERENCE TO RELATED APPLICATIONS

This application is a national stage application (under 35 U.S.C. § 371) of PCT/EP2012/004362, filed Oct. 18, 2012, which claims benefit of European Application No. 11009127.9, filed Nov. 17, 2011, both of which are incorporated herein by reference in their entirely.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold energy and power efficiency is possible using organometallic compounds as phosphorescence emitters. In general, however, there is still a need for improvement, for example with respect to efficiency, operating voltage and lifetime, in the case of OLEDs, in particular also in the case of OLEDs which exhibit triplet emission (phosphorescence). In addition, it is desirable that the materials used can be synthesised in high yield and purity.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. For fluorescent OLEDs too, there is still a need for improvement in these materials and for emitters and matrix materials.

In accordance with the prior art, use is made, inter alia, of carbazole derivatives, for example in accordance with WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, or dihydroacridine derivatives, for example in accordance with US 2010/0019658, as matrix materials for phosphorescent emitters in organic electroluminescent devices. Further improvements are desirable here, likewise in relation to the efficiency, the lifetime and the thermal stability of the materials.

The object of the present invention is the provision of compounds which are suitable for use in a fluorescent or phosphorescent OLED, in particular as matrix material or as hole-transport/electron-blocking material or exciton-blocking material, but also as hole-blocking material, matrix for fluorescent emitters or as fluorescent emitter. It is a further object of the present invention to provide further organic semiconductors for organic electroluminescent devices in order to facilitate a greater choice in the production of OLEDs for the person skilled in the art.

Surprisingly, it has been found that certain compounds, described in greater detail below, achieve this object and result in improvements in the organic electroluminescent device. The improvements here relate, in particular, to the lifetime, the efficiency and/or the operating voltage. The present invention therefore relates to these compounds and to electronic devices, in particular organic electroluminescent devices, which comprise compounds of this type.

The present invention relates to a compound of the formula (1), (2) or (3)

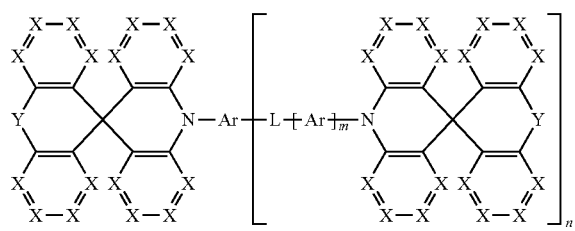

formula (1)

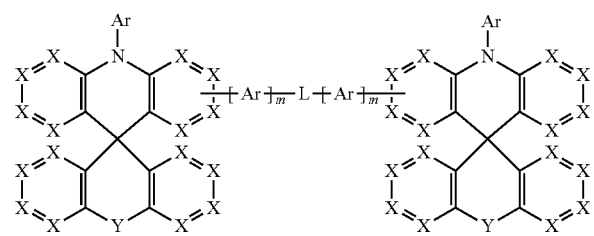

formula (2)

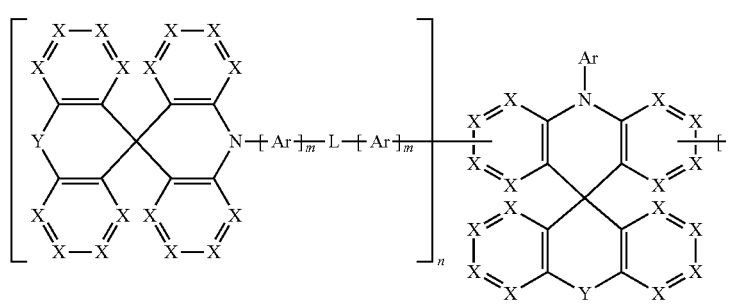

formula (3)

where the following applies to the symbols and indices used:

Y is on each occurrence, identically or differently, O, S, Se, BR$^1$, C(R$^1$)$_2$, Si(R$^1$)$_2$, PR$^1$, P(=O)R$^1$, C(R$^1$)$_2$—C(R$^1$)$_2$, CR$^1$=CR$^1$ or a benzene group which is linked via the ortho-positions and which may be substituted by one or more radicals R$^1$;

X is on each occurrence, identically or differently, CR$^2$ or N; or two adjacent X stand for S, O or NR$^2$, so that a five-membered ring arises; or two adjacent X stand for a group of the following formula (4) or (5),

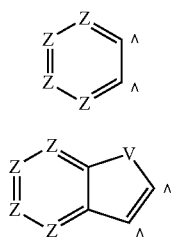

formula (4)

formula (5)

where ^ indicates the corresponding adjacent groups X in the formula (1), (2) or (3);

X here stands for C if a group Ar or L is bonded to this group X in formula (2) or (3);

V is on each occurrence, identically or differently, C(R$^2$)$_2$, NR$^2$, O or S;

Z is on each occurrence, identically or differently, CR$^2$ or N;

Ar is on each occurrence, identically or differently, an aromatic or heteroaromatic ring system having 5 to 40 aromatic ring atoms, which may be substituted by one or more radicals R$^3$; the group Ar and the adjacent group X, which in this case stands for C, may also be bridged to one another here by a single bond or a divalent group selected from C(R$^3$)$_2$, NR$^3$, O or S;

L is on each occurrence, identically or differently, a single bond or a divalent group;

R$^1$, R$^2$, R$^3$ is selected on each occurrence, identically or differently, from the group consisting of H, D, F, Cl, Br, I, CN, NO$_2$, N(Ar$^1$)$_2$, N(R$^4$)$_2$, C(=O)Ar$^1$, C(=O)R$^4$, P(=O)(Ar$^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^4$, where one or more non-adjacent CH$_2$ groups may be replaced by R$^4$C=CR$^4$, C≡C, Si(R$^4$)$_2$, C=O, C=S, C=NR$^4$, P(=O)(R$^4$), SO, SO$_2$, NR$^4$, O, S or CONR$^4$ and where one or more H atoms may be replaced by D, F, Cl, Br, I, CN or NO$_2$, an aromatic or heteroaromatic ring system having 5 to 60, aromatic ring atoms, which may in each case be substituted by one or more radicals R$^4$, an aryloxy or heteroaryloxy group having 5 to 60 aromatic ring atoms, which may be substituted by one or more radicals R$^4$, where two or more adjacent substituents R$^1$ or R$^3$ may optionally form a monocyclic or polycyclic, aliphatic ring system or R$^2$ may form a monocyclic or polycyclic, aliphatic, aromatic or heteroaromatic ring system, which may be substituted by one or more radicals R$^4$;

R$^4$ is selected on each occurrence, identically or differently, from the group consisting of H, D, F, Cl, Br, I, CN, NO$_2$, N(Ar$^1$)$_2$, N(R$^5$)$_2$, C(=O)Ar$^1$, C(=O)R$^5$, P(=O)(Ar$^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^5$, where one or more non-adjacent CH$_2$ groups may be replaced by R$^5$C=CR$^5$, C≡C, Si(R$^5$)$_2$, C=O, C=S, C=NR$^5$, P(=O)(R$^5$), SO, SO$_2$, NR$^5$, O, S or CONR$^5$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^5$, an aryloxy or heteroaryloxy group having 5 to 60 aromatic ring atoms, which may be substituted by one or more radicals R$^5$, or a combination of these systems, where two or more adjacent substituents R$^4$ may optionally form a monocyclic or polycyclic, aliphatic ring system, which may be substituted by one or more radicals R$^5$;

Ar$^1$ is on each occurrence, identically or differently, an aromatic or heteroaromatic ring system having 5-30 aromatic ring atoms, which may be substituted by one or more non-aromatic radicals R$^5$; two radicals Ar$^1$ which are bonded to the same N atom or P atom may also be bridged to one another here by a single bond or a bridge selected from N(R$^5$), C(R$^5$)$_2$, O or S;

R$^5$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^5$ may form a mono- or polycyclic, aliphatic ring system with one another;

m is on each occurrence, identically or differently, 0 or 1;

n is 0, 1, 2, 3, 4 or 5;

p is 0 or 1.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (annellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the groups mentioned above, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the groups mentioned above; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the radicals $R^2$ mentioned above or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

As described above, the group Ar and an adjacent group X may also be bridged to one another. An "adjacent group X" here is taken to mean a group X which is separated from the group Ar by a nitrogen atom and a carbon atom, as depicted diagrammatically below, where this group X stands for C if this X and the group Ar are bridged:

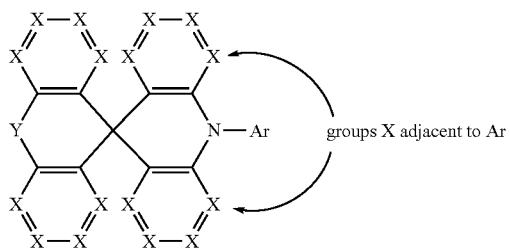

groups X adjacent to Ar

The ring formation is depicted below by way of example for compounds of the formula (1) where n=0, where the ring formation can take place entirely analogously to the other compounds according to the invention:

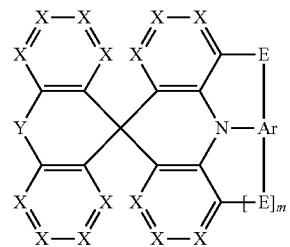

where E stands for a single bond, $C(R^3)_2$, $NR^3$, O or S and the other symbols and indices used have the meanings given above.

In a preferred embodiment of the invention, Y stands, identically or differently on each occurrence, for O or $C(R^1)_2$, particularly preferably for O.

Furthermore preferably, all groups Y are selected identically.

In a further preferred embodiment of the invention, X stands, identically or differently on each occurrence, for $CR^2$ or N, where a maximum of one group X per ring stands for N; or two adjacent groups X stand for a group of the formula (4) or (5), in particular formula (5), where Z stands, identically or differently on each occurrence, for $CR^2$ and V stands, identically or differently on each occurrence, for $NR^2$ or $C(R^2)_2$.

X particularly preferably stands, identically or differently on each occurrence, for $CR^2$.

Preference is furthermore given to compounds of the formula (1) mentioned above and the following compounds (2a) or (3a),

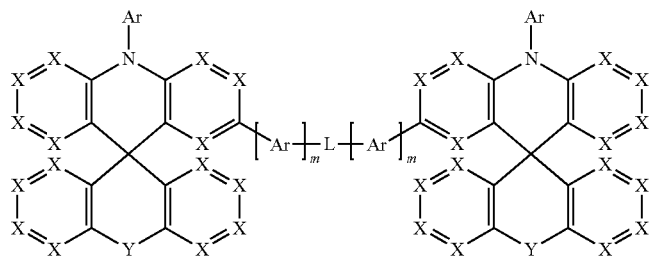

formula (2a)

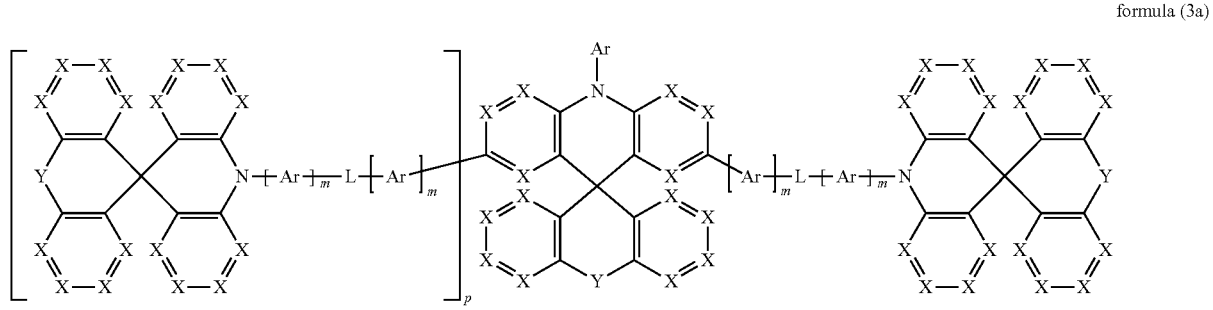

formula (3a)

Particular preference is given to compounds of the formula (1 mentioned above), in particular where n=0.

In a preferred embodiment of the invention, the group L stands, identically or differently on each occurrence, for a straight-chain alkylene, alkylidene, alkyleneoxy or thioalkyleneoxy group having 1 to 10 C atoms or a branched or cyclic alkylene, alkylidene, alkyleneoxy or thioalkyleneoxy group having 3 to 40 C atoms or an alkenylene or alkynylene group having 2 to 40 C atoms, which may be substituted by in each case one or more radicals $R^4$, where one or more non-adjacent $CH_2$ groups may be replaced by —$R^4C$=$CR^4$—, —C≡C—, $Si(R^4)_2$, C=O, C=$NR^4$, P(=O)$R^4$, S=O, $SO_2$, —O—, —S— or —$CONR^4$— and where one or more H atoms may be replaced by D, F, Cl, Br, I, CN or $NO_2$, or $P(R^4)$, $P(=O)(R^4)$, $N(Ar^1)$; or L is a single bond.

In a particularly preferred embodiment of the invention, the group L stands for a single bond.

Preferred embodiments of the compounds of the formula (1), (2) and (3) are the compounds of the following formulae (6), (7) and (8),

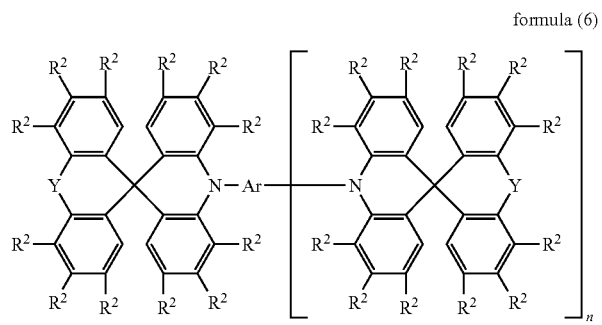

formula (6)

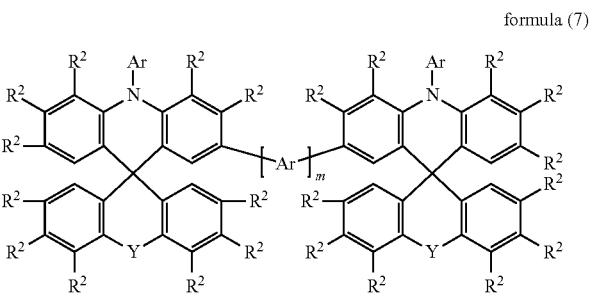

formula (7)

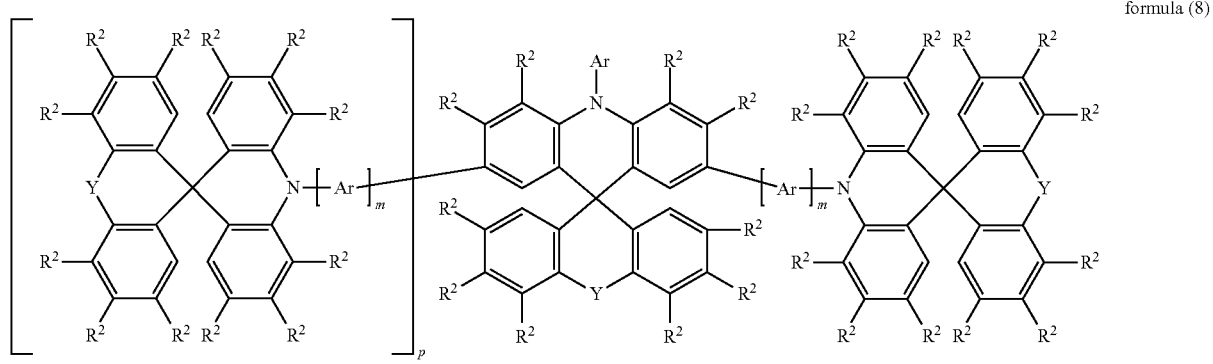

formula (8)

where the symbols and indices used have the meanings given above and Y preferably stands for O.

Furthermore, groups of the formula (4) or (5) may be condensed on, as depicted below by way of example by the formulae (9), (10), (11) and (12) with condensed-on groups of the formula (5), formula (9)

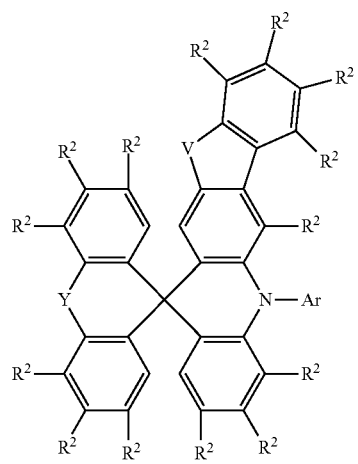

formula (10)

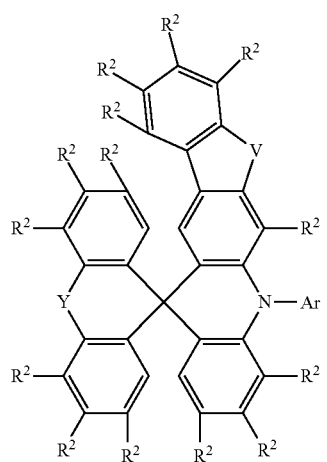

formula (11)

formula (12)

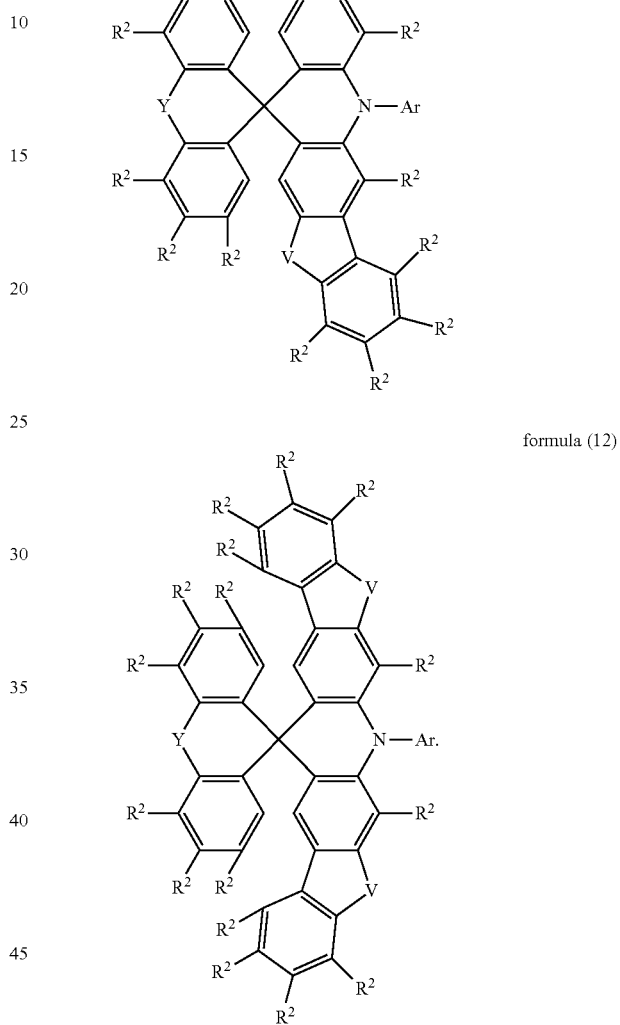

Particular preference is given to the compounds of the following formulae (6a) to (12a).

formula (6a)

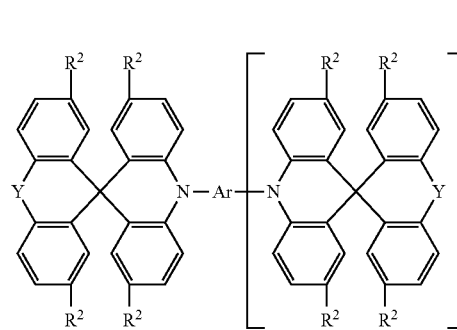

formula (7a)

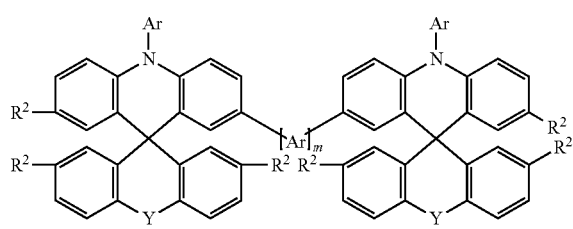

formula (8a)
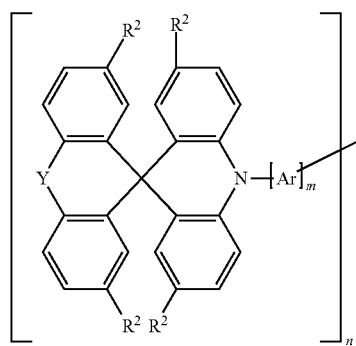
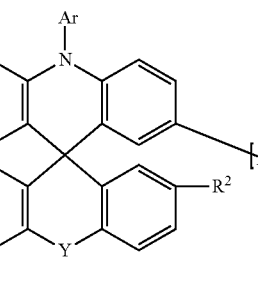
where the symbols and indices used have the meanings given above and Y preferably stands for O.
formula (9a)
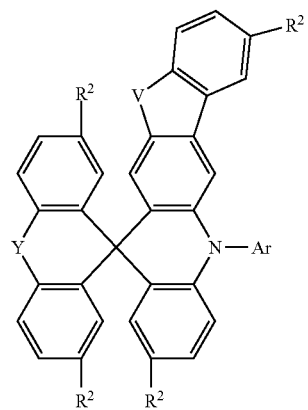
formula (10a)
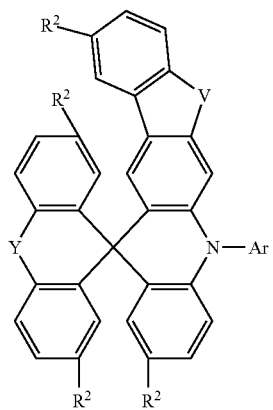
formula (11a)
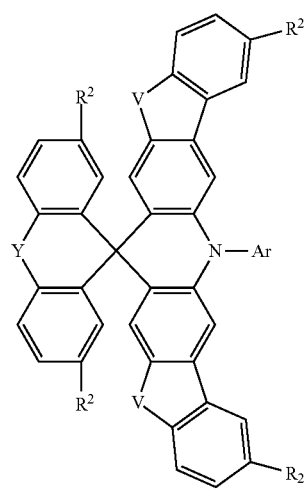
formula (12a)
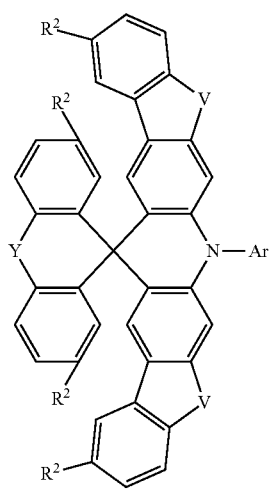
Very particular preference is given to the compounds of the following formulae (6b) to (12b).

formula (6b)
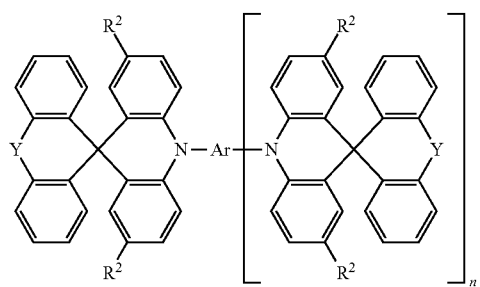
formula (7b)
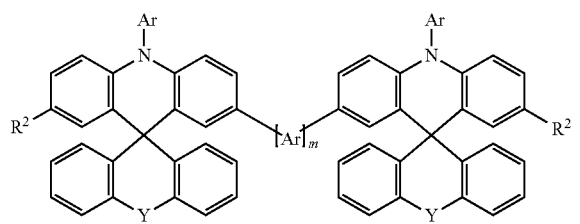
formula (8b)
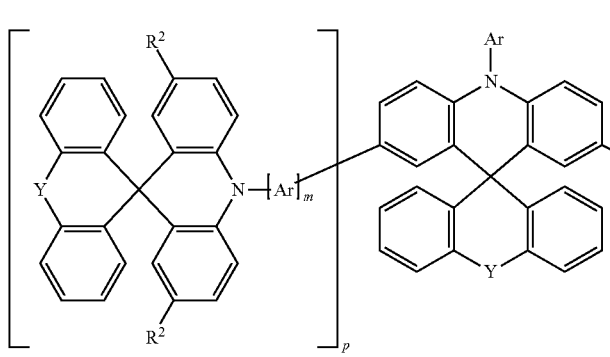
formula (9b)
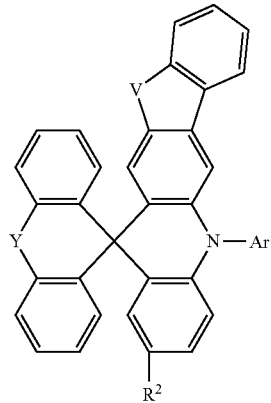
formula (10b)
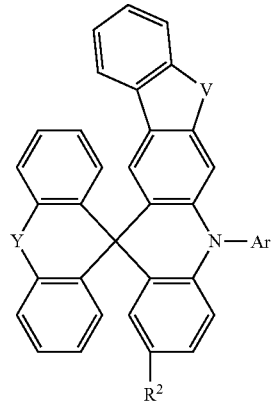
formula (11b)
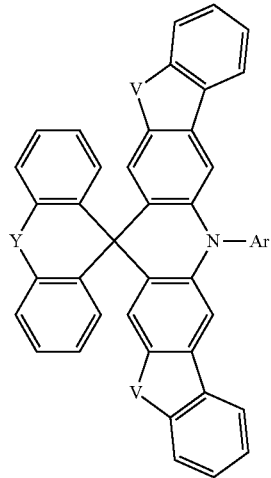
formula (12b)
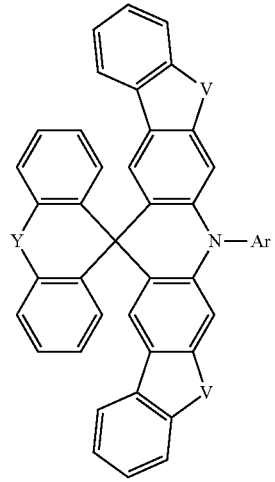

where the symbols and indices used have the meanings given above and Y preferably stands for O.

Particular preference is given to the compounds of the formula (6b) in which the index n=0 or 1.

In a preferred embodiment of the invention, $R^1$, $R^2$ and $R^3$ in the formulae mentioned above are selected, identically or differently on each occurrence, from the group consisting of H, D, F, Cl, Br, CN, $N(Ar^1)_2$, $C(=O)Ar^1$, a straight-chain alkyl or alkoxy group having 1 to 10 C atoms, a branched or cyclic alkyl or alkoxy group having 3 to 10 C atoms, an alkenyl or alkynyl group having 2 to 10 C atoms, each of which may be substituted by one or more radicals $R^4$, where one or more non-adjacent $CH_2$ groups may be replaced by O and where one or more H atoms may be replaced by D or F, and an aromatic or heteroaromatic ring system having 5 to 30 aromatic ring atoms, which may in each case be substituted by one or more radicals $R^4$.

In a particularly preferred embodiment of the invention, $R^1$, $R^2$ and $R^3$ in the formulae mentioned above are selected, identically or differently on each occurrence, from the group consisting of H, D, F, Cl, Br, CN, a straight-chain alkyl group having 1 to 5 C atoms, a branched or cyclic alkyl group having 3 to 10 C atoms, where one or more H atoms may be replaced by D or F, and an aromatic or heteroaromatic ring system having 5 to 18 aromatic ring atoms, which may in each case be substituted by one or more radicals $R^4$.

$R^2$ preferably does not encompass a heteroaryl group having 5 ring atoms, an alkenyl group or an alkynyl group.

$R^2$ is preferably selected, identically or differently on each occurrence, from the group consisting of H, D, F, Cl, Br, CN, a straight-chain alkyl group having 1 to 5 C atoms, a branched or cyclic alkyl group having 3 to 10 C atoms, where one or more H atoms may be replaced by D or F, and an aromatic ring system having 5 to 18 aromatic ring atoms, which may in each case be substituted by one or more radicals $R^4$, where $R^4$ is selected on each occurrence, identically or differently, from the group consisting of H, D, F, Cl, Br, I, CN, $NO_2$, $N(Ar^1)_2$, $N(R^5)_2$, $C(=O)Ar^1$, $C(=O)R^5$, $P(=O)(Ar^1)_2$, a straight-chain alkyl, alkoxy or thioalkyl group having 1 to 5 C atoms, a branched or cyclic alkyl, alkoxy or thioalkyl group having 3 to 10 C atoms, where one or more H atoms may be replaced by D, F, Cl, Br or CN, and an aromatic or heteroaromatic ring system having 5 to 18 aromatic ring atoms, which may in each case be substituted by one or more radicals $R^5$.

For compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups, in particular branched alkyl groups, having up to 10 C atoms or which are substituted by oligoarylene groups, for example ortho-, meta-, para- or branched terphenyl or quaterphenyl groups.

Preferred groups Ar are selected from aromatic or heteroaromatic ring systems having 5 to 24 aromatic ring atoms, which may in each case be substituted by one or more radicals $R^3$. Particularly preferred groups Ar are selected from benzene, ortho-, meta- or para-biphenyl, ortho-, meta-, para- or branched terphenyl, ortho-, meta- para- or branched quaterphenyl, 1- or 2-naphthyl, pyrrole, furan, thiophene, indole, benzothiophene, benzothiophene, carbazole, dibenzofuran, dibenzothiophene, pyridine, pyrimidine, pyrazine, pyridazine, triazine, anthracene, phenanthrene, pyrene, benzanthracene or combinations of two or three of these groups, each of which may be substituted by one or more radicals $R^3$.

If $R^1$, $R^2$ and $R^3$ stand for an aromatic or heteroaromatic ring system, this is preferably selected, identically or differently on each occurrence, from the same groups as indicated above as preferred groups for Ar. If Y stands for $BR^1$, $R^1$ then preferably stands for an aryl or heteroaryl group which is substituted in at least one ortho-position and preferably in both ortho-positions, for example for a xylyl or mesityl group.

If the compounds of the formula (1), (2) or (3) or the preferred embodiments are used as electron-transport material, it is preferred for the group Y to stand for $BR^1$ or $P(=O)(R^1)$ and/or for at least one of the radicals $R^1$, $R^2$ and/or Ar to stand for an electron-deficient heteroaromatic ring system. In accordance with the invention, electron-deficient heteroaromatic rings are five-membered heteroaromatic rings having at least two heteroatoms or six-membered heteroaromatic rings, onto which in each case one or more aromatic or heteroaromatic groups may also be condensed, for example substituted or unsubstituted imidazoles, pyrazoles, thiazoles, oxazoles, oxadiazoles, triazoles, pyridines, pyrazines, pyrimidines, pyridazines, triazines, benzimidazoles, etc., in particular those as shown below.

If the compound according to the invention is employed as matrix material for a phosphorescent emitter or as electron-transport material, it is preferred for at least one substituent $R^1$, $R^2$ and/or $R^3$ or a monovalent group Ar to be an electron-deficient group, in particular selected from structures of the following formulae (13) to (16) for $R^1$ to $R^3$ or the formulae (13), (15) or (16) for Ar,

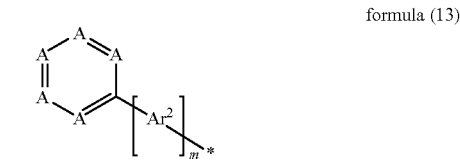

formula (13)

formula (14)

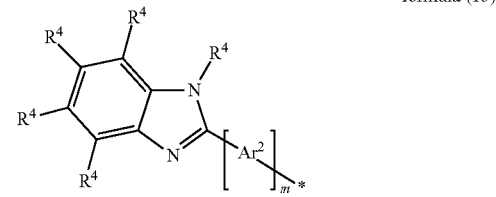

formula (15)

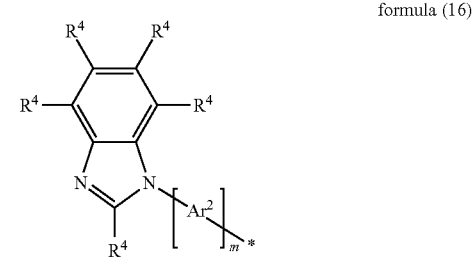

formula (16)

and/or at least one divalent or trivalent group Ar preferably stands for a group of the following formulae (17) to (19),

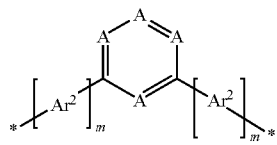
formula (17)

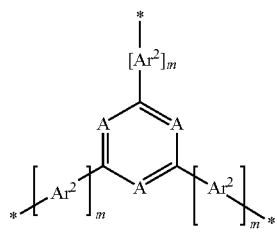
formula (18)

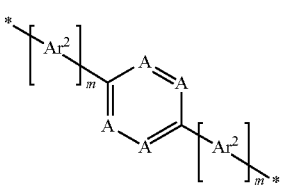
formula (19)

where $R^3$, $R^4$ and m have the meaning given above, * indicates the position of the bonding of the group of the formula (13) to (19) and furthermore:

A is on each occurrence, identically or differently, $CR^4$ or N, with the proviso that one, two or three groups A stand for N;

$Ar^2$ is, identically or differently on each occurrence, a divalent aromatic or heteroaromatic ring system having 5 to 16 C atoms, which may be substituted by one or more radicals $R^4$;

where $R^4$ is to be replaced by $R^3$ if the groups of the formulae (13), (15) and (16) stand for Ar and in the cases of the formulae (17) to (19).

In a particularly preferred embodiment of the invention, at least one substituent $R^1$, $R^2$, $R^3$ or Ar stands for a group of the formula (13) mentioned above, and/or at least one group Ar stands for a group of the formulae (17) to (19) mentioned above, where in each case two or three symbols A stand for N and the other symbols A stand for $CR^4$, where $R^3$ is to be replaced by $R^4$ if the groups of the formulae (13), (15) and (16) stand for Ar and in the cases of the formulae (17) to (19).

Particularly preferred groups $R^1$, $R^2$, $R^3$ or Ar are therefore the groups of the following formulae (20) to (26), and particularly preferred groups Ar are the groups of the following formulae (27) to (34),

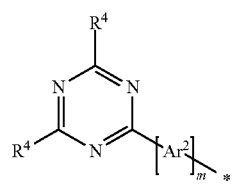
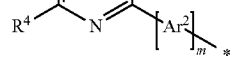
formula (20)

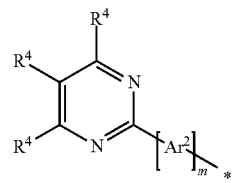
formula (21)

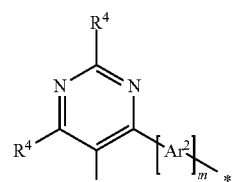
formula (22)

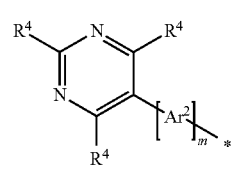
formula (23)

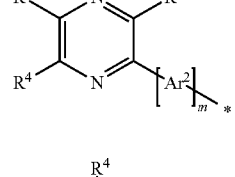
formula (24)

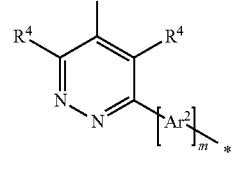
formula (25)

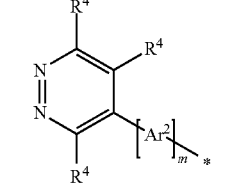
formula (26)

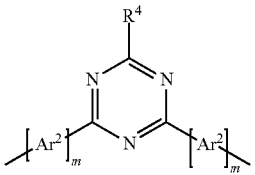
formula (27)

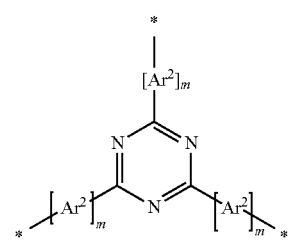
formula (28)

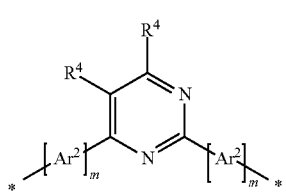
formula (29)

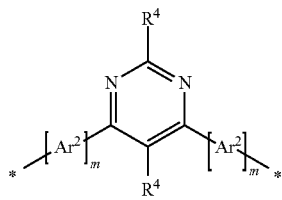
formula (30)

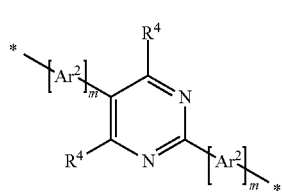
formula (31)

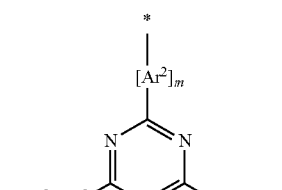
formula (32)

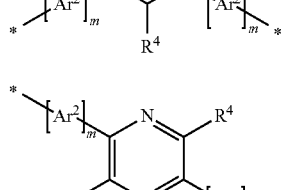
formula (33)

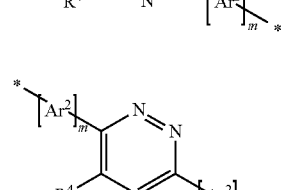
formula (34)

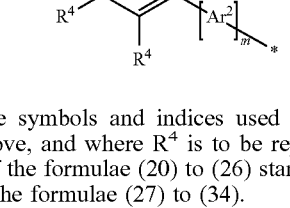

where the symbols and indices used have the meanings given above, and where $R^4$ is to be replaced by $R^3$ if the groups of the formulae (20) to (26) stand for Ar and in the cases of the formulae (27) to (34).

If $R^1$, $R^2$, $R^3$ or Ar stands for a group of the formula (20), $R^3$ or $R^4$ in this group then preferably stands for an aromatic or heteroaromatic ring system having 5 to 24 aromatic ring atoms, which may be substituted by one or more radicals $R^5$, in particular for phenyl, ortho-, meta- or para-biphenyl, ortho-, meta-, para- or branched terphenyl or ortho-, meta-, para- or branched quaterphenyl.

If $R^1$, $R^2$, $R^3$ or Ar stands for a group of the formula (21) to (26), $R^3$ or $R^4$ in these groups then preferably stands, identically or differently on each occurrence, for H, D or an aromatic or heteroaromatic ring system having 5 to 24 aromatic ring atoms, which may be substituted by one or more radicals $R^5$, in particular for H or phenyl, ortho-, meta- or para-biphenyl, ortho-, meta-, para- or branched terphenyl or ortho-, meta-, para- or branched quaterphenyl.

If Ar stands for a group of the formula (27) to (34), $R^3$ in these groups then preferably stands, identically or differently on each occurrence, for H, D or an aromatic or heteroaromatic ring system having 5 to 24 aromatic ring atoms, which may be substituted by one or more radicals $R^5$, in particular for H or phenyl, ortho-, meta- or para-biphenyl, ortho-, meta-, para- or branched terphenyl or ortho-, meta-, para- or branched quaterphenyl.

If the compound according to the invention is employed as matrix material for a phosphorescent emitter, as hole-transport material or as electron- or exciton-blocking material, at least one substituent $R^1$, $R^2$, $R^3$ or Ar is preferably selected from the group consisting of triarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals $R^3$ or $R^4$, or at least one substituent $R^1$, $R^2$ or $R^3$ stands for —NAr$_2$. These groups are preferably selected from the groups of the following formulae (35) to (49),

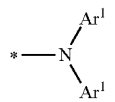
formula (35)

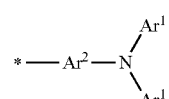
formula (36)

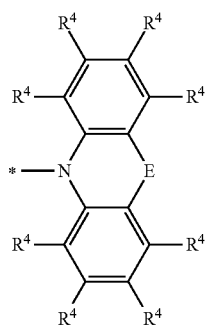
formula (37)

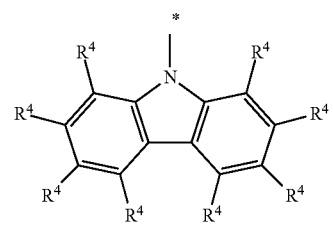
formula (38)

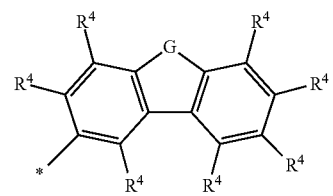
formula (39)

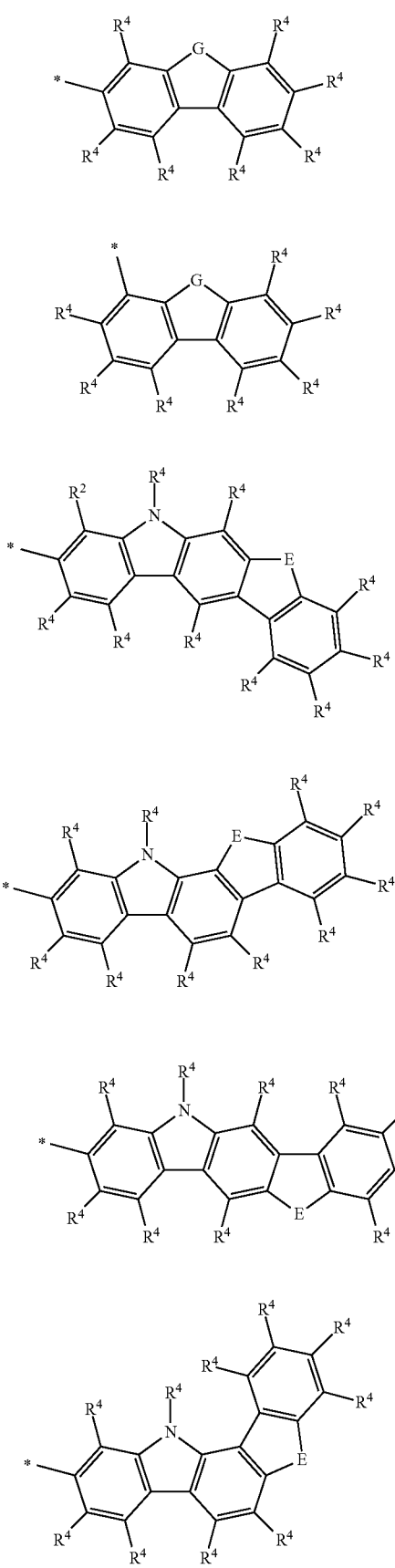

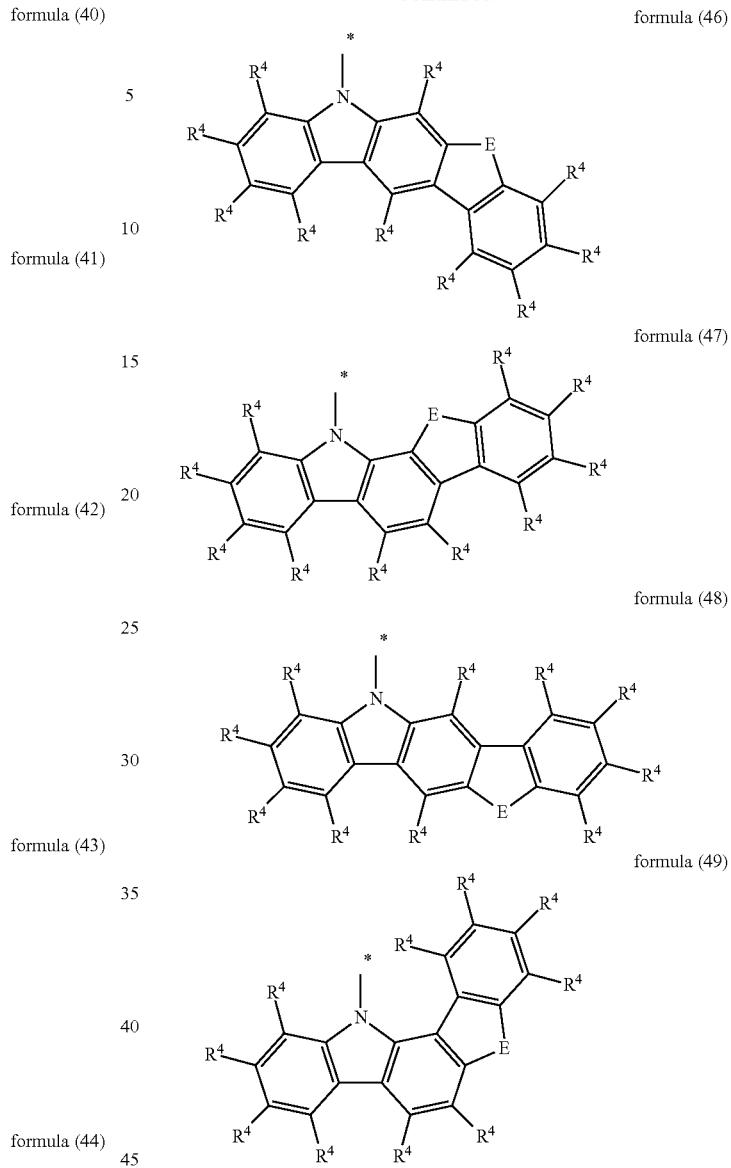

where the symbols used have the meanings given above and furthermore:

E is selected from the group consisting of $C(R^4)_2$, $NR^4$, O or S;

G is selected from the group consisting of $NR^4$, O or S, and $R^4$ is to be replaced by $R^3$ if the groups of the formulae (35) to (49) stand for Ar.

In a further preferred embodiment of the invention, the symbols $R^1$, $R^2$ and $R^3$ which do not stand for a group of the formulae (13) to (49) mentioned above in the compounds according to the invention stand for H or D.

The preferred embodiments mentioned above can be combined with one another as desired. In a particularly preferred embodiment of the invention, the preferences mentioned above occur simultaneously.

If the compounds of the formula (1), (2) or (3) or the preferred embodiments are used as matrix material for a phosphorescent emitter, it is preferred for the compound to contain no condensed aryl or heteroaryl groups in which more than two six-membered rings are condensed directly onto one another. In particular, it is preferred for the radicals $R^1$, $R^2$, $R^3$ and Ar to contain no condensed aryl or heteroaryl group in which two or more six-membered rings are condensed directly onto one another, and for two adjacent groups X not to stand for a group of the formula (4). The compound of the formula (1), (2) or (3) particularly preferably contains absolutely no condensed aryl or heteroaryl groups in which six-membered rings are condensed directly onto one another.

If the compounds of the formula (1), (2) or (3) or the preferred embodiments are used as matrix material for a fluorescent emitter or as fluorescent emitter, it is preferred for at least one of the radicals $R^1$, $R^2$ and/or $R^3$ to contain a group which is selected from naphthalene, anthracene, phenanthrene, pyrene and/or benzanthracene, each of which may also be substituted by the groups mentioned above, and/or for two adjacent groups X at least on one of the aromatic rings to stand for a group of the formula (4).

If the compounds of the formula (1), (2) or (3) or the preferred embodiments are employed as hole-transport material in a hole-transporting, hole-injecting or another layer, it is preferred for at least one of the radicals $R^1$, $R^2$ and/or $R^3$ to contain a group which is selected from aromatic ring systems having 6 to 24 aromatic ring atoms. In this case, it is furthermore preferred for Y to be selected on each occurrence, identically or differently, from O, S and $C(R^1)_2$, and particularly preferably to be O.

Examples of preferred compounds of the embodiments mentioned above are the compounds of the following structures.

1

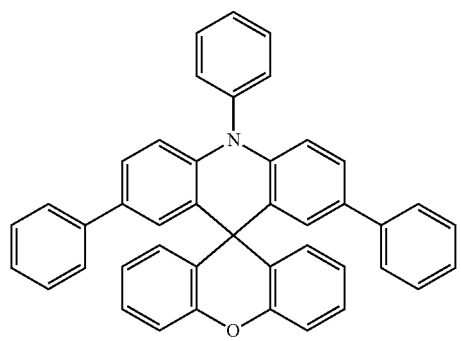

2

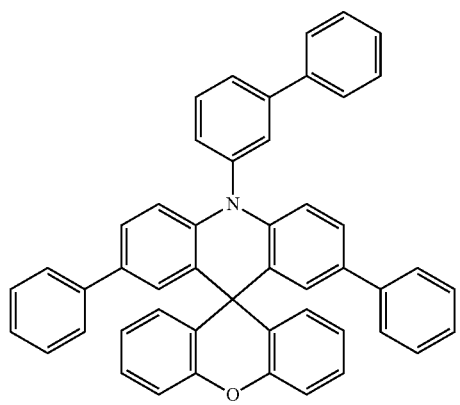

3

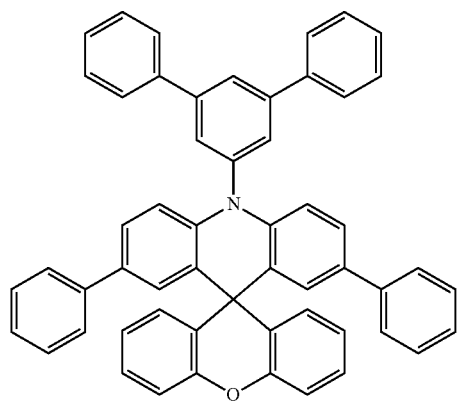

4

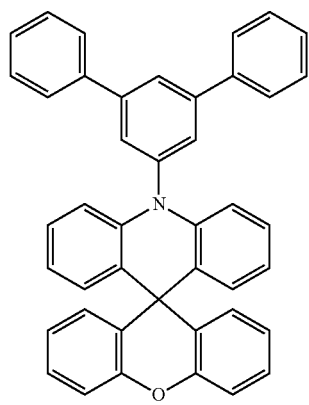

5

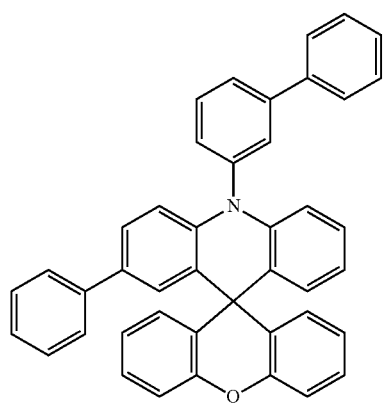

6

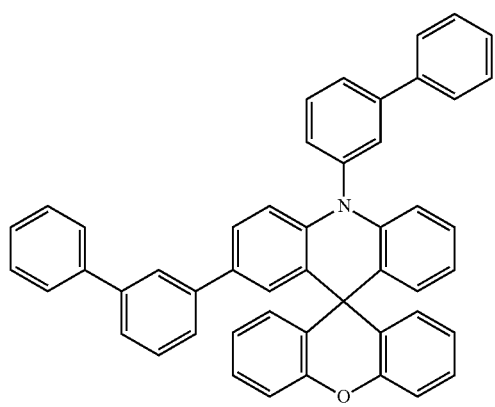

-continued
7
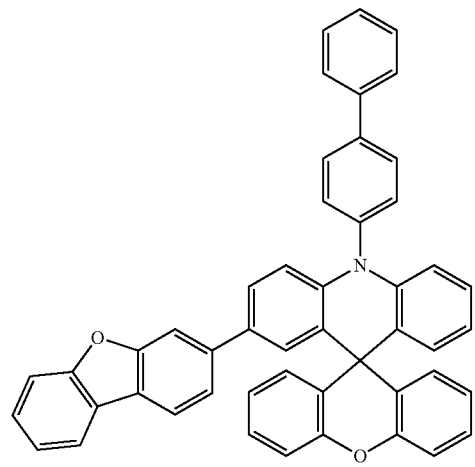
8
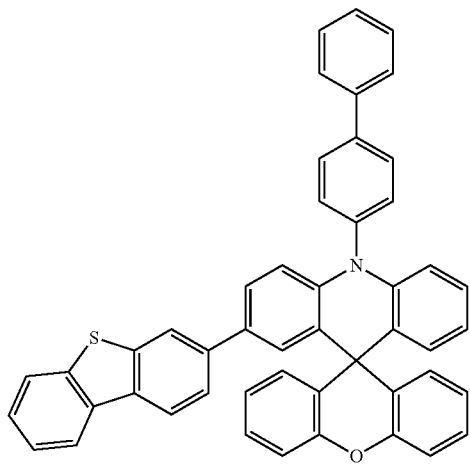
9
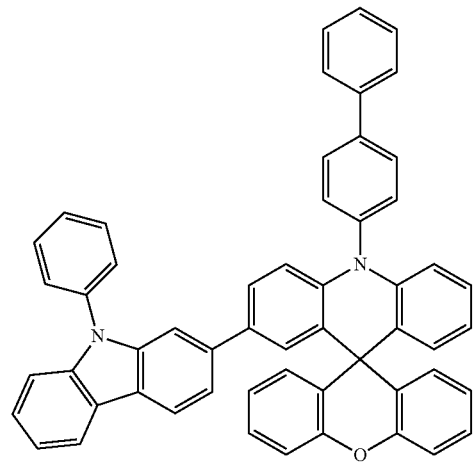
10
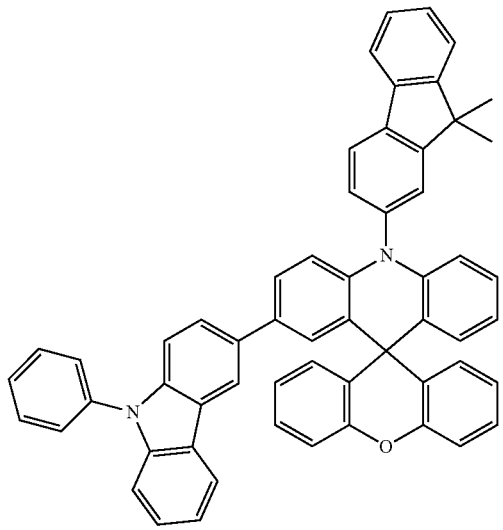
11
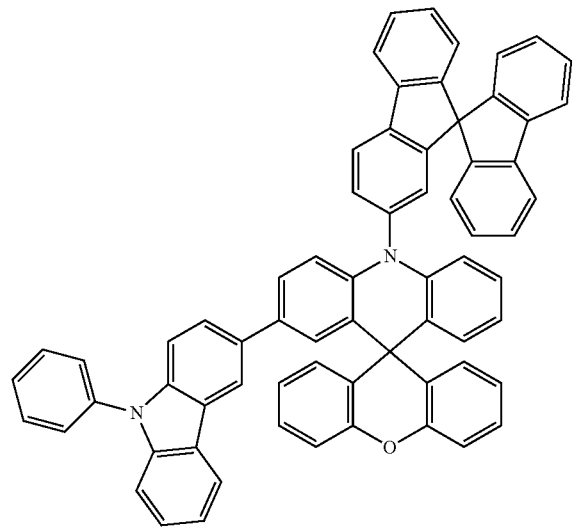
12
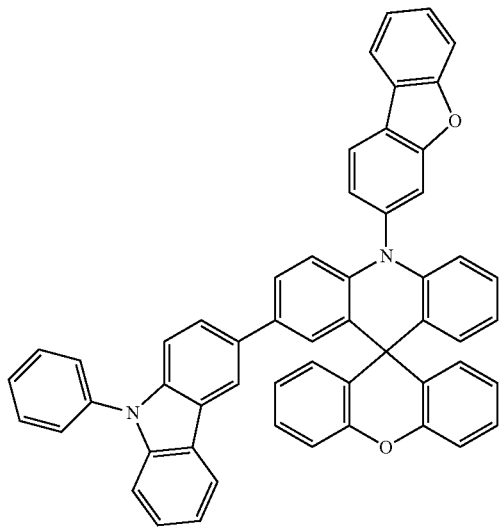

-continued
13
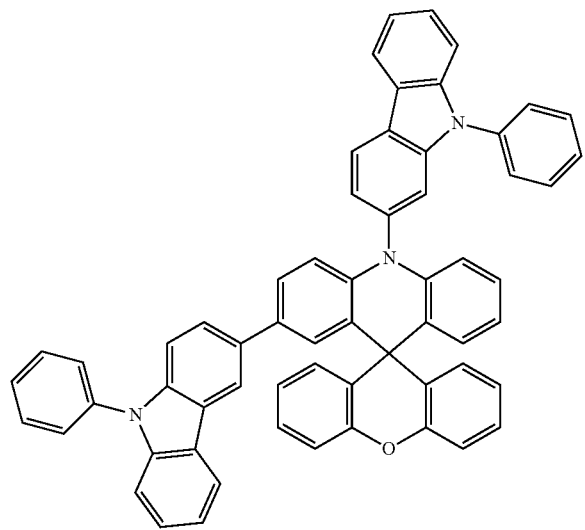
14
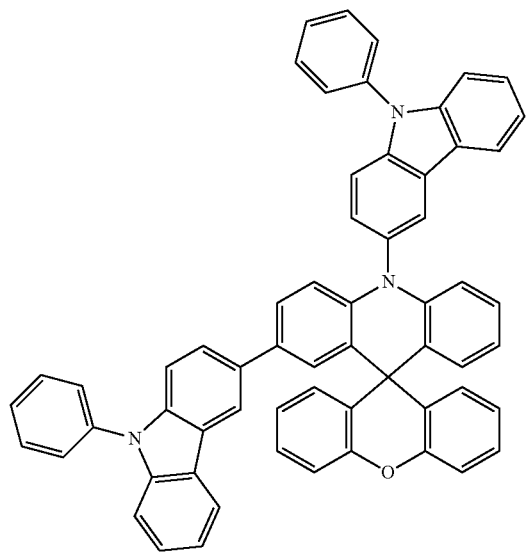
15
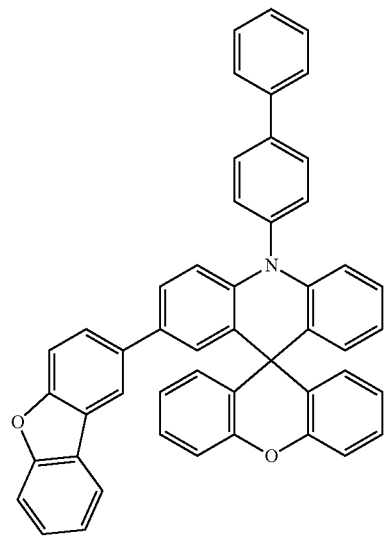
16
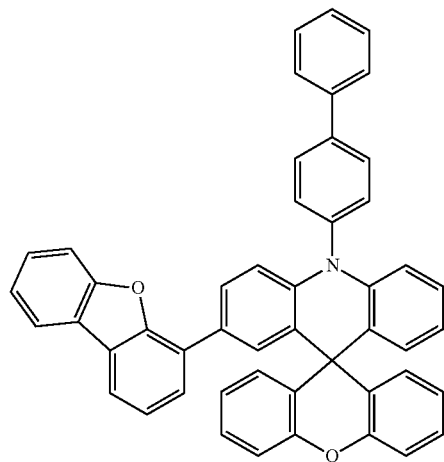

-continued
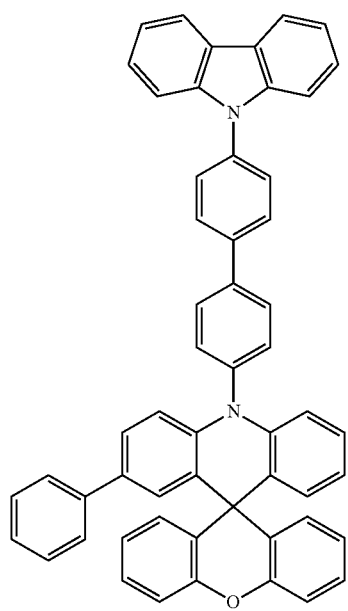
17
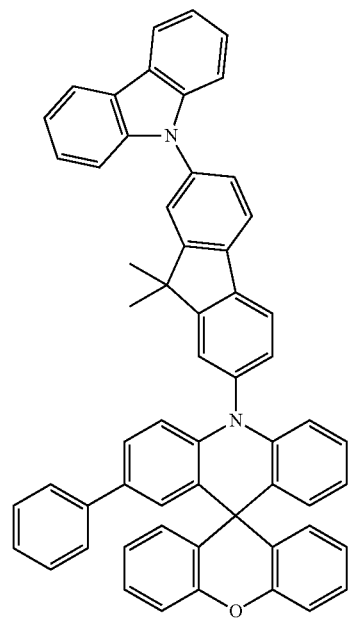
18
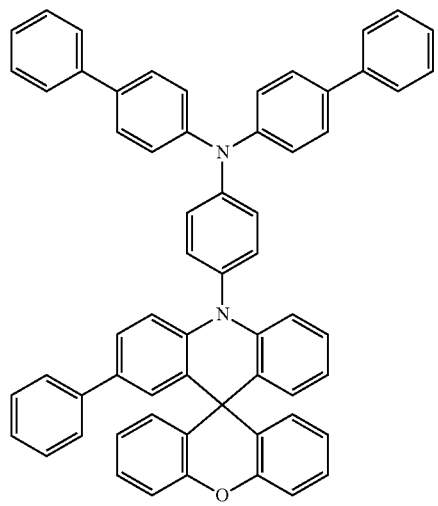
19
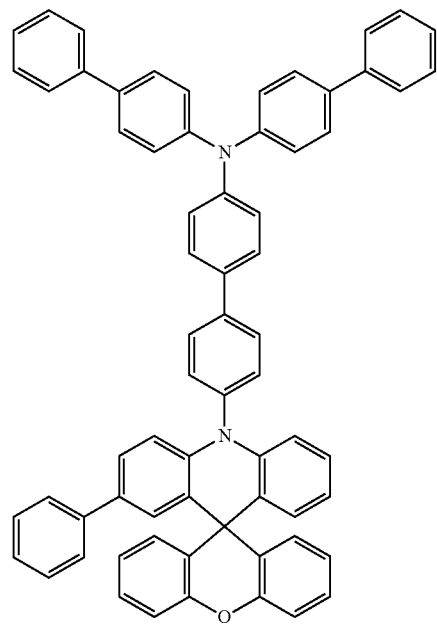
20

-continued
21
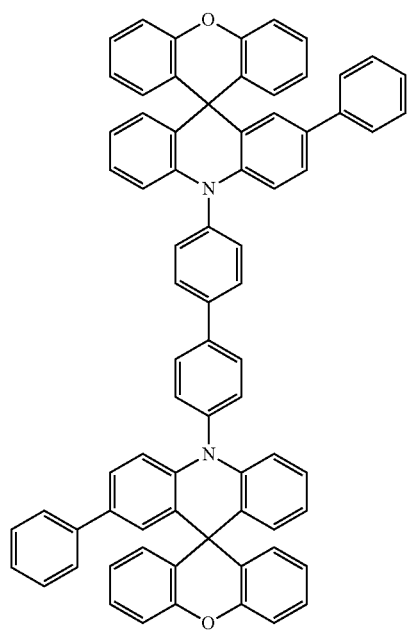
22
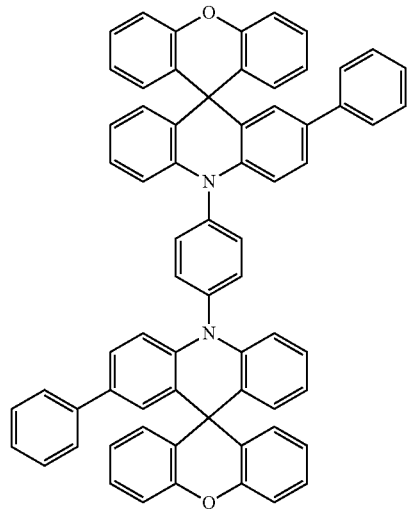
23
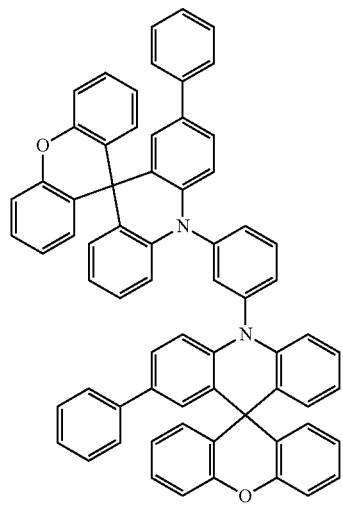
24
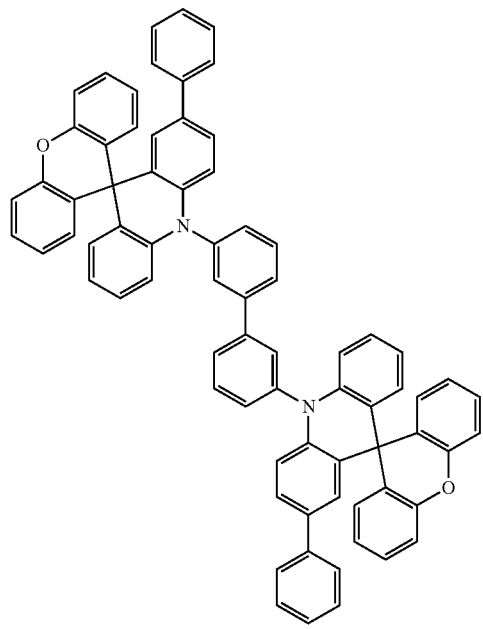

-continued
25
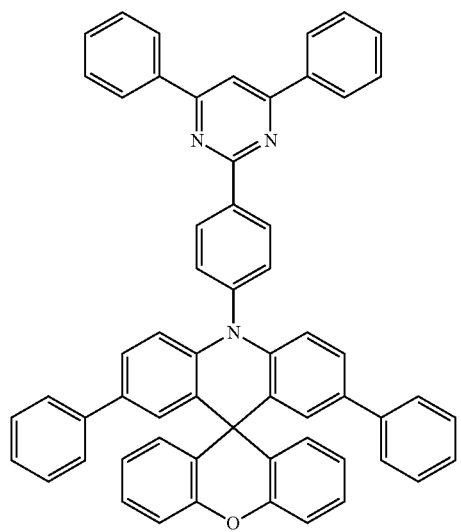
26
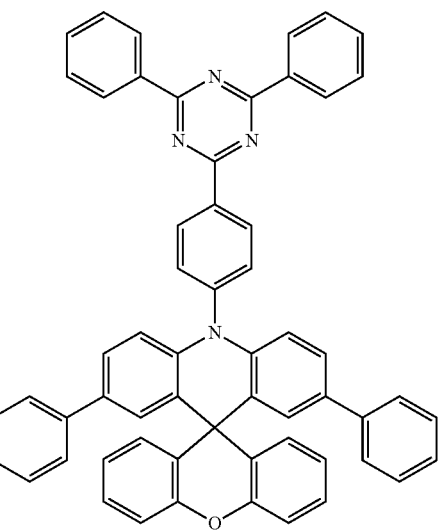
27
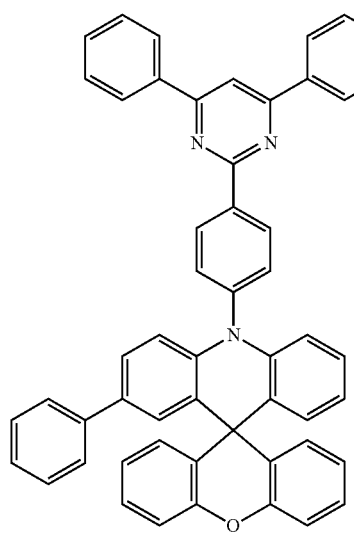
28
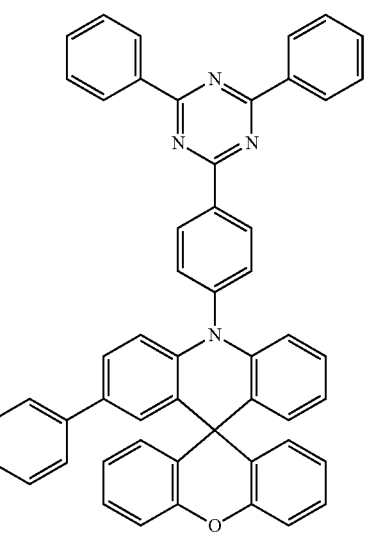
29
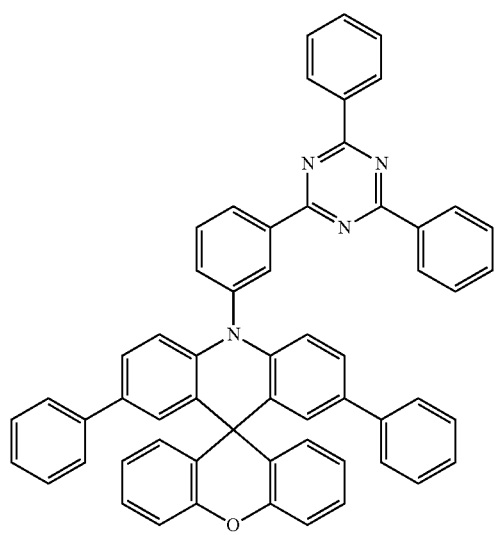
30
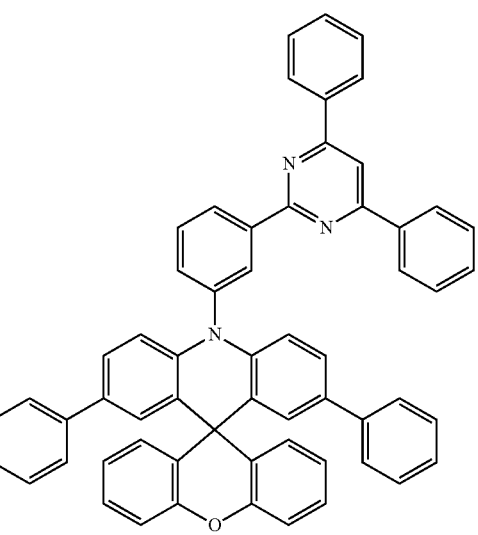

-continued
31
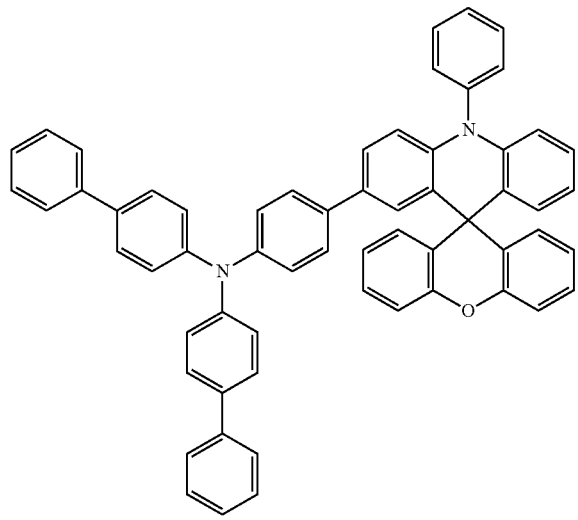
32
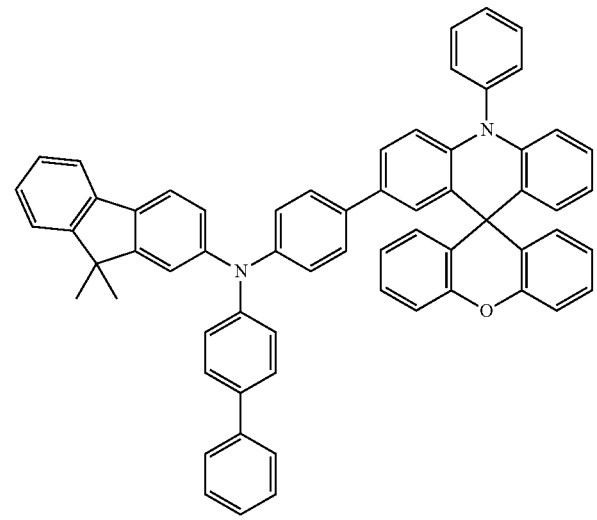
33
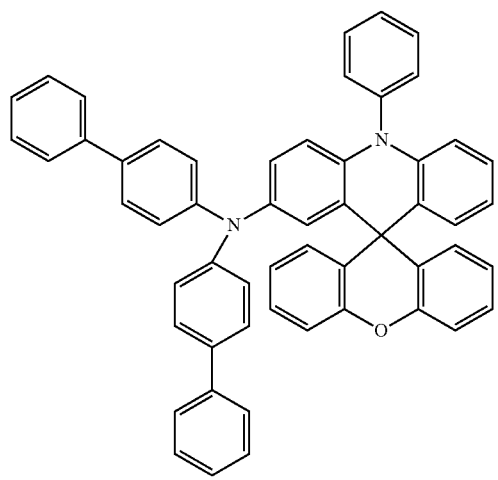
34
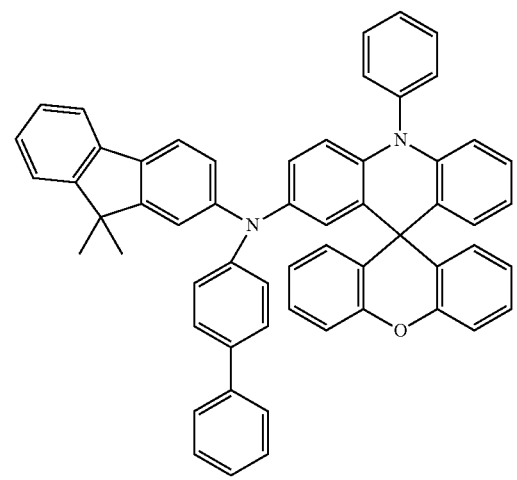
35
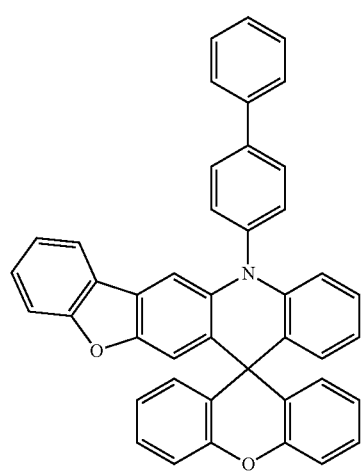
36
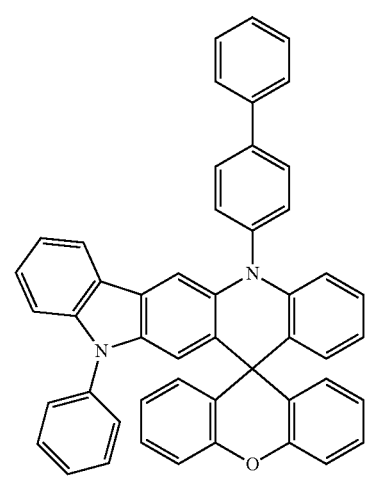

-continued
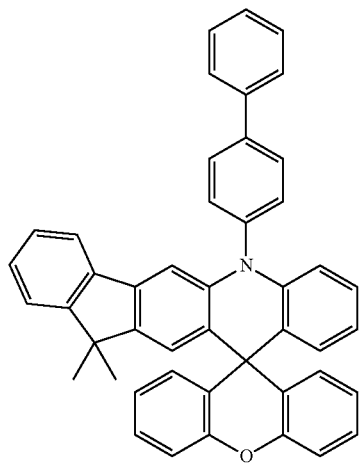
37
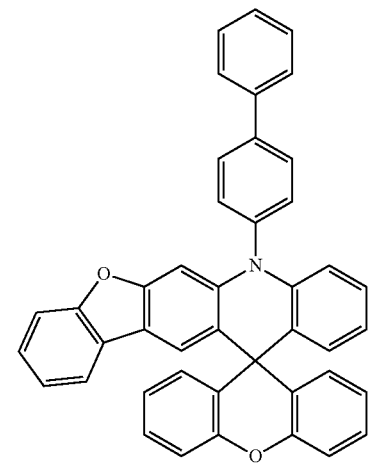
38
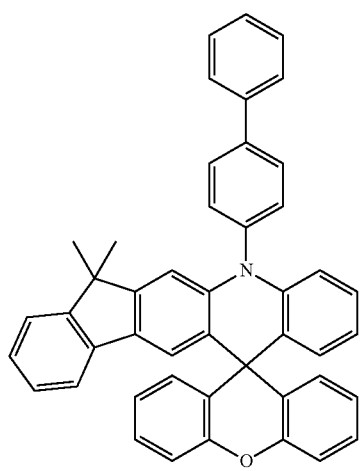
39
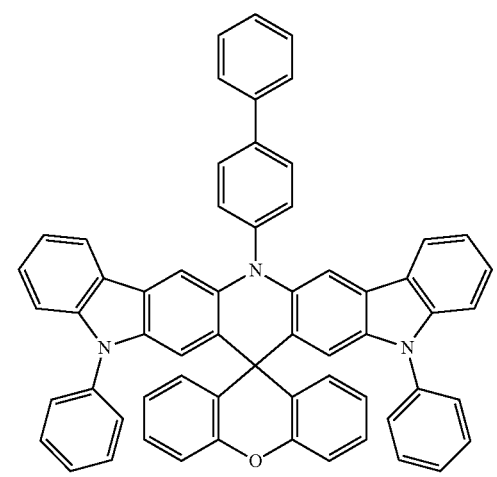
40
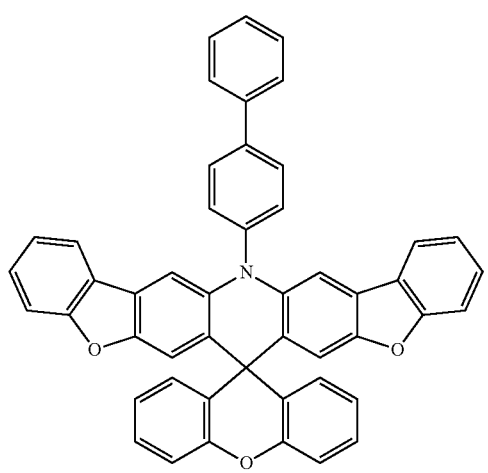
41
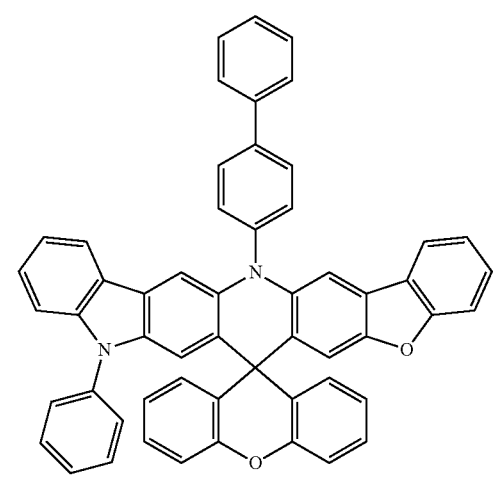
42

-continued
| 43 | 44 |
|---|---|
| 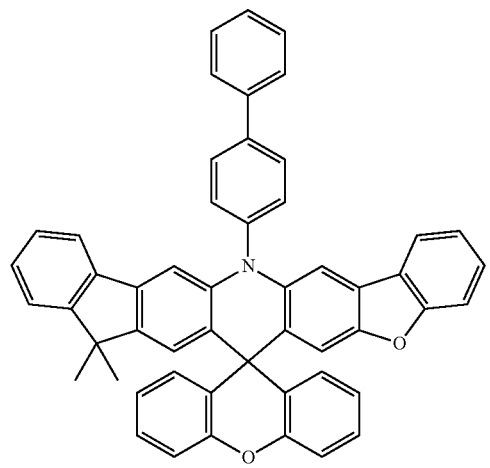 | 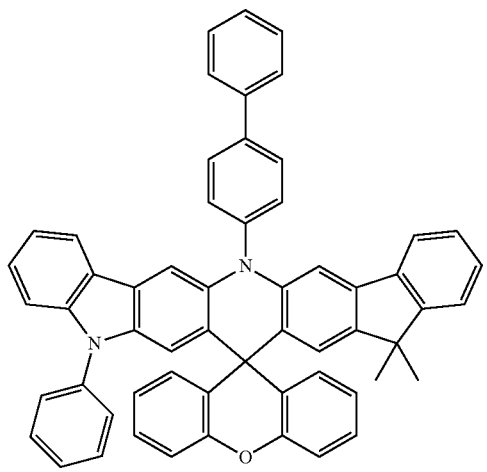 |
| 45 | 46 |
|---|---|
| 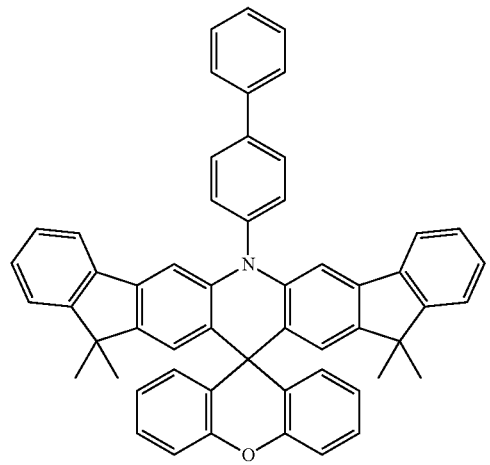 | 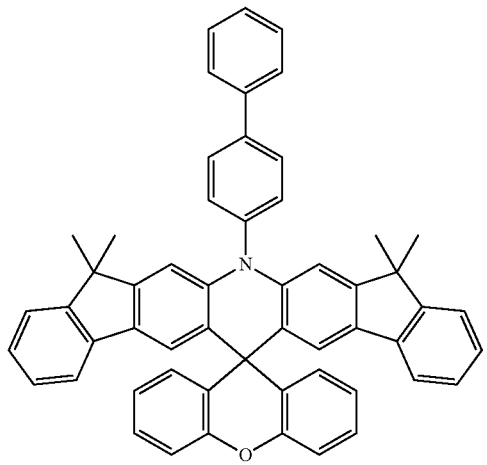 |
| 47 | 48 |
|---|---|
| 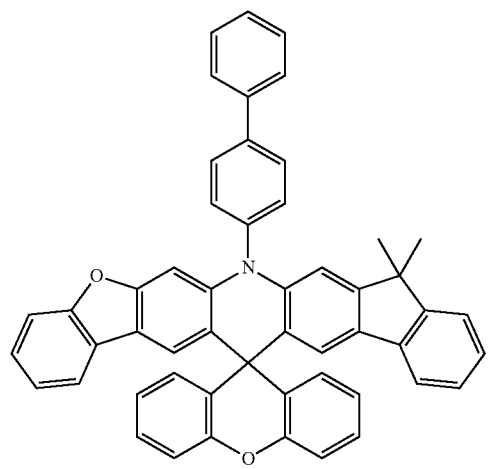 | 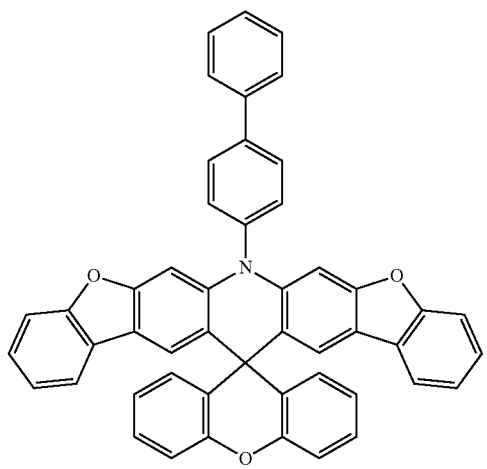 |

-continued
49
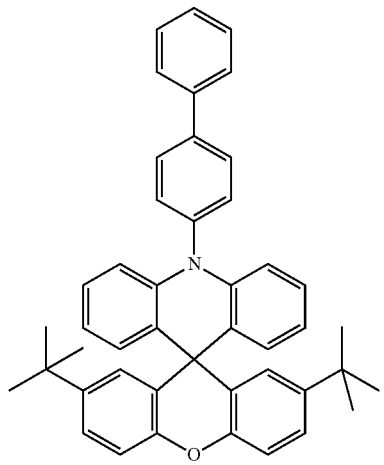
50
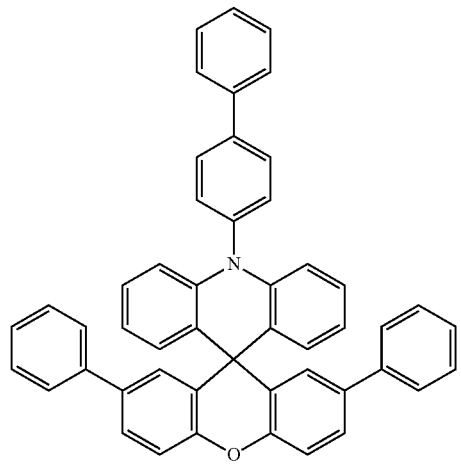
51
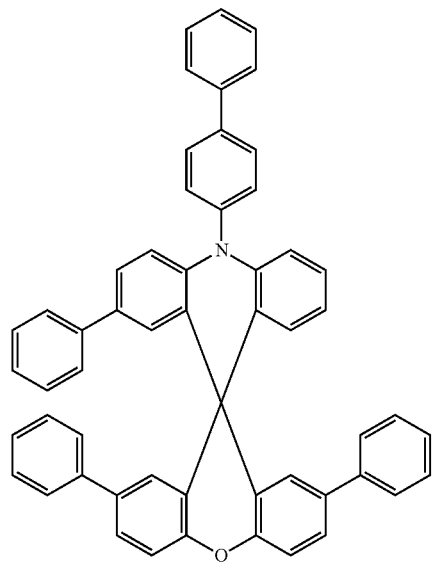
52
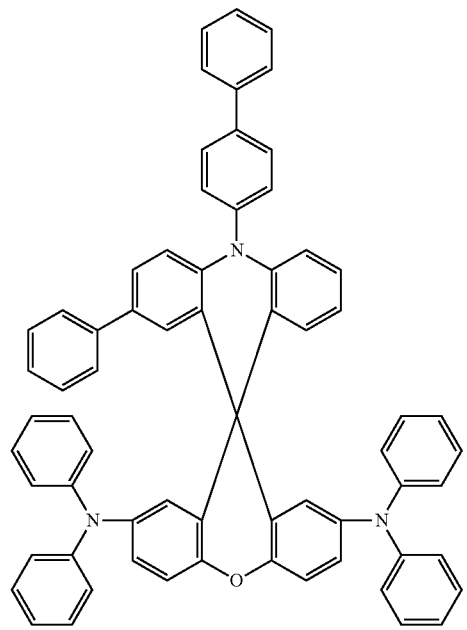
53
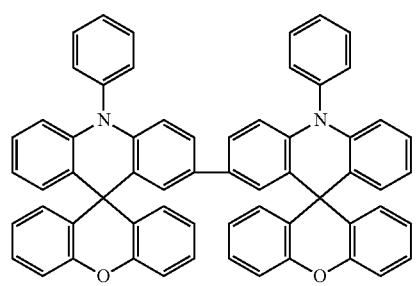
54
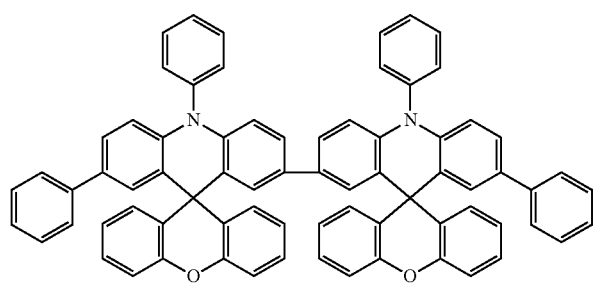

-continued
55
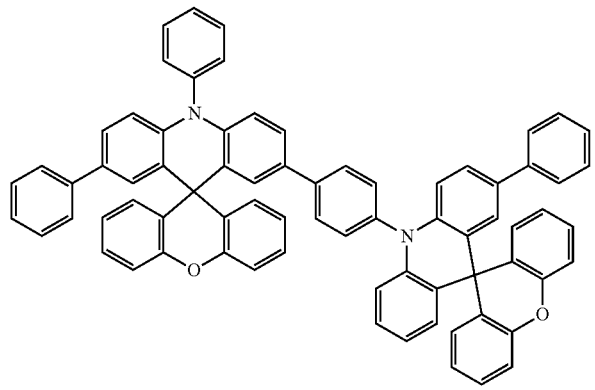
56
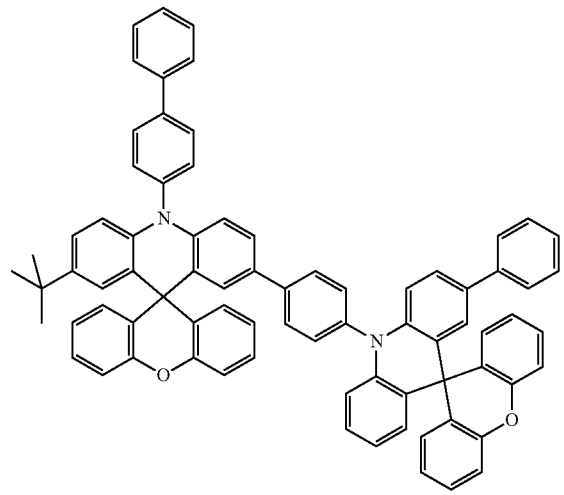
57
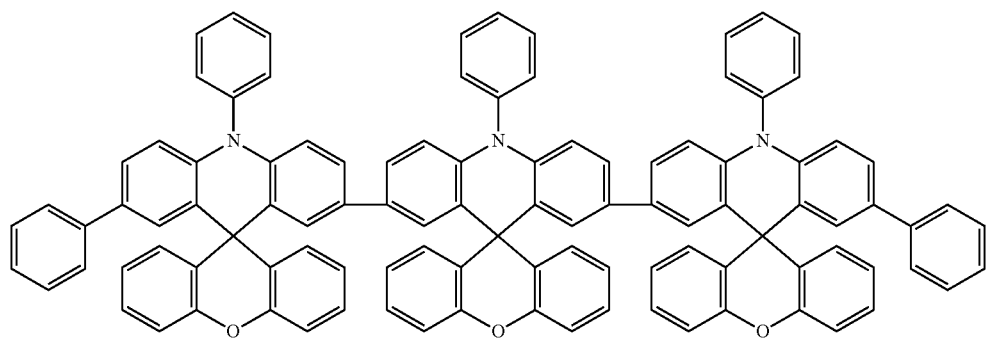
58
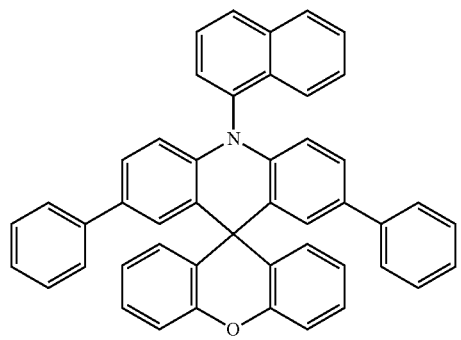
59
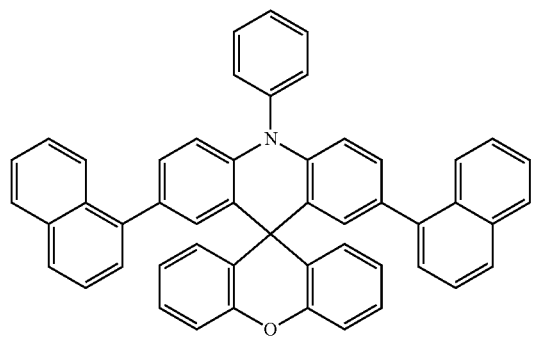
60
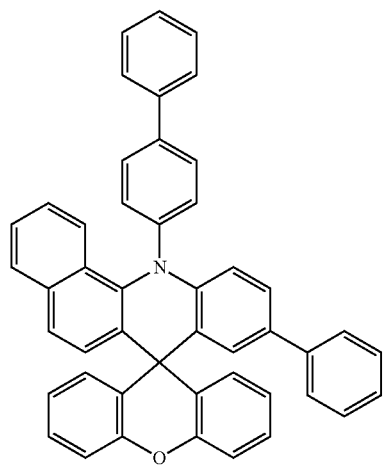
61
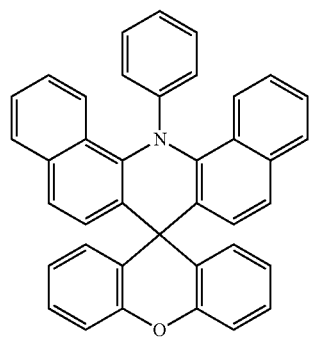

-continued
62
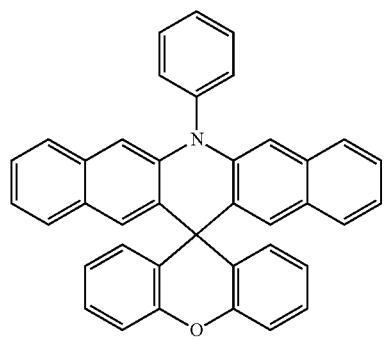
63
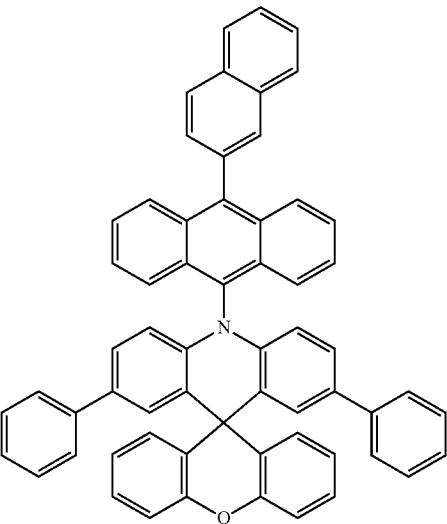
64
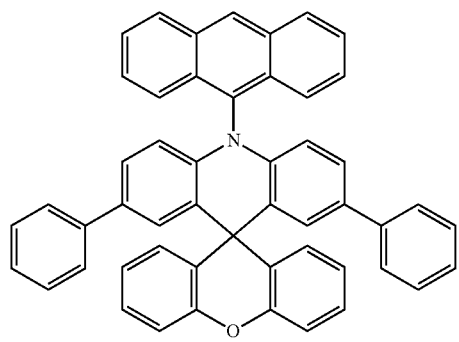
65
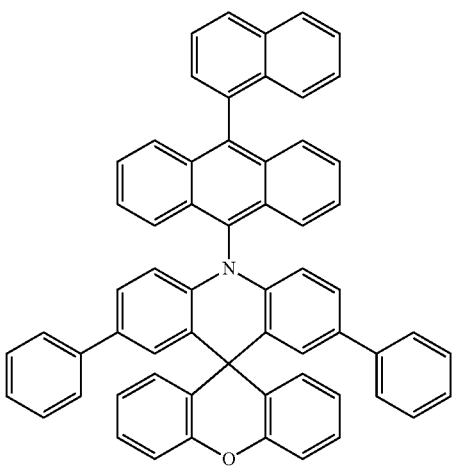
66
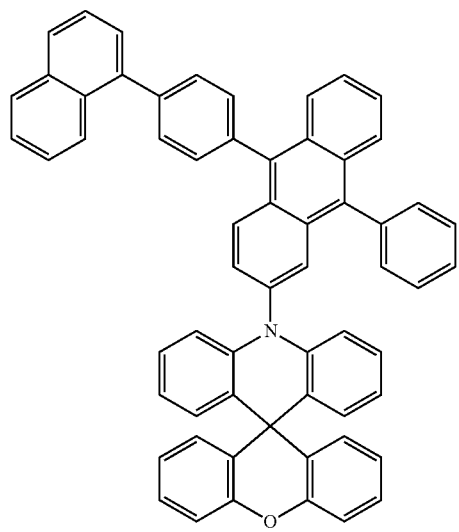
67
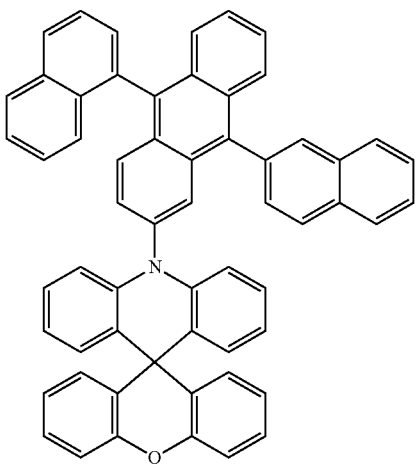

-continued
68
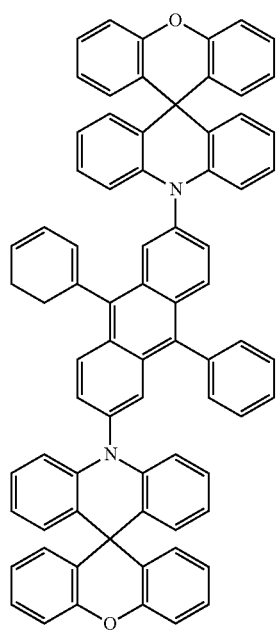
69
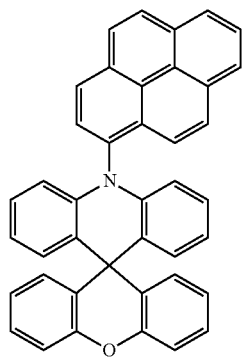
70
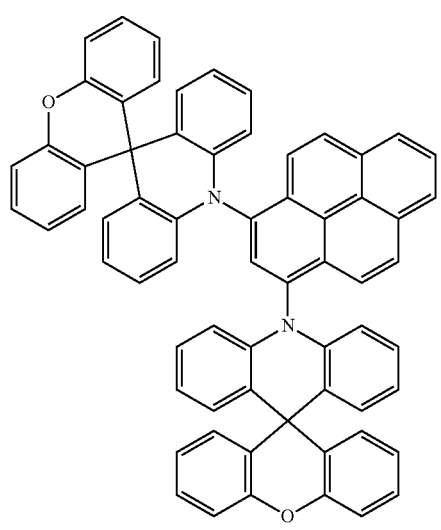
71
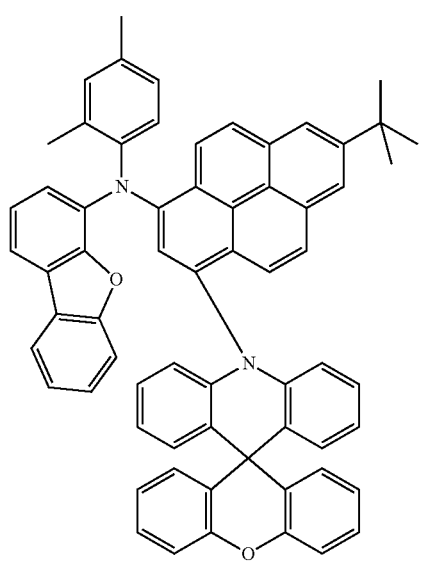

-continued
72
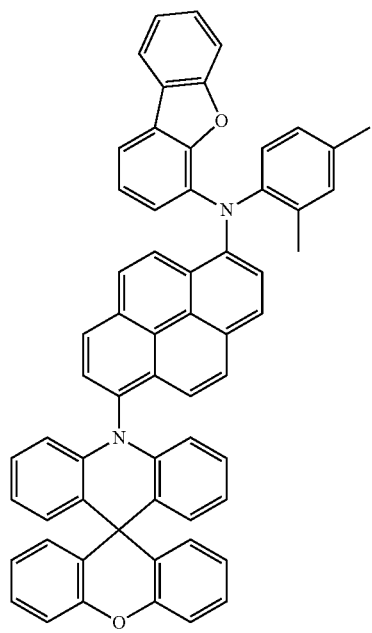
73
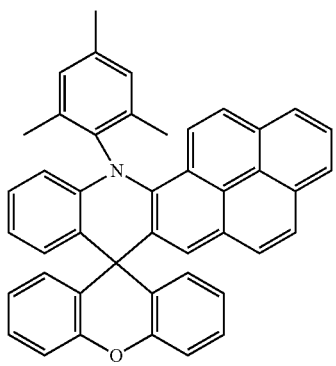
74
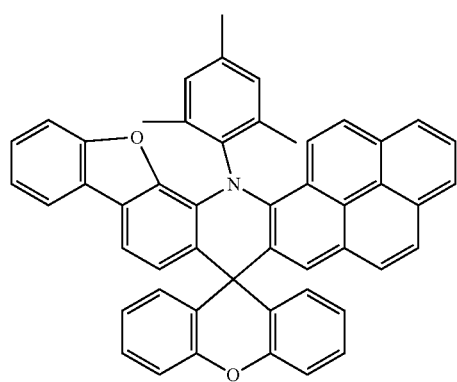
75
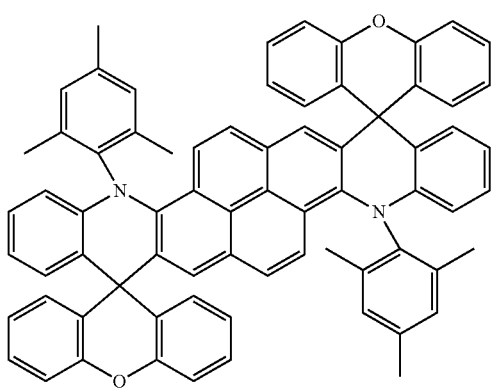
76
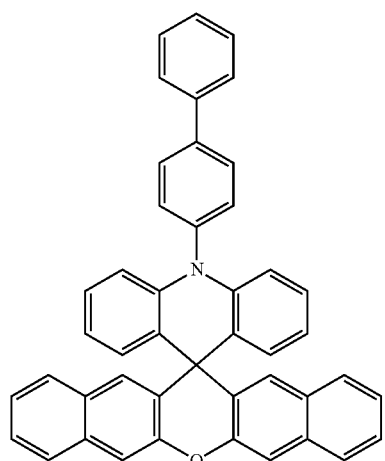
77
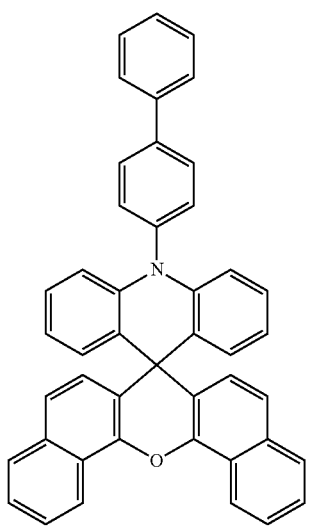

-continued
78
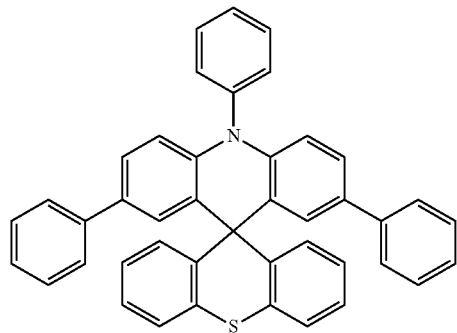
79
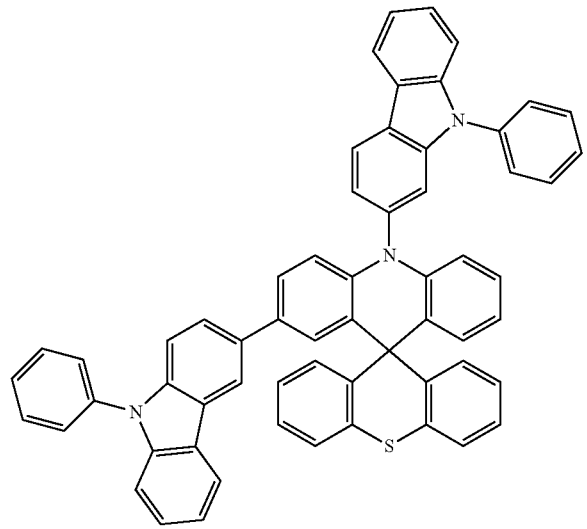
80
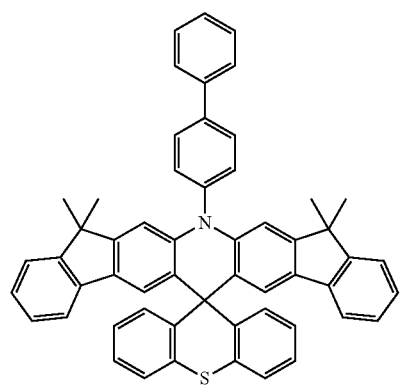
81
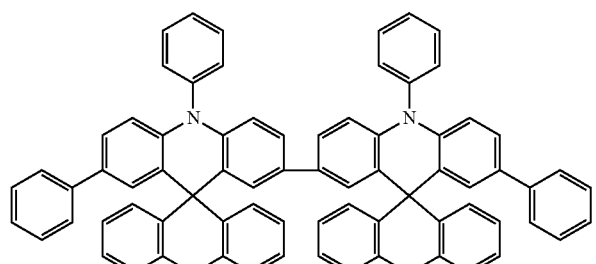
82
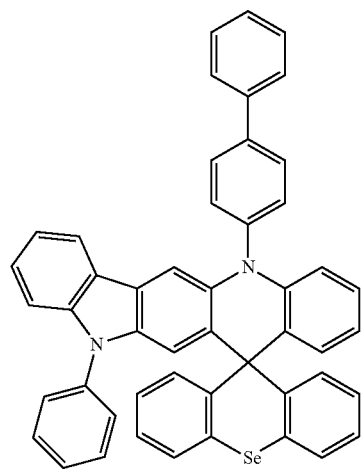
83
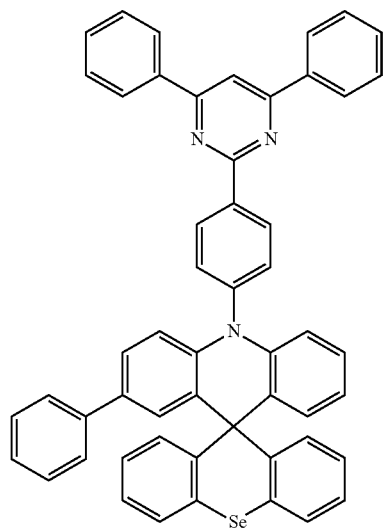

-continued
84
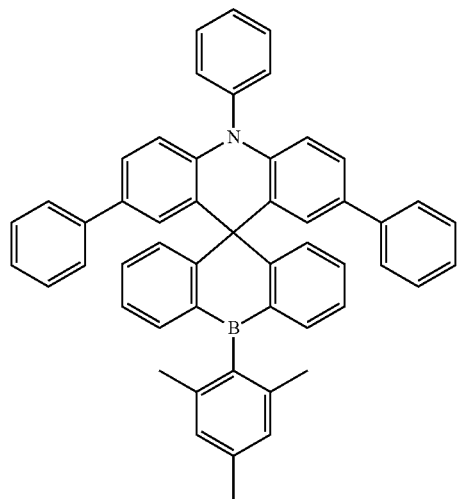
85
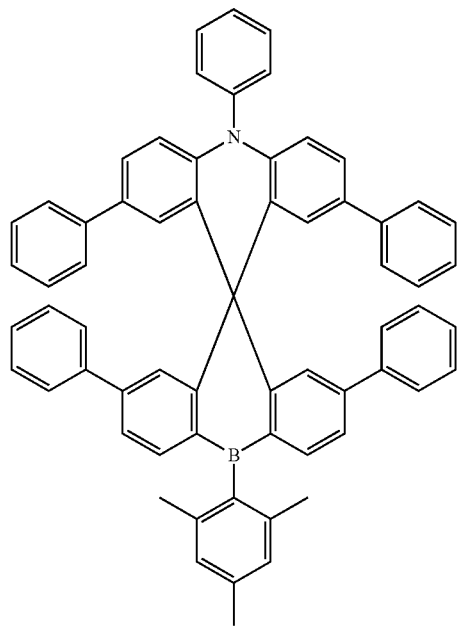
86
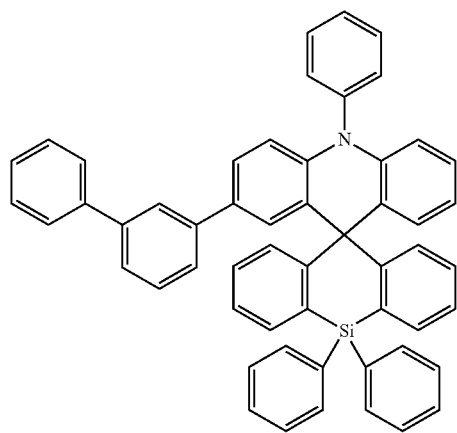
87
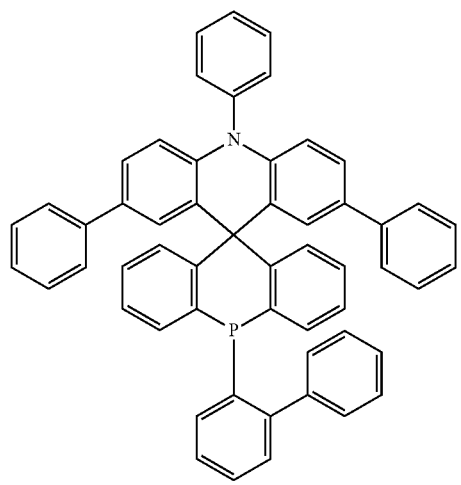
88
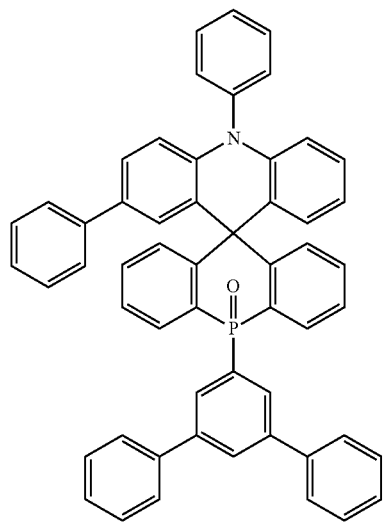
89
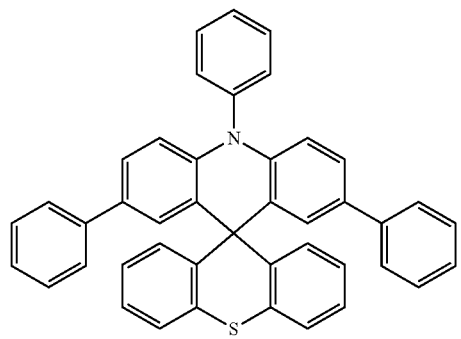

-continued
90 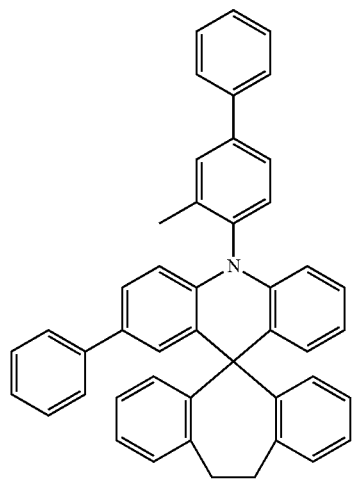
91 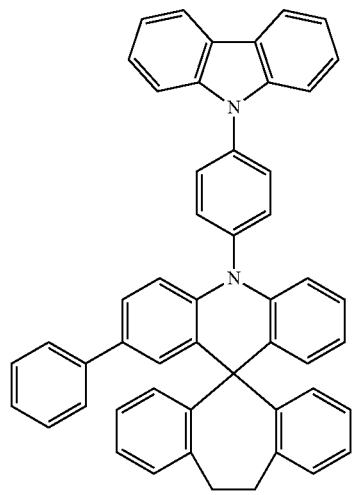
92 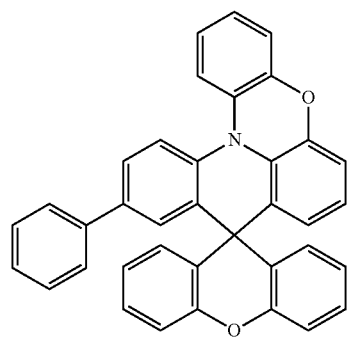
93 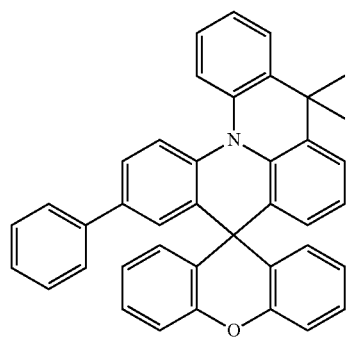
94 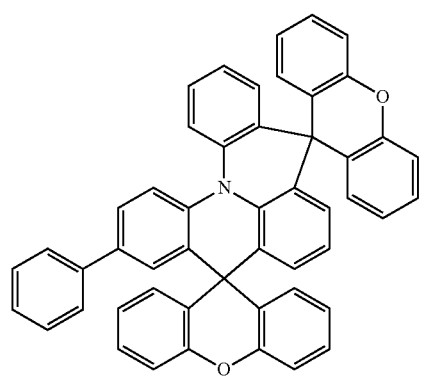
95 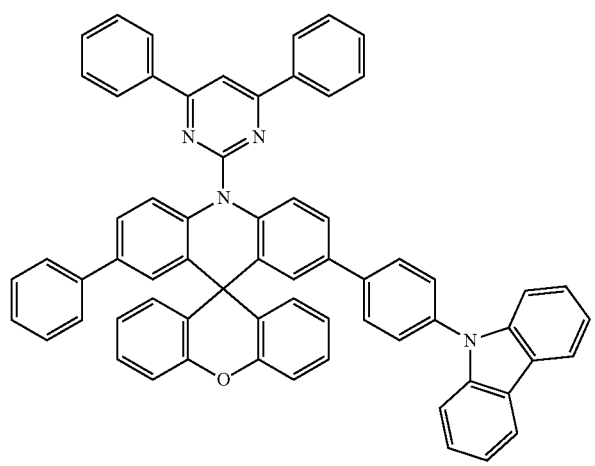

-continued

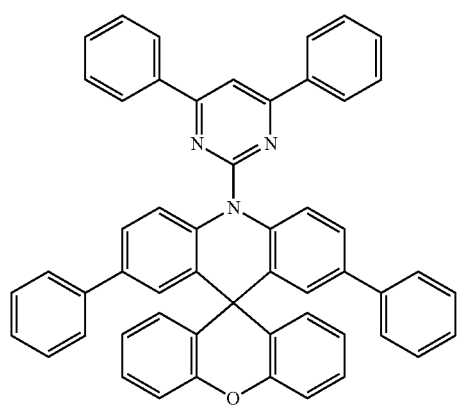
96

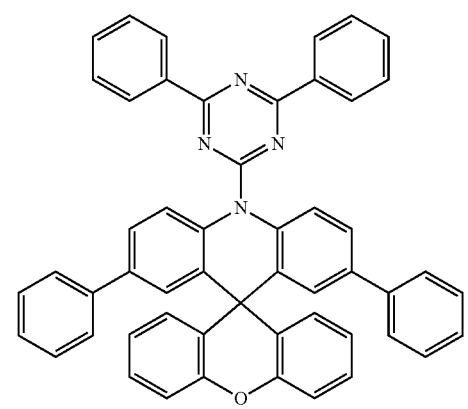
97

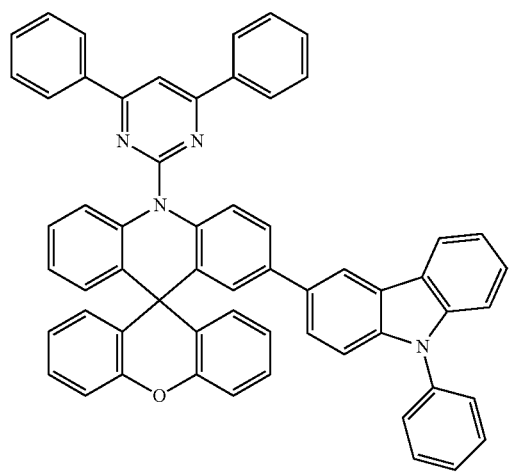
98

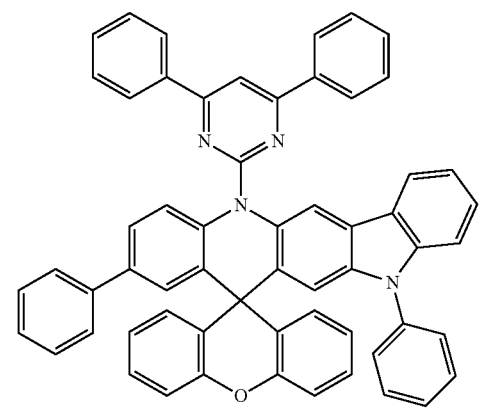
99

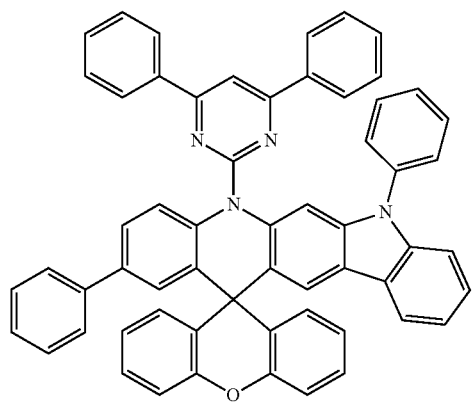
100

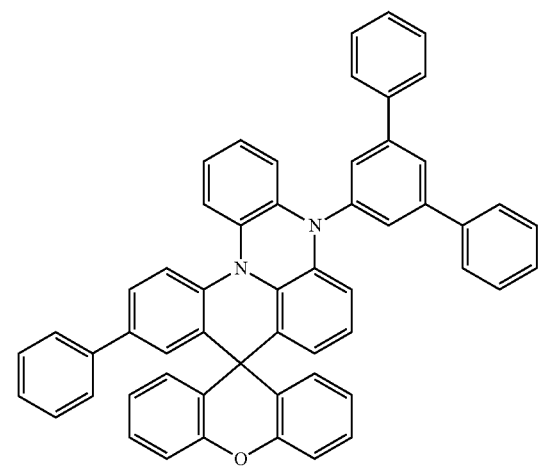
101

The compounds according to the invention can be prepared by the routes outlined in Scheme 1 to 4.

Starting from a 1,2-dihalogen-substituted aromatic or heteroaromatic compound, a Buchwald or Ullmann coupling to a secondary amine results in an o-halogen-functionalised tertiary amine. This can be coupled, after metallation, to a heterocyclic ketone to give a triarylmethanol, which cyclises under acid catalysis to give the spiro compound (A) according to the invention (Scheme 1). The spiro compound (A) can be mono- or dibrominated (optionally also tri-, tetra-, etc., brominated with involvement of further active positions) regioselectively—preferably in the p-position to the N atom, the bromides (B) and (C) formed in this way can subsequently be reacted further by methods familiar to the person skilled in the art (C—C coupling, such as Suzuki, Negishi, Yamamoto, Grignard-Cross, Stille, Heck coupling, etc.; C—N coupling, such as Buchwald or Ullmann coupling, silylation, phosphanylation, boranylation, polycondensation, etc.). Besides regioselective bromination, reaction with other electrophiles, for example in Friedel-Crafts alkylation or acylation, sulfonation, nitration, etc., is of course also possible.

Scheme 1:

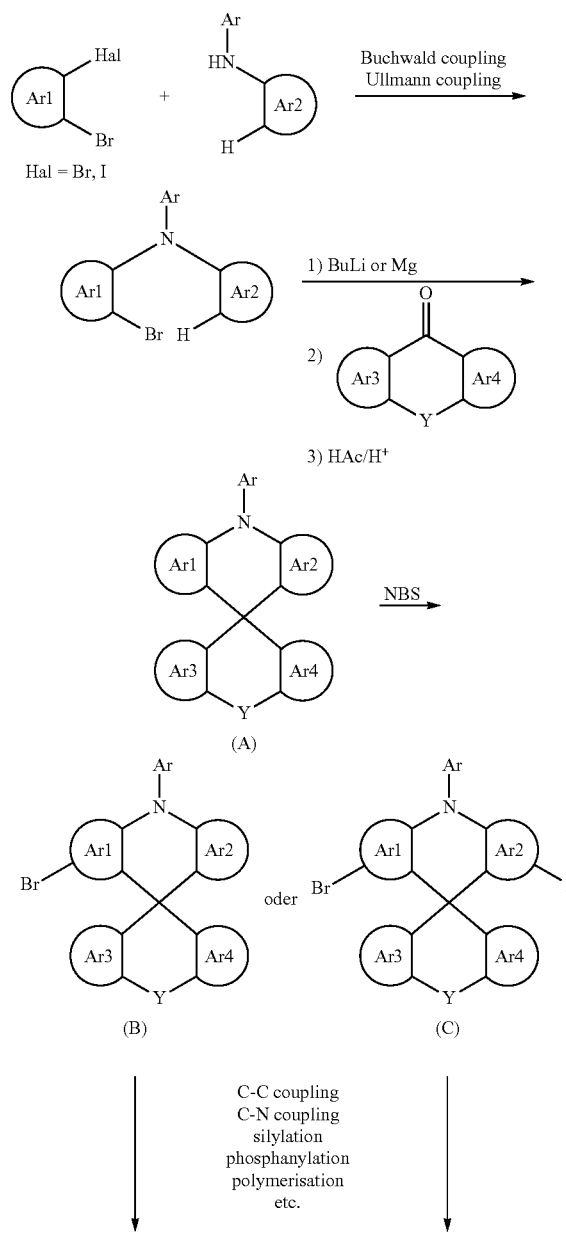

If the secondary amine carries a protecting group PG (for example N-acyl, N-Boc, N-benzyl, N-sulfenyl, N-silyl, etc.) at the beginning of the sequence, the secondary spiroamine (E) can be obtained after build-up of the spiro compound (D) by removal of the protecting group and can be reacted further by C—N coupling methods familiar to the person skilled in the art (Buchwald or Ullmann coupling, etc.) (Scheme 2). Compounds according to the invention containing a plurality of units (E) are accessible by this route by coupling to polyfunctionalised aromatic compounds. These can then be functionalised further via the route described in Scheme 1 of reaction with electrophiles.

Scheme 2:

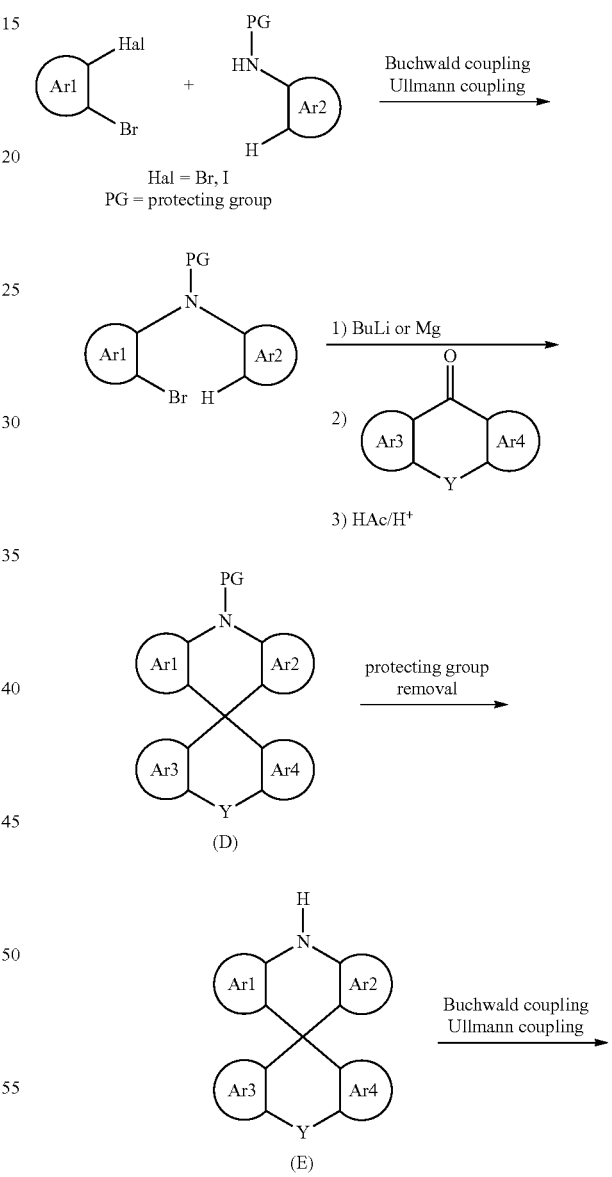

The bromide (B) is additionally suitable for the build-up of extended condensed heterocyclic compounds according to the invention (Scheme 3). Suzuki coupling of (B) to o-YH-functionalised aromatic or heteroaromatic compounds results in (F), which can be cyclised to give (G). Analogously, a Buchwald or Ullmann coupling of (B) results in (H), which can be cyclised to give (I).

Scheme 3:
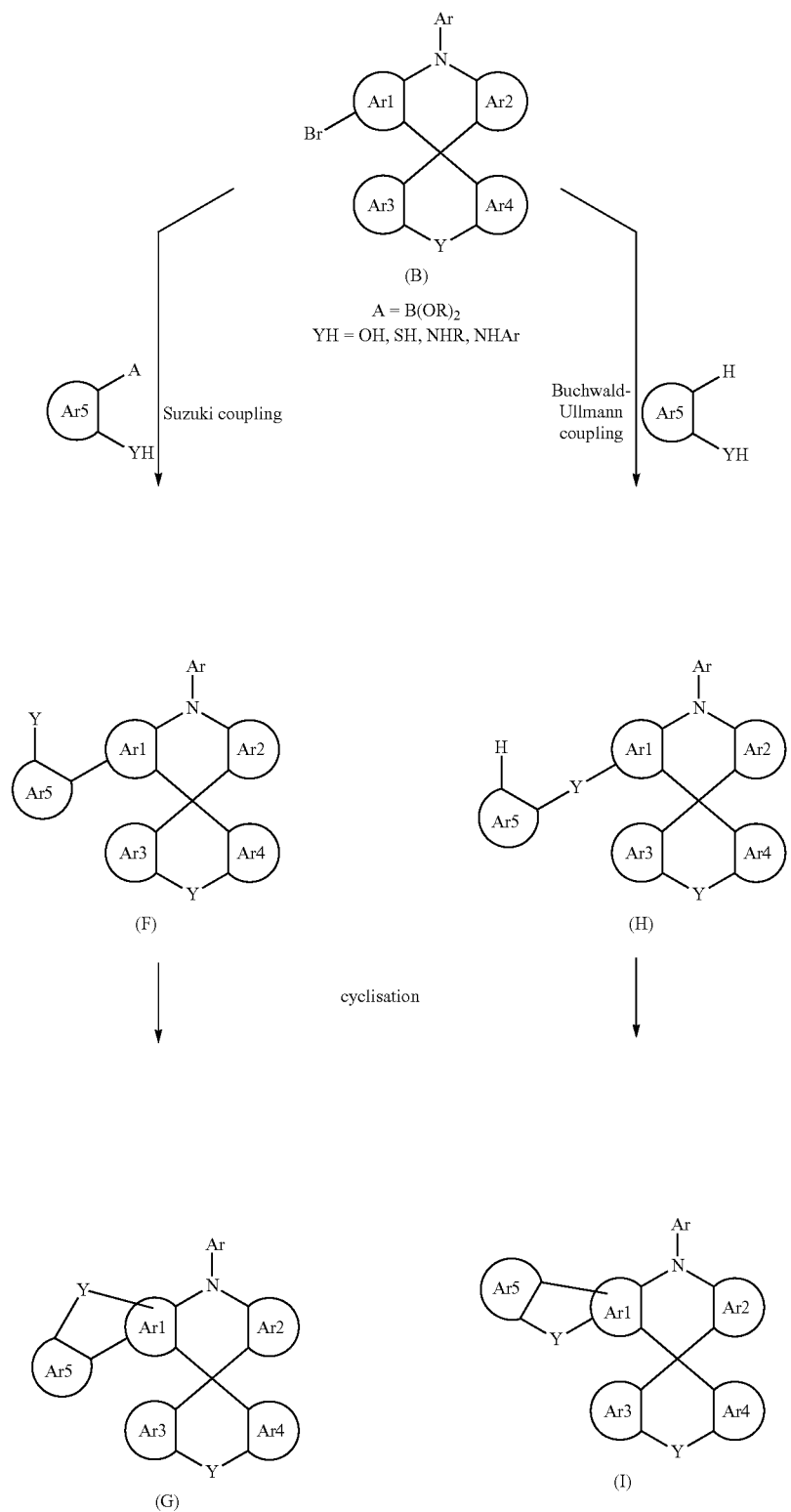
The spiroamine (E) is furthermore suitable for the build-up of extended condensed heterocyclic compounds (K) according to the invention (Scheme 4). C—N coupling of (E) to o-halogen-functionalised aromatic compounds which carry YH functions and subsequent cyclisation of the intermediate (J) results in extended heterocyclic compounds (K).

Scheme 4:

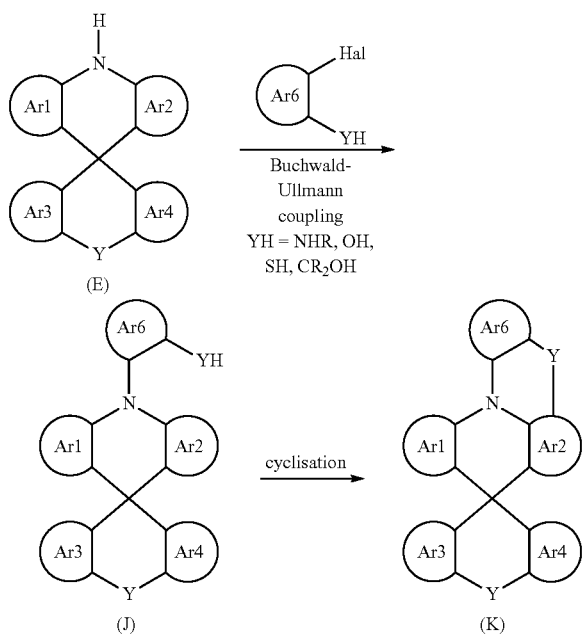

The reactions shown in Scheme 3 and 4 are of course also possible analogously with the dibromide (C). In this way, condensed heterocyclic compounds containing fluorenes, dibenzofurans, thiodibenzofurans, carbazoles, etc. can be obtained by methods familiar to the person skilled in the art.

The present invention furthermore relates to a process for the preparation of a compound of the formula (1), (2) or (3), comprising the reaction steps:
a) build-up of the halogenated skeleton; and
b) introduction of substituents via a transition-metal-catalysed coupling reaction.

The compounds according to the invention described above, in particular compounds which are substituted by reactive leaving groups, such as bromine, iodine, chlorine, boronic acid or boronic acid ester, or by reactive, polymerisable groups, such as olefins, styrenes, acrylates or oxetanes, can be used as monomers for the generation of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the compounds according to the invention indicated above, where one or more bonds from the compound according to the invention to the polymer, oligomer or dendrimer are present at one or more positions instead of substituents. Depending on the linking of the compound according to the invention, this forms a side chain of the oligomer or polymer or is linked in the main chain or forms the core of a dendrimer. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers in which the units of the formula (1) or the preferred embodiments indicated above are present to the extent of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. In particular, the combination of the oligomers, polymers or dendrimers according to the invention with triplet emitters leads to particularly good results.

Furthermore, the compounds according to the invention may also be functionalised further and thus converted into extended structures. An example which may be mentioned here is the reaction with arylboronic acids by the Suzuki method or with primary or secondary amines by the Hartwig-Buchwald method. Thus, the compounds according to the invention can also be bonded directly to phosphorescent metal complexes or also to other metal complexes.

The compounds according to the invention are suitable for use in an electronic device, in particular in an organic electroluminescent device.

The present invention therefore furthermore relates to the use of a compound according to the invention in an electronic device, in particular in an organic electroluminescent device.

The present invention still furthermore relates to an electronic device comprising at least one compound according to the invention.

An electronic device in the sense of the present invention is a device which comprises at least one layer which comprises at least one organic compound. The component may also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs), particularly preferably phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). The organic electroluminescent device according to the invention may also be a tandem OLED, in particular also for white-emitting OLEDs.

The compound according to the invention in accordance with the embodiments indicated above can be employed in various layers, depending on the precise structure. Preference is given to an organic electroluminescent device comprising a compound of the formula (1), (2) or (3) or the preferred embodiments indicated above as matrix material for fluorescent or phosphorescent emitters and/or as fluorescent emitters, in particular as blue-fluorescent emitters, and/or in an electron-blocking or exciton-blocking layer and/or in a hole-transport layer and/or in a hole-blocking layer and/or in an electron-transport layer, depending on the precise substitution.

In a further embodiment of the invention, the organic electroluminescent device comprises the compound according to the invention in an optical coupling-out layer. An optical coupling-out layer here is taken to mean a layer which is not located between the anode and the cathode, but instead which is applied to an electrode outside the actual device, for example between an electrode and a substrate, in order to improve the optical coupling-out.

In a preferred embodiment of the invention, the compound according to the invention is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound according to the invention as matrix material.

If the compound according to the invention is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state>1, in particular from an excited triplet state. In the sense of this application, all luminescent complexes containing transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527, WO 2008/086851 or the carbazole derivatives disclosed in the unpublished application EP 11007693.2, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with WO 2011/042107, WO 2011/060867, WO 2011/088877 and the unpublished application EP 11003232.3, or triphenylene derivatives, for example in accordance with WO 2012/048781. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339 or WO 2012/007086. Also suitable are, for example, the metal complexes disclosed in the unpublished applications EP 11004545.7, EP 11005252.9 and EP 11006562.0. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is the same as or similar to the metal complex in the emitting layer as hole-transport or hole-injection material directly adjacent to the emitting layer, as described, for example, in WO 2009/030981.

Preference is given to the use of the compound of the formula (1), (2) or (3) in a hole-transport or hole-injection or electron-blocking or exciton-blocking layer.

In a preferred embodiment of the invention, the compounds of the formula (1), (2) or (3) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer.

If the compounds of the formula (1), (2) or (3) are used as hole-transport material or as hole-injection material, it may be preferred for them to be doped with electron-acceptor compounds, for example with $F_4$-TCNQ or with compounds as described in EP 1476881 or EP 1596445.

Suitable dopants are in principle all compounds which are electron-acceptor compounds and are able to increase the conductivity of the organic layer by oxidation of the host. The person skilled in the art will be able to identify further suitable compounds without major effort on the basis of his general expert knowledge and employ them in combination with the compounds according to the invention. Particularly suitable dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

In a further preferred embodiment of the invention, a compound of the formula (1), (2) or (3) is used as hole-transport material in combination with a hexaazatriphenylene derivative, as described in US 2007/0092755. The hexaazatriphenylene derivative here is particularly preferably employed in a separate layer.

If the compound of the formula (1), (2) or (3) is employed as hole-transport material in a hole-transport layer, the compound can be employed as pure material, i.e. in a proportion of 100%, in the hole-transport layer, or it can be employed in combination with one or more further compounds in the hole-transport layer.

In still a further preferred embodiment of the invention, the compound according to the invention is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound according to the invention is employed in a hole-blocking layer. A hole-blocking layer is taken to mean a layer which is directly adjacent to an emitting layer on the cathode side.

In the further layers of the organic electroluminescent device according to the invention, all materials can be used as are usually employed in accordance with the prior art. The person skilled in the art will therefore be able to employ all materials which are known for organic electroluminescent devices in combination with the compounds of the formula (1) according to the invention or the preferred embodiments indicated above without inventive step.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by the following surprising advantages over the prior art:

1. The compounds according to the invention, employed as matrix material for fluorescent or phosphorescent emitters, result in very high efficiencies and in long lifetimes. This applies, in particular, if the compounds are employed as matrix material for a phosphorescent emitter.

2. The compounds according to the invention are suitable not only as matrix for red-phosphorescent compounds, but also for green- and possibly also for blue-phosphorescent compounds.

3. The compounds according to the invention are very highly suitable for use in a hole-transport layer or electron-blocking layer, where they result in very good efficiencies and lifetimes of the electronic devices.

4. The compounds according to the invention can be prepared in very high yield and very high purity, which means that complex purification, which is always also associated with losses of material, can be omitted or at least is only necessary to a considerably reduced extent.

5. The compounds according to the invention have high thermal stability, which offers advantages not only in the production of the OLEDs by vacuum evaporation, but also in the purification by sublimation methods.

These advantages mentioned above are not accompanied by an impairment in the other electronic properties.

The invention is explained in greater detail by the following examples without wishing to restrict it thereby. The person skilled in the art will be able to use the descriptions to carry out the invention throughout the range disclosed and prepare further compounds according to the invention without inventive step and use them in electronic devices or apply the process according to the invention.

EXAMPLES

The following syntheses are carried out, unless indicated otherwise, under a protective-gas atmosphere in dried solvents. The solvents and reagents can be purchased from ALDRICH or ABCR. The numbers in square brackets indicated in the case of the starting materials which are not commercially available are the corresponding CAS numbers.

Example 1: (2-Bromophenyl)phenyl-(2,4,6-trimethylphenyl)amine, synthone S1

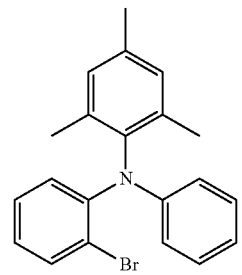 [SMILES: Cc1cc(C)c(N(c2ccccc2)c2ccccc2Br)c(C)c1]

50 ml (50 mmol) of tri-tert-butylphosphine (1 M in toluene), 5.6 g (25 mmol) of palladium(II) acetate and, after stirring for 5 min, 115.3 g (1.2 mol) of sodium tert-butoxide are added to a mixture of 211.3 g (1 mol) of mesitylphenylamine [23592-67-8], 311.3 g (1.1 mol) of 1-bromo-2-iodobenzene [583-55-1] and 1500 ml of toluene, and the mixture is then heated under reflux for 16 h. After cooling, 500 ml of water are added with stirring, the aqueous phase is separated off, the organic phase is washed twice with 500 ml of saturated sodium chloride solution each time, dried over magnesium sulfate, the toluene is removed in vacuo, and the oil remaining is recrystallised from about 1000 ml of 1-butanol. Yield: 224.0 g (611 mmol), 61%; purity: according to NMR, the product comprises about 15% of (2-iodophenyl)phenyl(2,4,6-trimethylphenyl)amine, it is subsequently reacted without further purification.

The following compounds can be obtained analogously:

| Ex. | Secondary amine | Product | Yield |
|---|---|---|---|
| 2 | [102113-98-4] | S2 | 68% |

-continued
| Ex. | Secondary amine | Product | Yield |
|---|---|---|---|
| 3 | 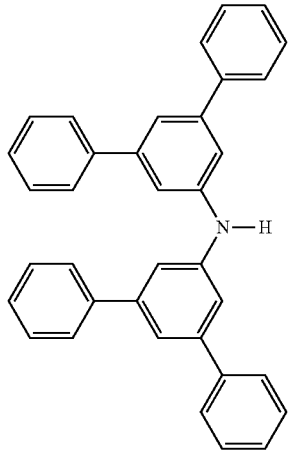 [SMILES: c1ccc(-c2cc(Nc3cc(-c4ccccc4)cc(-c4ccccc4)c3)cc(-c3ccccc3)c2)cc1] [1290039-78-9] | 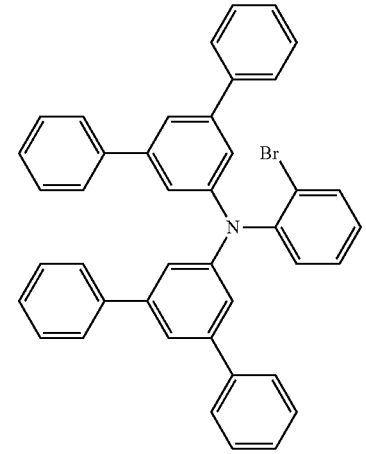 S3 | 56% |
| 4 | 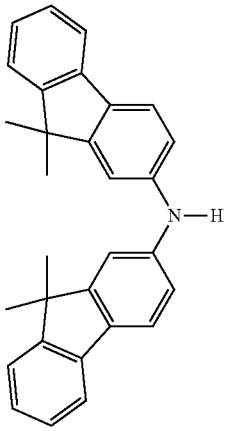 [SMILES: CC1(C)c2ccccc2-c2ccc(Nc3ccc4c(c3)C(C)(C)c3ccccc3-4)cc21] [500717-23-7] | 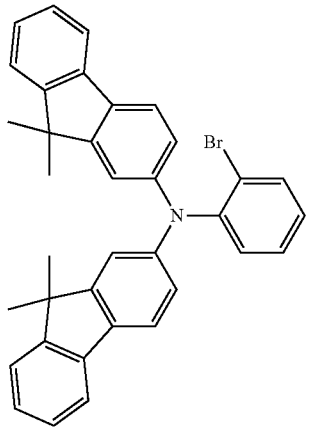 S4 | 58% |
| 5 | 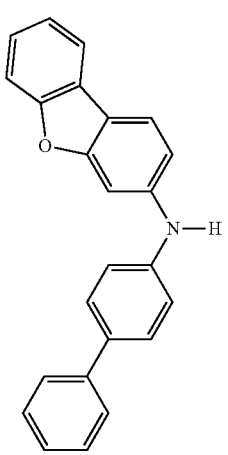 [SMILES: c1ccc(-c2ccc(Nc3ccc4c(c3)oc3ccccc34)cc2)cc1] [1290039-85-8] | 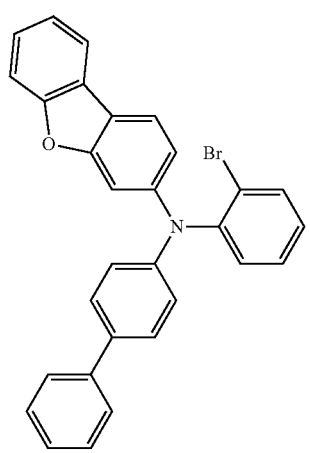 S5 | 64% |

-continued
| Ex. | Secondary amine | Product | Yield |
|---|---|---|---|
| 19 | 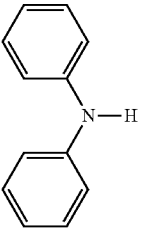 [SMILES: c1ccc(Nc2ccccc2)cc1]<br>122-39-4 | 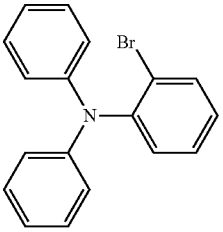 [SMILES: Brc1ccccc1N(c1ccccc1)c1ccccc1]<br>S6 | 69% |
| 20 | 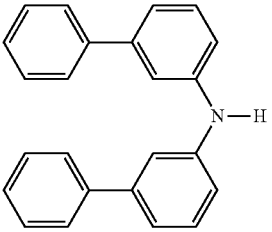 [SMILES: c1ccc(-c2cccc(Nc3cccc(-c4ccccc4)c3)c2)cc1]<br>169224-65-1 | 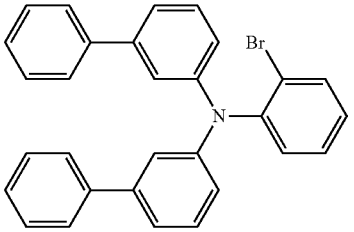 [SMILES: Brc1ccccc1N(c1cccc(-c2ccccc2)c1)c1cccc(-c2ccccc2)c1]<br>S7 | 66% |
| 21 | 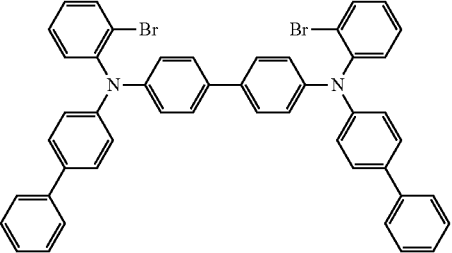 [SMILES: Brc1ccccc1N(c1ccc(-c2ccccc2)cc1)c1ccc(-c2ccc(N(c3ccc(-c4ccccc4)cc3)c3ccccc3Br)cc2)cc1]<br>531-91-9 | 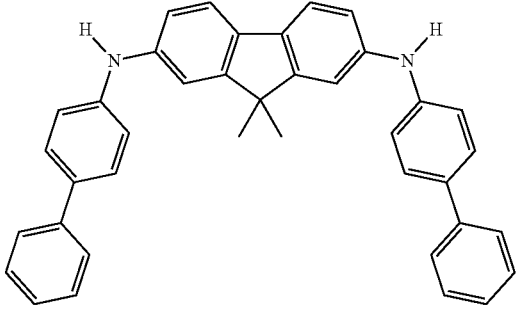 [SMILES: CC1(C)c2cc(Nc3ccc(-c4ccccc4)cc3)ccc2-c2ccc(Nc3ccc(-c4ccccc4)cc3)cc21]<br>S8 | 56% |
| 22 | 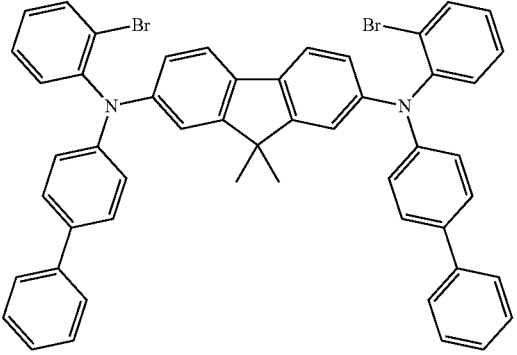 [SMILES: CC1(C)c2cc(N(c3ccc(-c4ccccc4)cc3)c3ccccc3Br)ccc2-c2ccc(N(c3ccc(-c4ccccc4)cc3)c3ccccc3Br)cc21]<br>354987-86-3 | <br>S9 | 57% |

Example 6: 10-Mesitylspiro[acridine-9(10H),9'-xanthene]

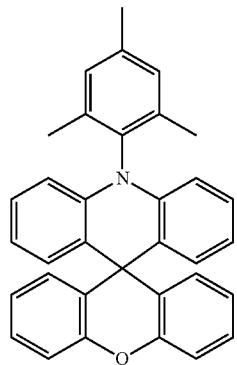 [SMILES: Cc1cc(C)c(N2c3ccccc3C3(c4ccccc4Oc4ccccc43)c3ccccc32)c(C)c1]

100 ml (250 mmol) of n-butyllithium (2.5 M in n-hexane) are added dropwise to a vigorously stirred suspension, cooled to −78° C., of 91.6 g (250 mmol) of (2-bromophenyl)phenyl-(2,4,6-trimethylphenyl)amine (S1) in 750 ml of THF, and the mixture is stirred for a further 30 min. A suspension of 49.1 g (250 mmol) of xanthone [90-47-1] is subsequently added dropwise, the reaction mixture is stirred for a further 15 min. and then allowed to warm slowly to room temperature. The solvent is removed completely in vacuo, the oily residue is taken up in 700 ml of glacial acetic acid, and the suspension is stirred at 70° C. for 4 h. After cooling, the solid is filtered off with suction, washed twice with 100 ml of glacial acetic acid each time, twice with 100 ml of ethanol each time, then dried in vacuo, and the crude product is recrystallised once from about 200 ml of dioxane. Yield: 84.8 g (182 mmol), 73%; purity according to NMR about 99.5%.

The following compounds can be obtained analogously:

| Ex. | Secondary amine | Product | Yield |
|---|---|---|---|
| 7 | S2 | | 64% |
| 8 | S3 | | 71% |

-continued
| Ex. | Secondary amine | Product | Yield |
|---|---|---|---|
| 9 | 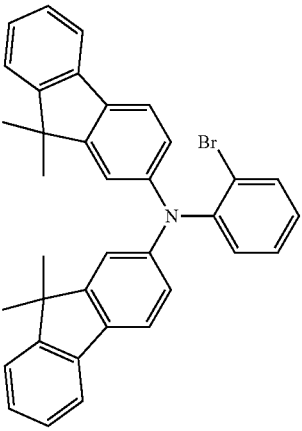 S4 | 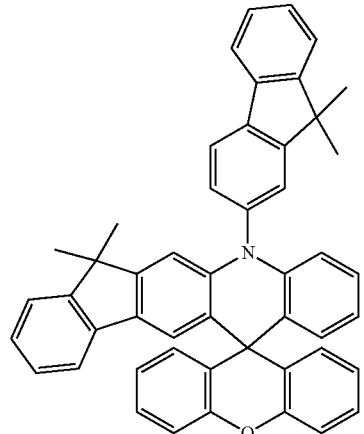 Recrystallisation three times from dioxane | 38% |
| 10 | 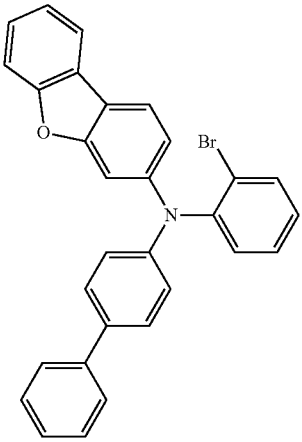 S5 | 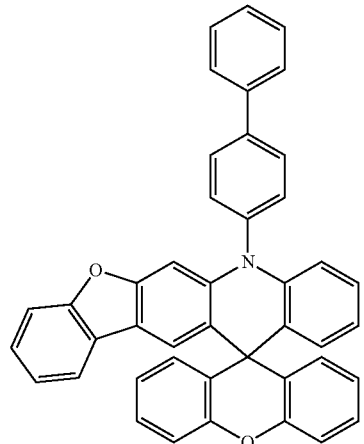 Recrystallisation five times from dioxane | 23% |
| 23 | 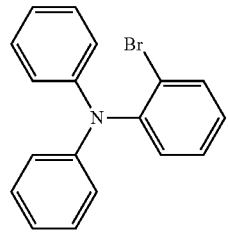 S6 | 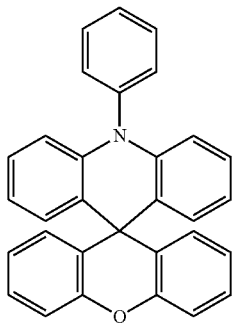 [SMILES: c1ccc(N2c3ccccc3C3(c4ccccc4Oc4ccccc43)c3ccccc32)cc1] | 76% |

-continued
| Ex. | Secondary amine | Product | Yield |
|---|---|---|---|
| 24 | 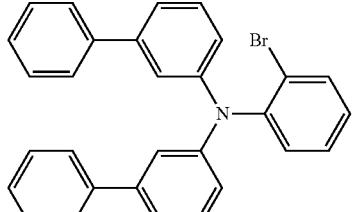<br>S7 | 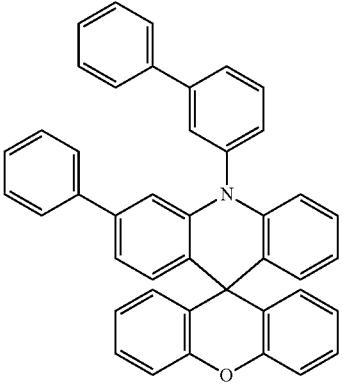 [SMILES: c1ccc(-c2cccc(N3c4ccccc4C4(c5ccccc5Oc5ccccc54)c4ccc(-c5ccccc5)cc43)c2)cc1] | 54% |
| 25 | 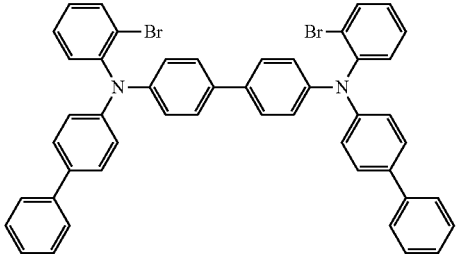 [SMILES: Brc1ccccc1N(c1ccc(-c2ccccc2)cc1)c1ccc(-c2ccc(N(c3ccc(-c4ccccc4)cc3)c3ccccc3Br)cc2)cc1]<br>S8 | 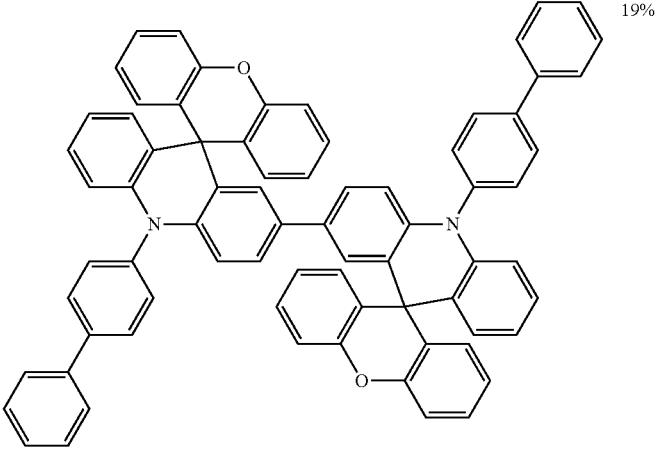 | 19% |
| 26 | 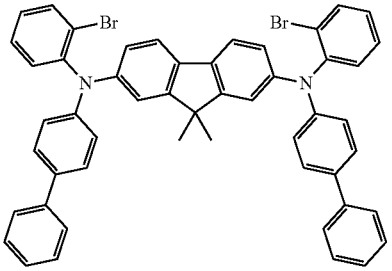 [SMILES: CC1(C)c2cc(N(c3ccc(-c4ccccc4)cc3)c3ccccc3Br)ccc2-c2ccc(N(c3ccc(-c4ccccc4)cc3)c3ccccc3Br)cc21]<br>S9 | 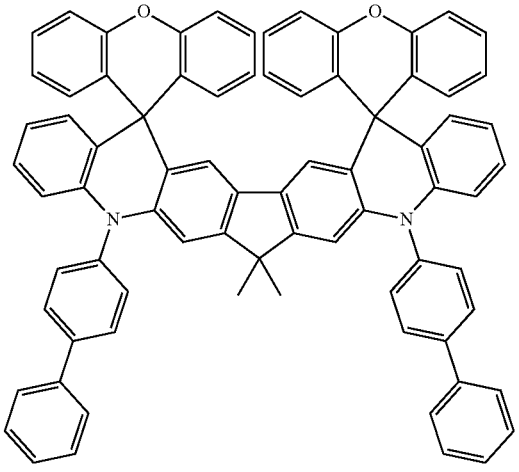 [SMILES: CC1(C)c2cc3c(cc2-c2cc4c(cc21)N(c1ccc(-c2ccccc2)cc1)c1ccccc1C41c2ccccc2Oc2ccccc21)C1(c2ccccc2Oc2ccccc21)c1ccccc1N3c1ccc(-c2ccccc2)cc1] | 26% |

-continued
| Ex. | Secondary amine | Product | Yield |
|---|---|---|---|
| 27 | 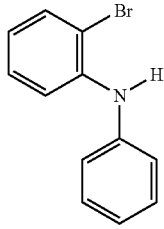 [SMILES: Brc1ccccc1Nc1ccccc1]<br>61613-22-7<br>Use of 500 mmol of n-BuLi | 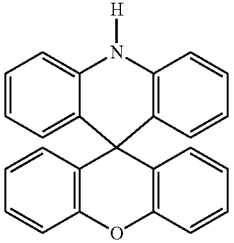 [SMILES: c1ccc2c(c1)Nc1ccccc1C21c2ccccc2Oc2ccccc21] | 48% |
| 28 | 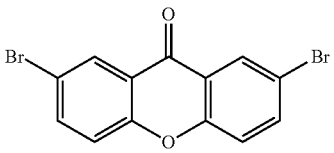 [SMILES: O=c1c2cc(Br)ccc2oc2ccc(Br)cc12]<br>40102-85-0<br>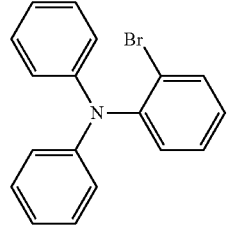 [SMILES: Brc1ccccc1N(c1ccccc1)c1ccccc1]<br>S6 | 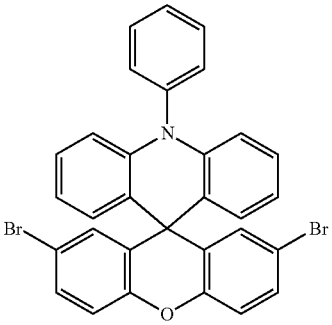 [SMILES: Brc1ccc2c(c1)C1(c3cc(Br)ccc3O2)c2ccccc2N(c2ccccc2)c2ccccc21] | 73% |
| 29 | 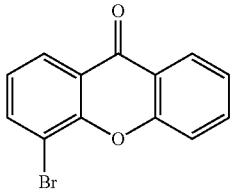 [SMILES: O=c1c2ccccc2oc2c(Br)cccc12]<br>861548-92-7<br>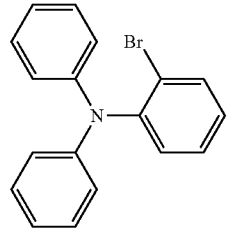 [SMILES: Brc1ccccc1N(c1ccccc1)c1ccccc1]<br>S6 | 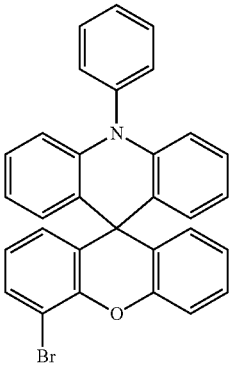 [SMILES: Brc1cccc2c1Oc1ccccc1C21c2ccccc2N(c2ccccc2)c2ccccc21] | 71% |

US 10,305,040 B2
-continued
| Ex. | Secondary amine | Product | Yield |
|---|---|---|---|
| 30 | 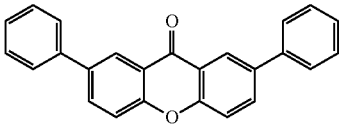 [SMILES: O=c1c2cc(-c3ccccc3)ccc2oc2ccc(-c3ccccc3)cc12] 1316277-14-1 <br> 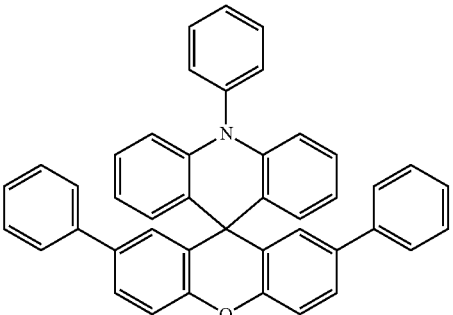 S6 | 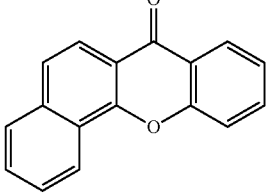 | 78% |
| 31 | 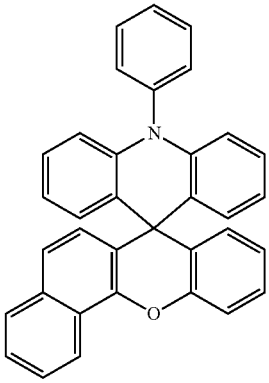 [SMILES: c1ccc(N2c3ccccc3C3(c4ccccc4Oc4c3ccc3ccccc43)c3ccccc32)cc1] 63154-69-8 <br> 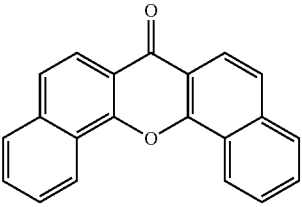 [SMILES: O=c1c2ccc3ccccc3c2oc2c1ccc1ccccc12] S6 | 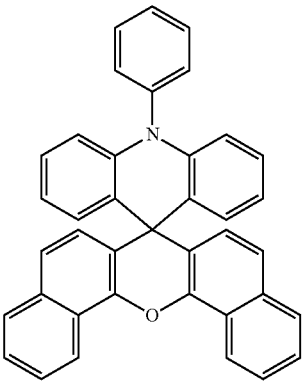 [SMILES: c1ccc(N2c3ccccc3C3(c4ccccc42)c2ccc4ccccc4c2Oc2c3ccc3ccccc23)cc1] | 72% |
| 32 | 3264-24-2 <br> S6 | | 76% |

-continued
| Ex. | Secondary amine | Product | Yield |
|---|---|---|---|
| 33 | 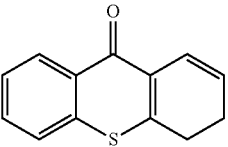 [SMILES: O=c1c2c(sc3ccccc13)CCC=C2]492-22-8<br>S6 | 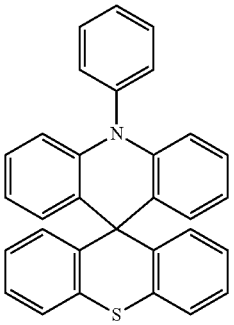 | 68% |
| 34 | 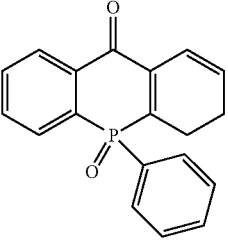 [SMILES: O=C1C2=C(CCC=C2)P(=O)(c2ccccc2)c2ccccc21]54086-38-3<br>S6 | 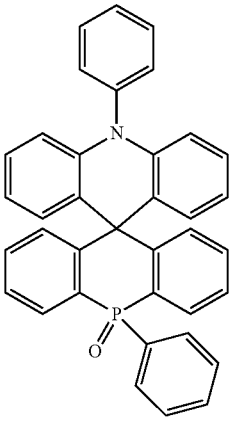 [SMILES: O=P1(c2ccccc2)c2ccccc2C2(c3ccccc3N(c3ccccc3)c3ccccc32)c2ccccc21] | 37% |
| 35 | 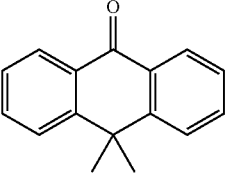 [SMILES: CC1(C)c2ccccc2C(=O)c2ccccc21]5447-86-9<br>S6 | 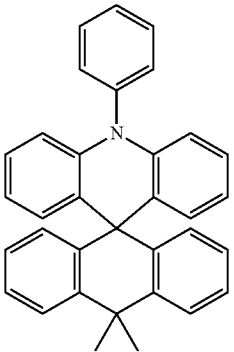 [SMILES: CC1(C)c2ccccc2C2(c3ccccc3N(c3ccccc3)c3ccccc32)c2ccccc21] | 53% |

| Ex. | Secondary amine | Product | Yield |
|---|---|---|---|
| 36 | 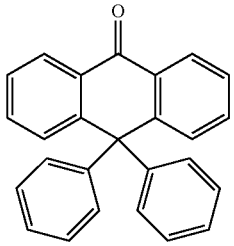 [SMILES: O=C1c2ccccc2C(c2ccccc2)(c2ccccc2)c2ccccc21] 3216-03-3 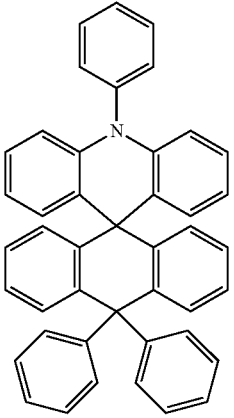 [SMILES: c1ccc(N2c3ccccc3C3(c4ccccc42)c2ccccc2C(c2ccccc2)(c2ccccc2)c2ccccc23)cc1] S6 | 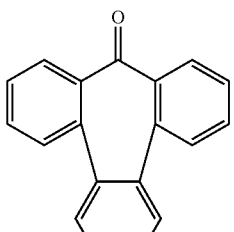 | 59% |
| 37 | 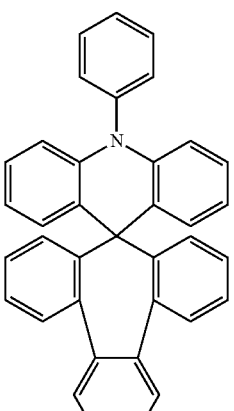 68089-73-6 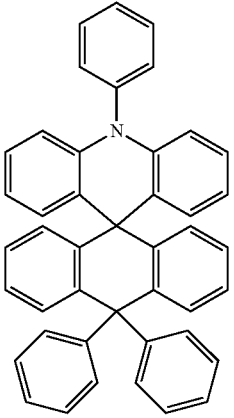 [SMILES: c1ccc(N2c3ccccc3C3(c4ccccc42)c2ccccc2C(c2ccccc2)(c2ccccc2)c2ccccc23)cc1] S6 | | 43% |

Example 11: 3,6-Dibromo-10-mesitylspiro[acridine-9(10H),9'-xanthene]

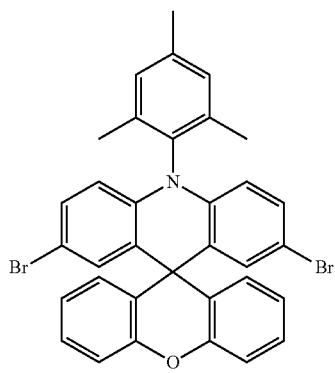 [SMILES: Cc1cc(C)c(N2c3ccc(Br)cc3C3(c4ccccc4Oc4ccccc43)c3cc(Br)ccc32)c(C)c1]

55.2 g (310 mmol) of NBS are added in portions to a solution, kept at 35° C., of 69.8 g (150 mmol) of 10-mesitylspiro[acridine-9(10H),9'-xanthene] in 1000 ml of dichloromethane, and the mixture is then stirred under reflux for 16 h. After cooling, the dichloromethane is removed in vacuo, the paste-like residue is taken up in 500 ml of methanol, stirred at 45° C. for a further 1 h, the crystalline solid is filtered off with suction, washed twice with 100 ml of methanol each time and dried in vacuo. Yield: 87.0 g (140 mmol), 93%; purity according to NMR about 99.5%.

The following compounds can be obtained analogously:

| Ex. | Starting material | Product | Yield |
| --- | --- | --- | --- |
| 12 | | | 86% |

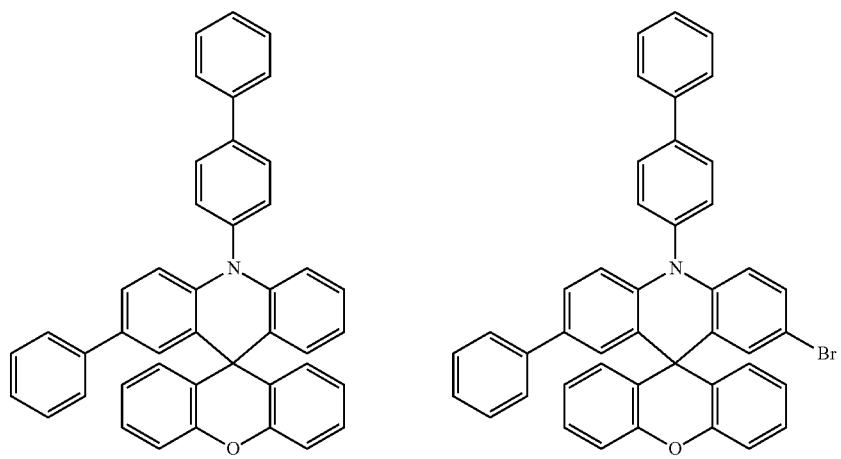

Only 1.05 equivalents of NBS are employed

| 13 | | | 73% |

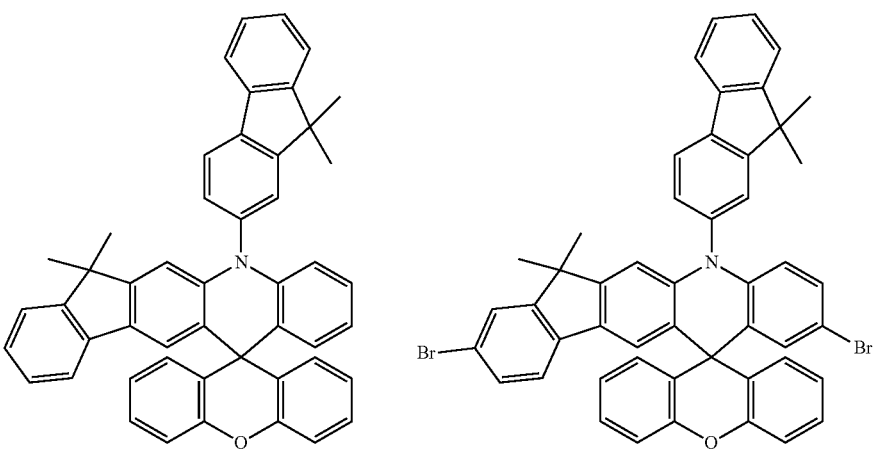

Recrystallisation of the crude product twice from dioxane

| Ex. | Starting material | Product | Yield |
|---|---|---|---|
| 38 | 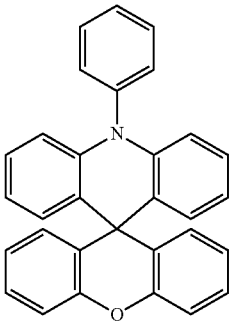 [SMILES: c1ccc(N2c3ccccc3C3(c4ccccc4Oc4ccccc43)c3ccccc32)cc1] | 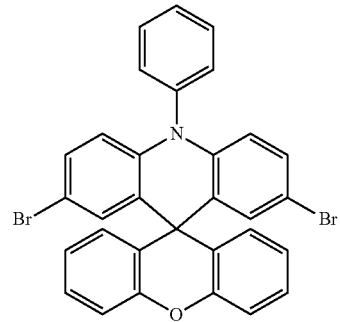 | 79% |
| 39 | 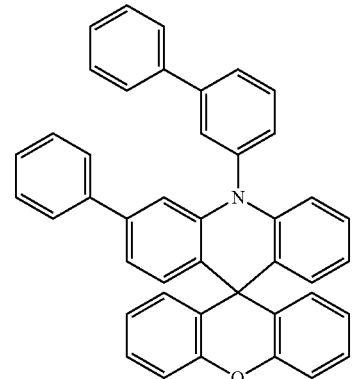 | 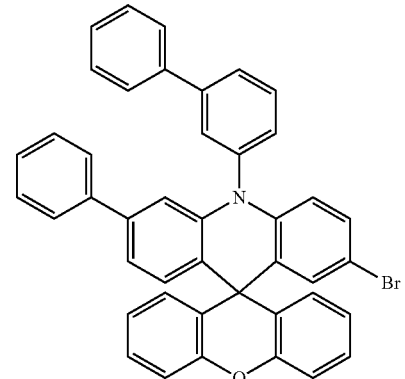<br>Only 1.05 equivalents of NBS are employed | 76% |
| 40 | 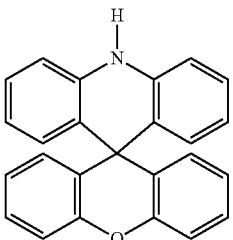 | 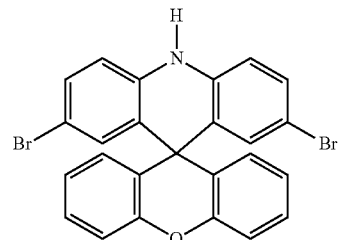 | 70% |
| 41 | 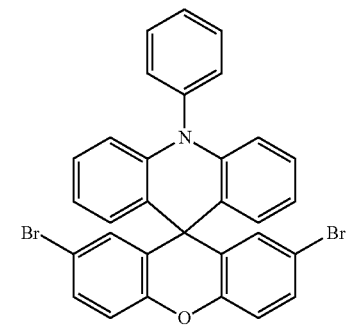 [SMILES: Brc1ccc2c(c1)C1(c3cc(Br)ccc3O2)c2ccccc2N(c2ccccc2)c2ccccc21] | 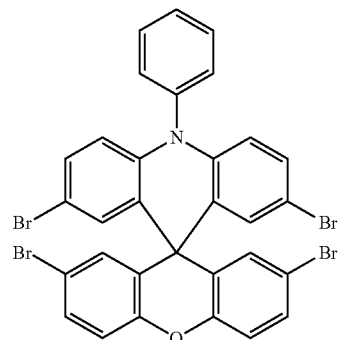 | 74% |

-continued

| Ex. | Starting material | Product | Yield |
|---|---|---|---|
| 42 | | | 68% |
| 43 | | | 76% |
| 44 | | | 73% |
| 45 | | | 75% |

| Ex. | Starting material | Product | Yield |
|---|---|---|---|
| 46 | 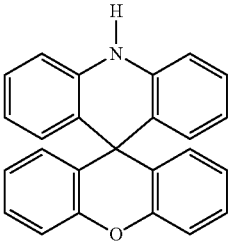 [SMILES: c1ccc2c(c1)Nc1ccccc1C21c2ccccc2Oc2ccccc21] | 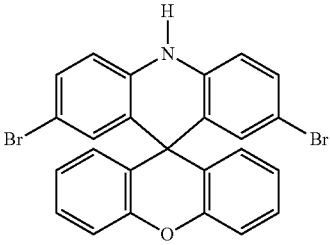 [SMILES: Brc1ccc2c(c1)C1(c3cc(Br)ccc3N2)c2ccccc2Oc2ccccc21] | 70% |
| 47 | 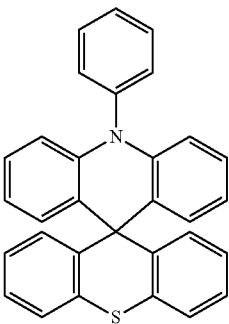 | 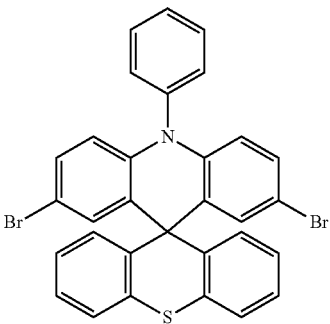 | 76% |
| 48 | 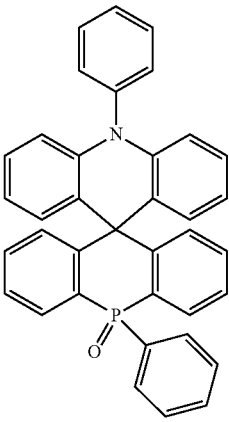 [SMILES: O=P1(c2ccccc2)c2ccccc2C2(c3ccccc3N(c3ccccc3)c3ccccc32)c2ccccc21] | 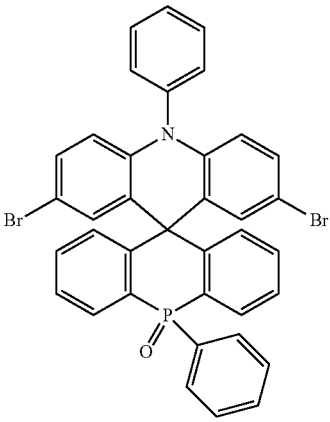 [SMILES: O=P1(c2ccccc2)c2ccccc2C2(c3cc(Br)ccc3N(c3ccccc3)c3ccc(Br)cc32)c2ccccc21] | 68% |
| 49 | 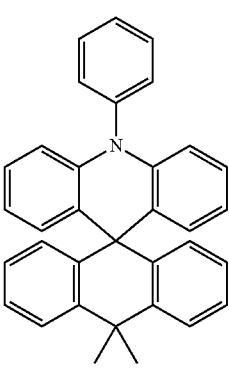 [SMILES: CC1(C)c2ccccc2C2(c3ccccc3N(c3ccccc3)c3ccccc32)c2ccccc21] | 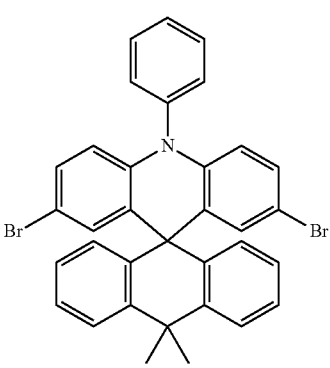 [SMILES: CC1(C)c2ccccc2C2(c3cc(Br)ccc3N(c3ccccc3)c3ccc(Br)cc32)c2ccccc21] | 80% |

| Ex. | Starting material | Product | Yield |
|---|---|---|---|
| 50 | | | 75% |
| 51 | | | 69% |

Example 14: 3,6-Diphenyl-10-mesitylspiro[acridine-9(10H),9'-xanthene]

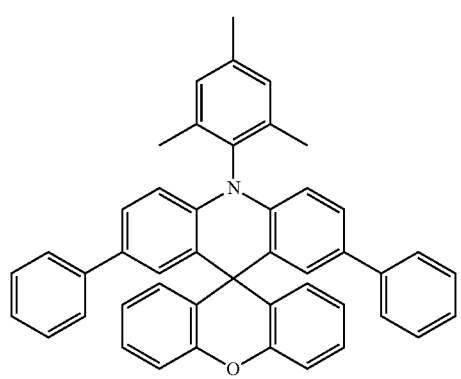 [SMILES: Cc1cc(C)c(N2c3ccc(-c4ccccc4)cc3C3(c4ccccc4Oc4ccccc43)c3cc(-c4ccccc4)ccc32)c(C)c1]

A mixture of 62.3 g (100 mmol) of 3,6-dibromo-10-mesitylspiro[acridine-9(10H),9'-xanthene], 30.5 g (250 mmol) of phenylboronic acid, 63.7 g (300 mmol) of tripotassium phosphate, 1.8 g (6 mmol) of tri-o-tolylphosphine, 225 mg (1 mmol) of palladium(II) acetate, 400 ml of toluene, 200 ml of dioxane and 400 ml of water is heated under reflux for 16 h. After cooling, the organic phase is separated off, washed once with 500 ml of water and once with 500 ml of saturated sodium chloride solution and then dried over magnesium sulfate. The desiccant is filtered off via a Celite bed, rinsed with toluene, the toluene is removed in vacuo, and the residue is recrystallised five times from dioxane (3 ml/g) with addition of ethanol (1-2 ml/g) at the boiling point. The further purification is carried out by fractional sublimation twice (p about $10^{-6}$ mbar, T=300-320° C.). Yield: 20.4 g (33 mmol), 33%; purity: >99.9% according to HPLC.

The following compounds can be obtained analogously:

| Ex. | Starting materials bromide/boronic acid | Product | Yield |
|---|---|---|---|
| 15 | 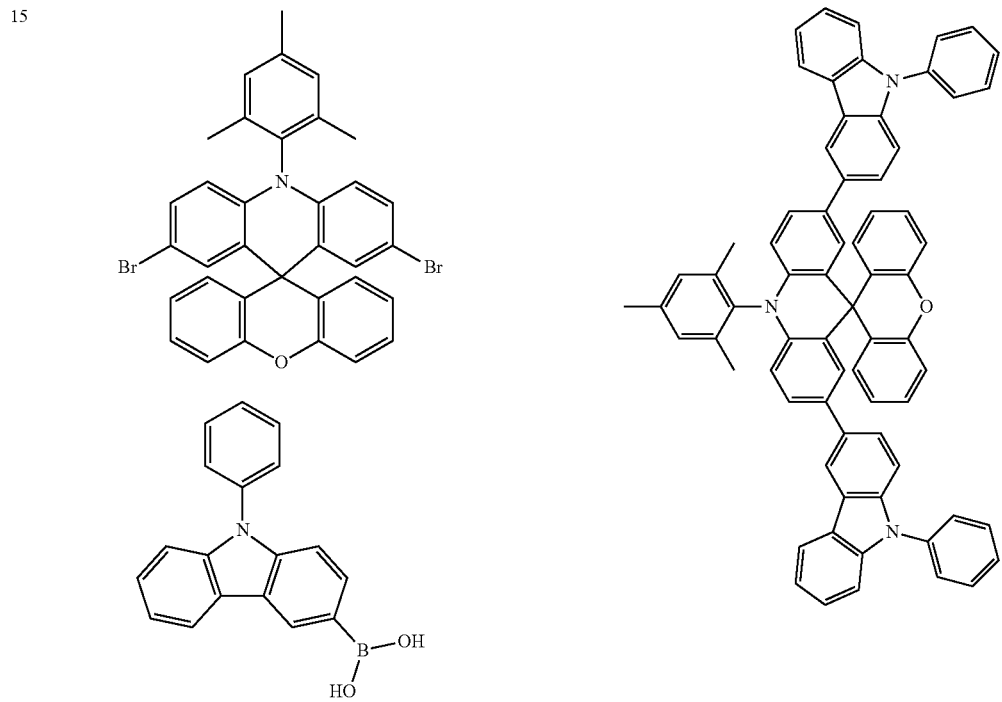 854952-58-2 | | 28% |
| 16 | 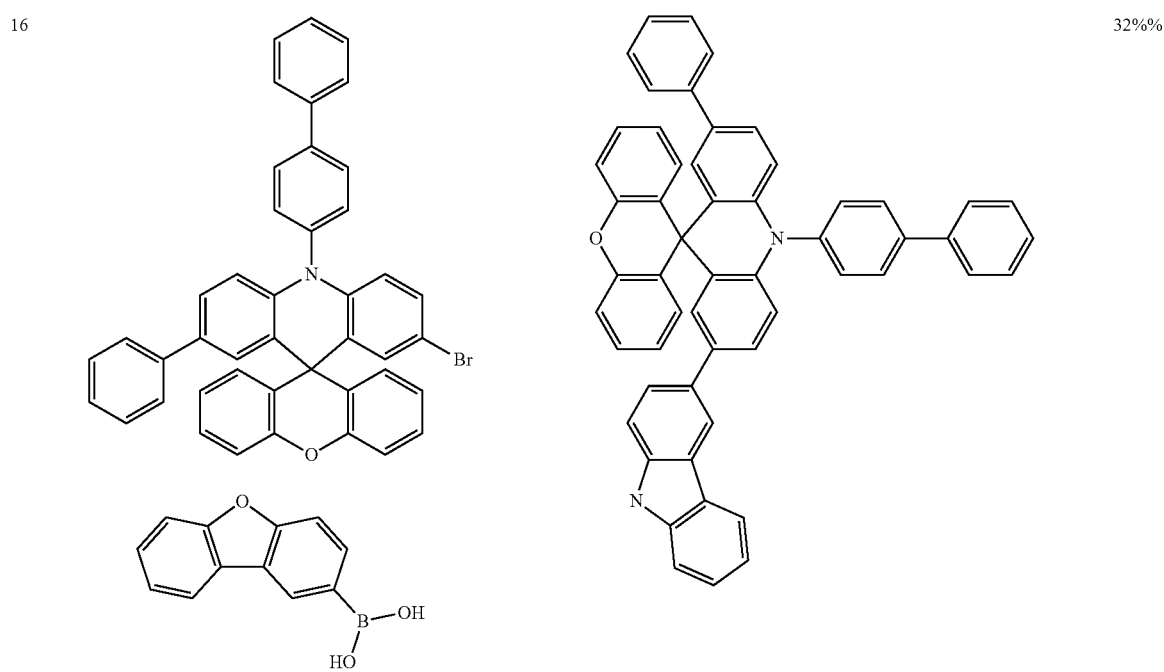 [402936-15-6] 125 mmol of boronic acid | | 32% |

-continued
| Ex. | Starting materials bromide/boronic acid | Product | Yield |
|---|---|---|---|
| 17 | 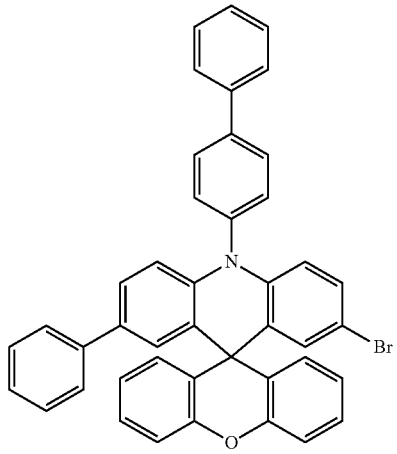 [SMILES: Brc1ccc2c(c1)C1(c3ccccc3Oc3ccccc31)c1cc(-c3ccccc3)ccc1N2c1ccc(-c2ccccc2)cc1] [854952-58-2] 125 mmol of boronic acid | 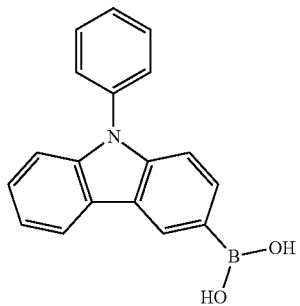 [SMILES: OB(O)c1ccc2c(c1)c1ccccc1n2-c1ccccc1] | 34% |
| 18 | 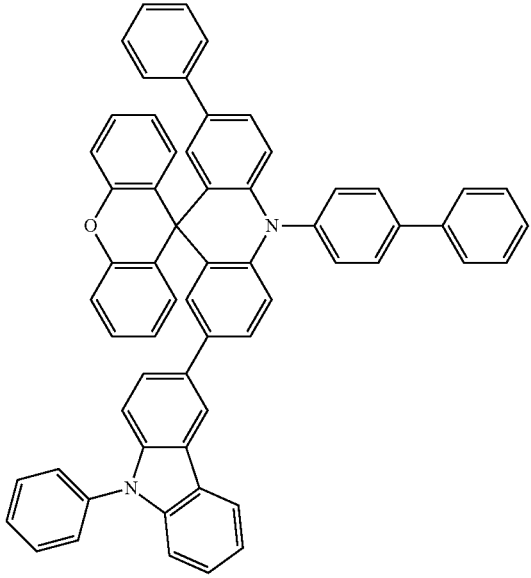 [SMILES: c1ccc(-c2ccc(N3c4ccc(-c5ccccc5)cc4C4(c5ccccc5Oc5ccccc54)c4cc(-c5ccc6c(c5)c5ccccc5n6-c5ccccc5)ccc43)cc2)cc1] 98-80-6 | 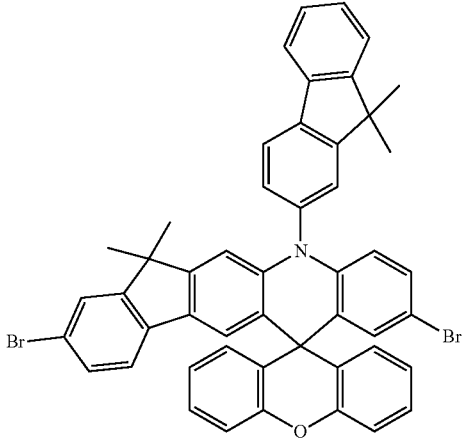 [SMILES: CC1(C)c2ccccc2-c2ccc(N3c4ccc(Br)cc4C4(c5ccccc5Oc5ccccc54)c4cc5c(cc43)C(C)(C)c3cc(Br)ccc3-5)cc21] | 30% |

-continued
| Ex. | Starting materials bromide/boronic acid | Product | Yield |
|---|---|---|---|
| 52 | 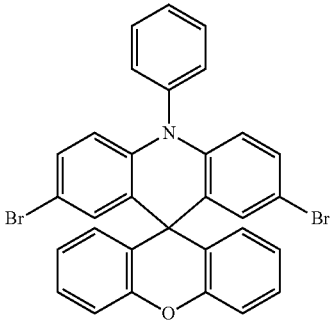 [SMILES: Brc1ccc2c(c1)C1(c3ccccc3Oc3ccccc31)c1cc(Br)ccc1N2c1ccccc1] 4688-76-0 | 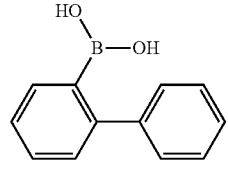 [SMILES: OB(O)c1ccccc1-c1ccccc1] | 33% |
| 53 | 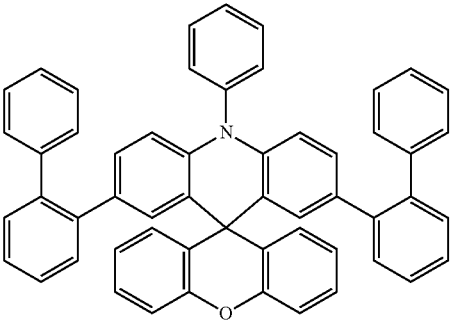 [SMILES: c1ccc(-c2ccccc2-c2ccc3c(c2)C2(c4ccccc4Oc4ccccc42)c2cc(-c4ccccc4-c4ccccc4)ccc2N3c2ccccc2)cc1] 201802-67-7 | 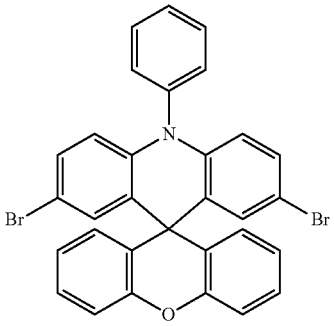 | 29% |

| Ex. | Starting materials bromide/boronic acid | Product | Yield |
|---|---|---|---|
| 54 | 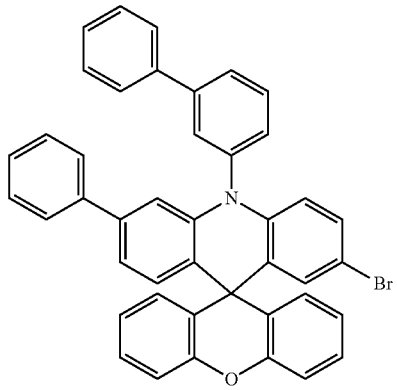 [SMILES: Brc1ccc2c(c1)C1(c3ccccc3Oc3ccccc31)c1ccc(-c3ccccc3)cc1N2c1cccc(-c2ccccc2)c1] 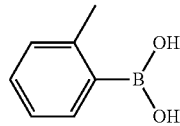 16419-60-6 125 mmol of boronic acid | 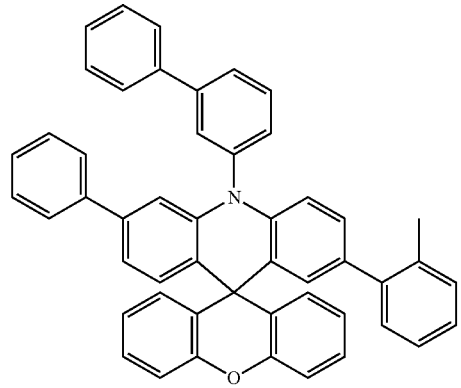 [SMILES: Cc1ccccc1-c1ccc2c(c1)C1(c3ccccc3Oc3ccccc31)c1ccc(-c3ccccc3)cc1N2c1cccc(-c2ccccc2)c1] | 27% |
| 55 | 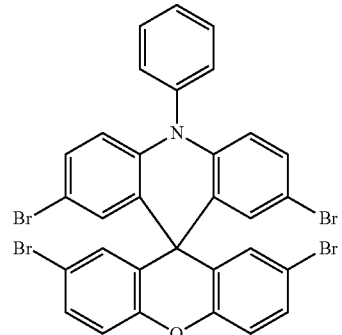 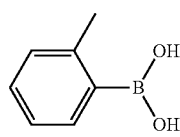 16419-60-6 500 mmol of boronic acid | 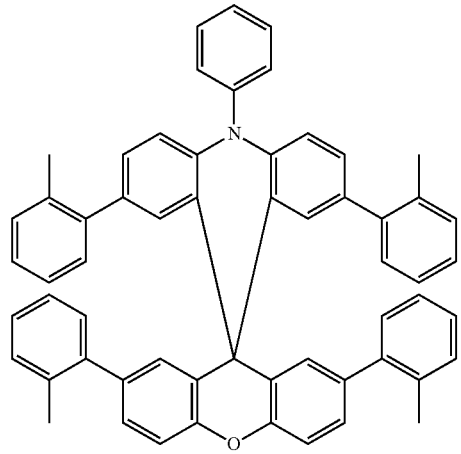 [SMILES: Cc1ccccc1-c1ccc2c(c1)C1(c3cc(-c4ccccc4C)ccc3O2)c2cc(-c3ccccc3C)ccc2N(c2ccccc2)c2ccc(-c3ccccc3C)cc21] | 43% |

| Ex. | Starting materials bromide/boronic acid | Product | Yield |
|---|---|---|---|
| 56 | 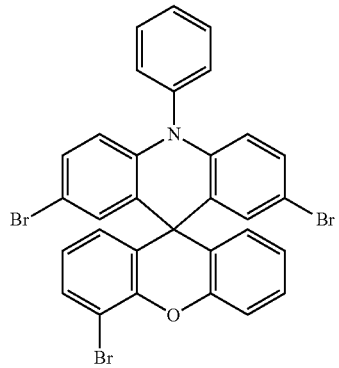 [SMILES: Brc1ccc2c(c1)C1(c3ccccc3Oc3c(Br)cccc31)c1cc(Br)ccc1N2c1ccccc1]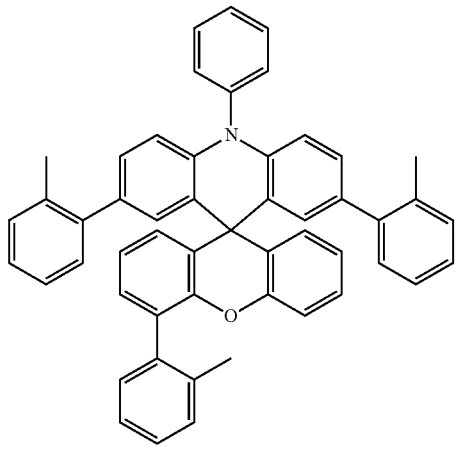 [SMILES: Cc1ccccc1-c1ccc2c(c1)C1(c3ccccc3Oc3c(-c4ccccc4C)cccc31)c1cc(-c3ccccc3C)ccc1N2c1ccccc1]16419-60-6<br>375 mmol of boronic acid | | 30% |
| 57 | 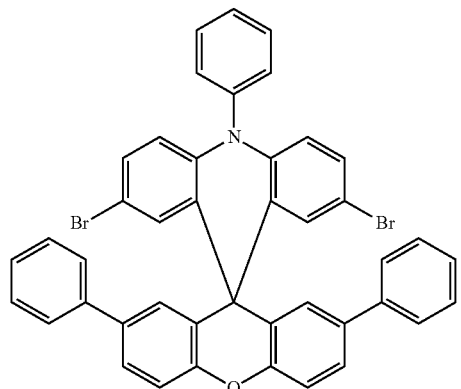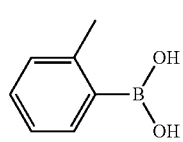16419-60-6 | 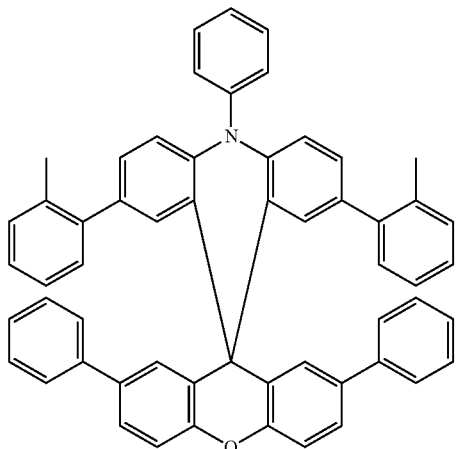 | 41% |

-continued
| Ex. | Starting materials bromide/boronic acid | Product | Yield |
|---|---|---|---|
| 58 | 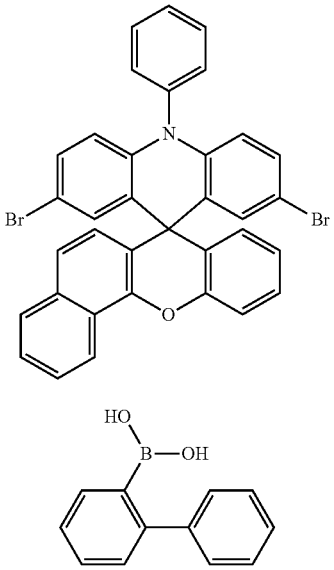 4688-76-0 | 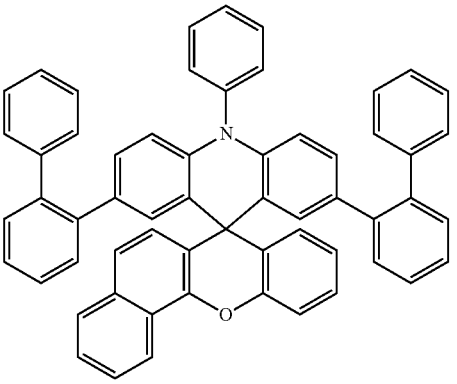 [SMILES: c1ccc(-c2ccccc2-c2ccc3c(c2)C2(c4ccccc4Oc4c2ccc2ccccc42)c2cc(-c4ccccc4-c4ccccc4)ccc2N3c2ccccc2)cc1] | 32% |
| 59 | 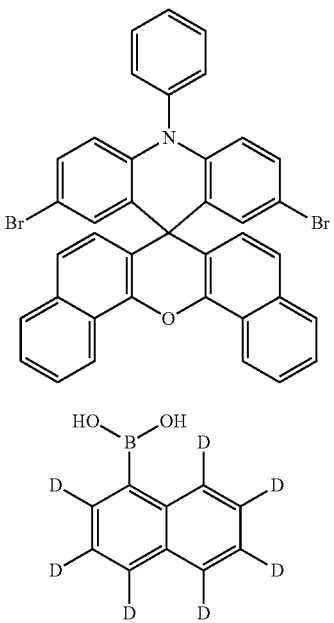 1000869-26-0 | 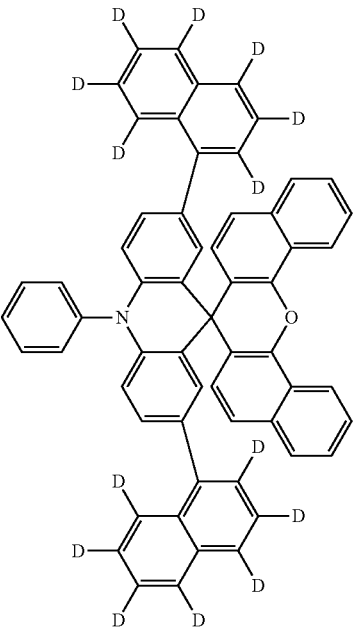 [SMILES: [2H]c1c([2H])c([2H])c2c(-c3ccc4c(c3)C3(c5cc(-c6c([2H])c([2H])c([2H])c7c([2H])c([2H])c([2H])c([2H])c67)ccc5N4c4ccccc4)c4ccc5ccccc5c4Oc4c3ccc3ccccc43)c([2H])c([2H])c([2H])c2c1[2H]] | 41% |

-continued
| Ex. | Starting materials bromide/boronic acid | Product | Yield |
|---|---|---|---|
| 60 | 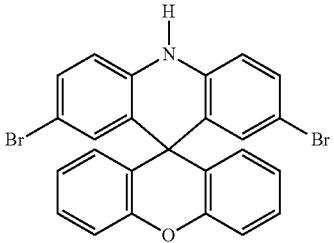 98-80-6 | 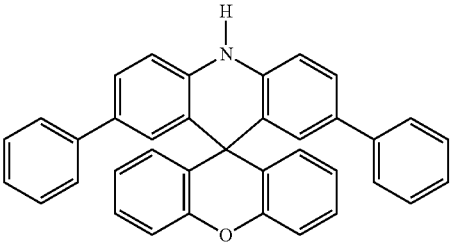 [SMILES: c1ccc(-c2ccc3c(c2)C2(c4cc(-c5ccccc5)ccc4N3)c3ccccc3Oc3ccccc32)cc1] No sublimination, building block is reacted further! | 74% |
| 61 | 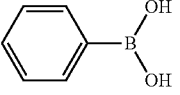 16419-60-6 | 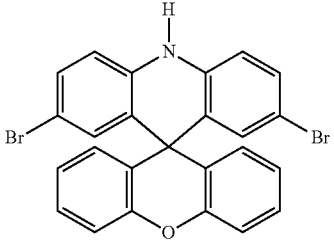 [SMILES: Brc1ccc2c(c1)C1(c3cc(Br)ccc3N2)c2ccccc2Oc2ccccc21] No sublimination, building block is reacted further! | 70% |
| 62 | 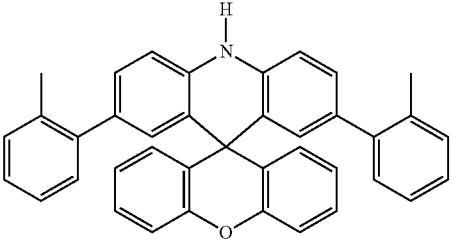 [SMILES: Cc1ccccc1-c1ccc2c(c1)C1(c3cc(-c4ccccc4C)ccc3N2)c2ccccc2Oc2ccccc21] 4688-76-0 | 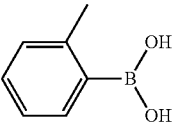 No sublimination, building block is reacted further! | 66% |

-continued
| Ex. | Starting materials bromide/boronic acid | Product | Yield |
|---|---|---|---|
| 63 | 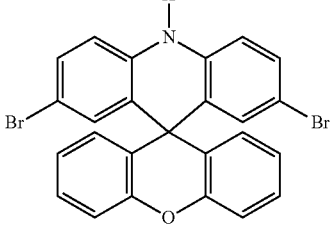 5122-95-2 | 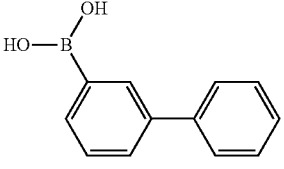 No sublimination, building block is reacted further! | 63% |
| 64 | 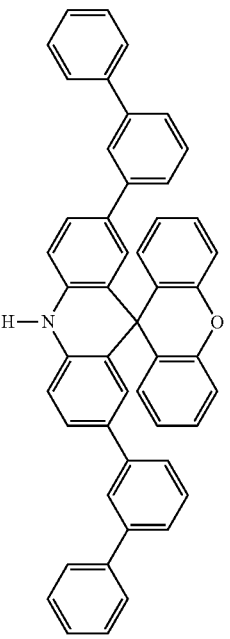 [SMILES: c1ccc(-c2cccc(-c3ccc4c(c3)C3(c5cc(-c6cccc(-c7ccccc7)c6)ccc5N4)c4ccccc4Oc4ccccc43)c2)cc1]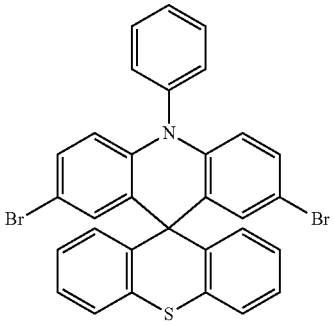 16419-60-6 | 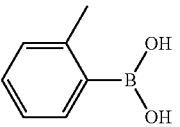 | 40% |

-continued
| Ex. | Starting materials bromide/boronic acid | Product | Yield |
|---|---|---|---|
| 65 | 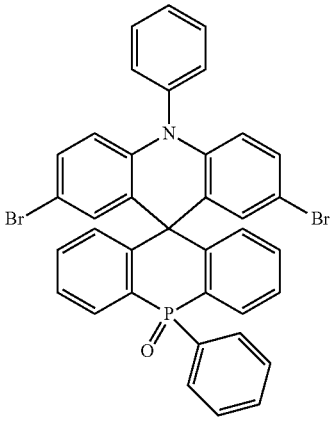 [SMILES: O=P1(c2ccccc2)c2ccccc2C2(c3cc(Br)ccc3N(c3ccccc3)c3ccc(Br)cc32)c2ccccc21] 16419-60-6 | 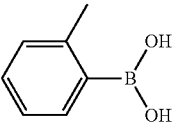 | 36% |
| 66 | 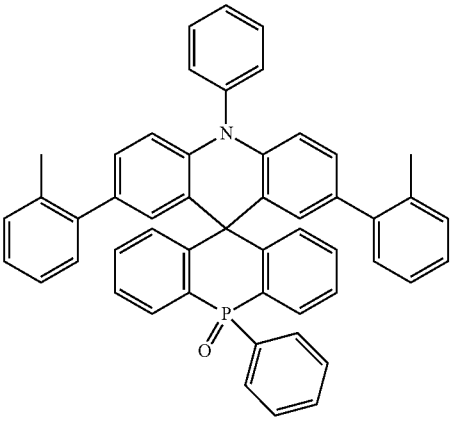 [SMILES: Cc1ccccc1-c1ccc2c(c1)C1(c3cc(-c4ccccc4C)ccc3N2c2ccccc2)c2ccccc2P(=O)(c2ccccc2)c2ccccc21] 4688-76-0 | 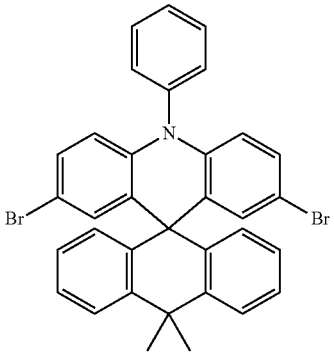 [SMILES: CC1(C)c2ccccc2C2(c3cc(Br)ccc3N(c3ccccc3)c3ccc(Br)cc32)c2ccccc21] | 31% |

US 10,305,040 B2
117                                                                                 118
-continued
| Ex. | Starting materials bromide/boronic acid | Product | Yield |
|---|---|---|---|
| 67 | 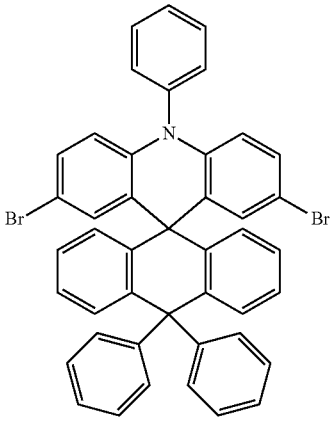 [SMILES: Brc1ccc2c(c1)C1(c3cc(Br)ccc3N2c2ccccc2)c2ccccc2C(c2ccccc2)(c2ccccc2)c2ccccc21] 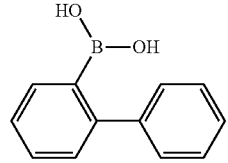 [SMILES: OB(O)c1ccccc1-c1ccccc1] 4688-76-0 | 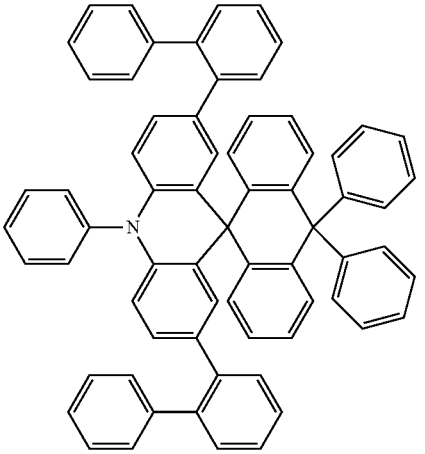 [SMILES: c1ccc(-c2ccccc2-c2ccc3c(c2)C2(c4cc(-c5ccccc5-c5ccccc5)ccc4N3c3ccccc3)c3ccccc3C(c3ccccc3)(c3ccccc3)c3ccccc32)cc1] | 27% |
| 68 | 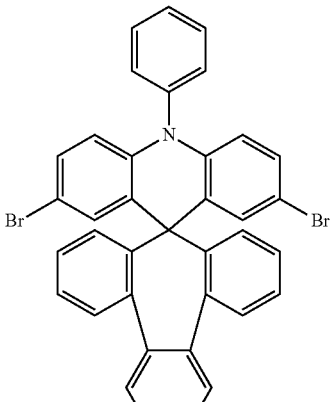 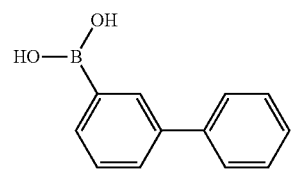 5122-95-2 | 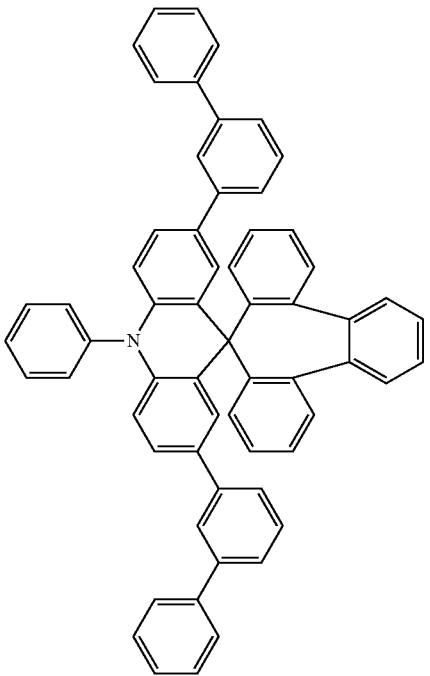 [SMILES: c1ccc(-c2cccc(-c3ccc4c(c3)C3(c5ccccc5-c5ccccc5-c5ccccc53)c3cc(-c5cccc(-c6ccccc6)c5)ccc3N4c3ccccc3)c2)cc1] | 33% |

-continued
| Ex. | Starting materials bromide/boronic acid | Product | Yield |
|---|---|---|---|
| 69 | 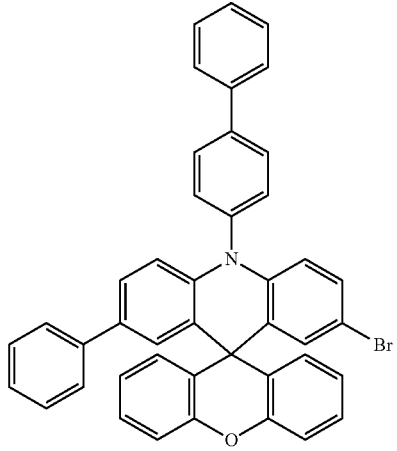<br>98-80-6<br>125 mmol of boronic acid | 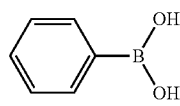 | 56% |
| 70 | 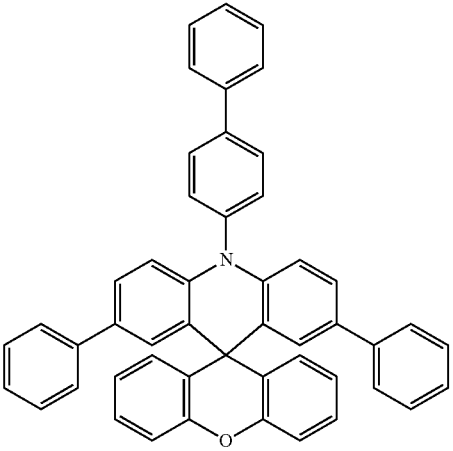 [SMILES: c1ccc(-c2ccc(N3c4ccc(-c5ccccc5)cc4C4(c5ccccc5Oc5ccccc54)c4cc(-c5ccccc5)ccc43)cc2)cc1]<br>16419-60-6<br>125 mmol of boronic acid | 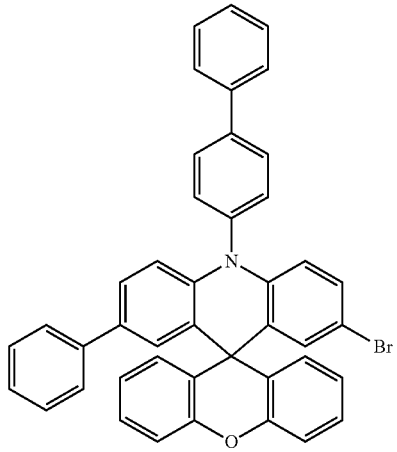 | 48% |

-continued
| Ex. | Starting materials bromide/boronic acid | Product | Yield |
|---|---|---|---|
| 71 | 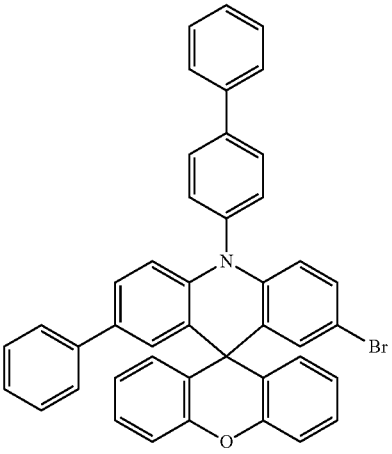<br>823-96-1 | 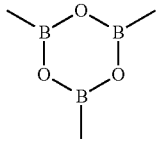 | 47% |
| 72 | 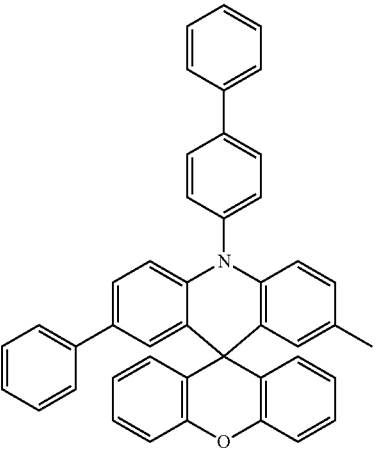 [SMILES: Cc1ccc2c(c1)C1(c3ccccc3Oc3ccccc31)c1cc(-c3ccccc3)ccc1N2c1ccc(-c2ccccc2)cc1]<br>4688-76-0<br>125 mmol of boronic acid | 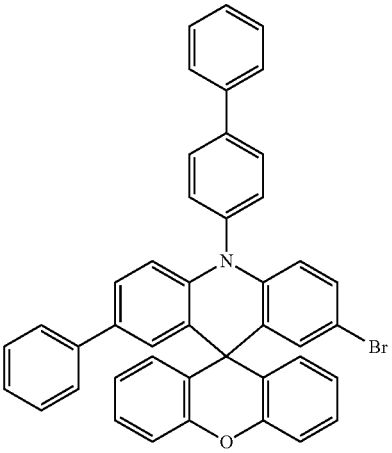 | 38% |

-continued
| Ex. | Starting materials bromide/boronic acid | Product | Yield |
|---|---|---|---|
| 73 | 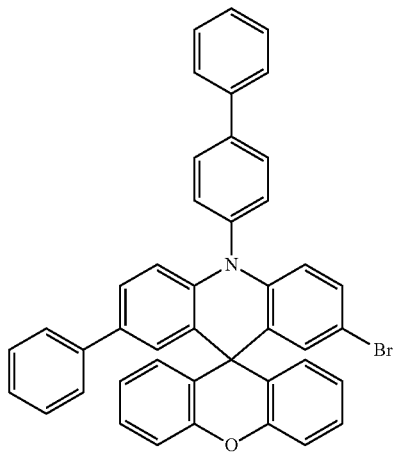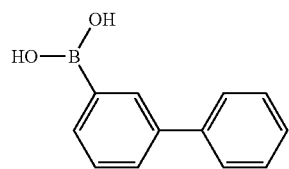 [SMILES: OB(O)c1cccc(-c2ccccc2)c1]5122-95-2<br>125 mmol of boronic acid | 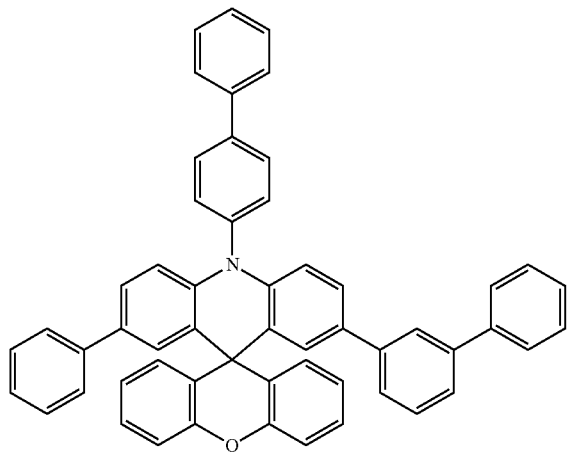 [SMILES: c1ccc(-c2ccc(N3c4ccc(-c5ccccc5)cc4C4(c5ccccc5Oc5ccccc54)c4cc(-c5cccc(-c6ccccc6)c5)ccc43)cc2)cc1] | 40% |
| 74 | 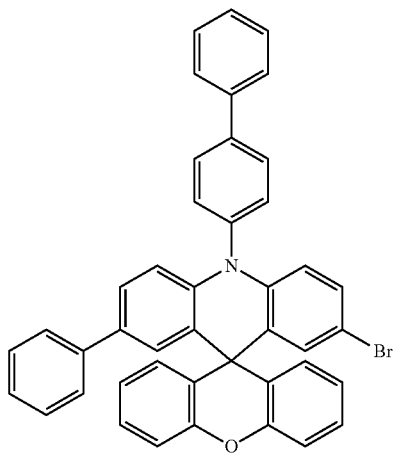 | 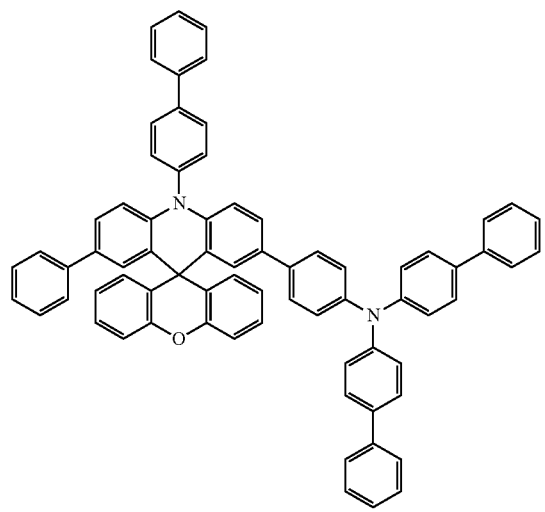 [SMILES: c1ccc(-c2ccc(N(c3ccc(-c4ccccc4)cc3)c3ccc(-c4ccc5c(c4)C4(c6ccccc6Oc6ccccc64)c4cc(-c6ccccc6)ccc4N5c4ccc(-c5ccccc5)cc4)cc3)cc2)cc1] | 45% |

| Ex. | Starting materials bromide/boronic acid | Product | Yield |
|---|---|---|---|
| | 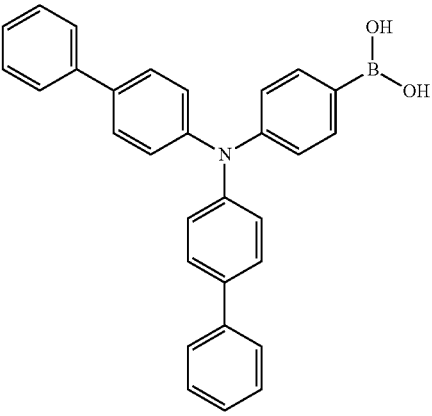 [SMILES: OB(O)c1ccc(N(c2ccc(-c3ccccc3)cc2)c2ccc(-c3ccccc3)cc2)cc1]<br>943836-24-6<br>125 mmol of boronic acid | | |
| 75 | 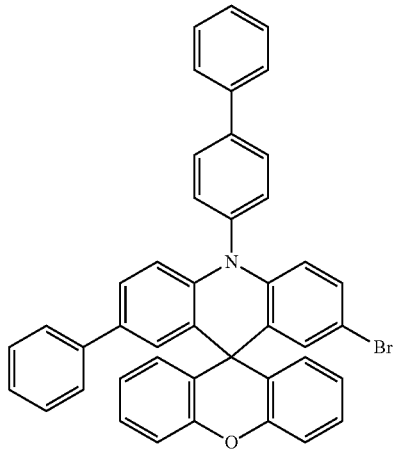 [SMILES: Brc1ccc2c(c1)C1(c3ccccc3Oc3ccccc31)c1cc(-c3ccccc3)ccc1N2c1ccc(-c2ccccc2)cc1]<br>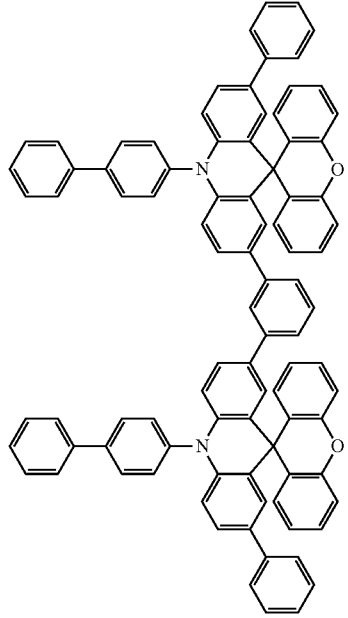 [SMILES: c1ccc(-c2ccc(N3c4ccc(-c5ccccc5)cc4C4(c5ccccc5Oc5ccccc54)c4cc(-c5cccc(-c6ccc7c(c6)C6(c8ccccc8Oc8ccccc86)c6cc(-c8ccccc8)ccc6N7c6ccc(-c7ccccc7)cc6)c5)ccc43)cc2)cc1]<br>4612-28-6<br>45 mmol of boronic acid | | 32% |

127 128
-continued
| Ex. | Starting materials bromide/boronic acid | Product | Yield |
|---|---|---|---|
| 76 | 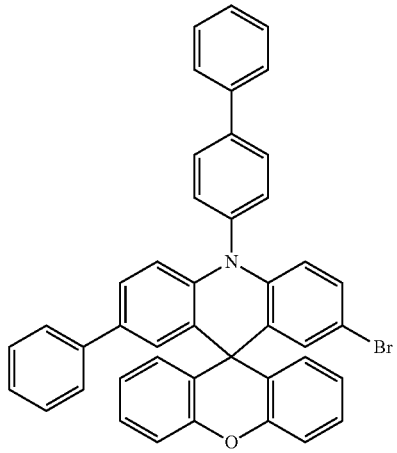 [SMILES: Brc1ccc2c(c1)C1(c3ccccc3Oc3ccccc31)c1cc(-c3ccccc3)ccc1N2c1ccc(-c2ccccc2)cc1] | 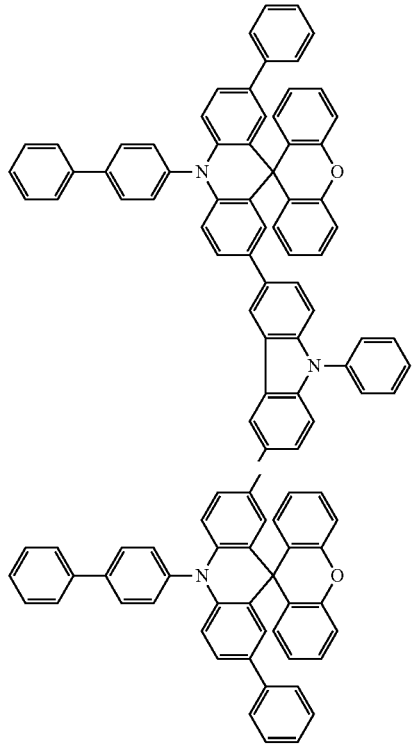 | 33% |
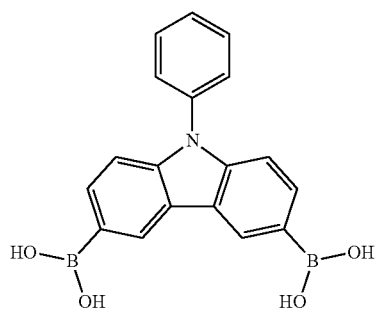 [SMILES: OB(O)c1ccc2c(c1)c1cc(B(O)O)ccc1n2-c1ccccc1]
1135916-40-3
45 mmol of boronic acid

| Ex. | Starting materials bromide/boronic acid | Product | Yield |
|---|---|---|---|
| 77 | 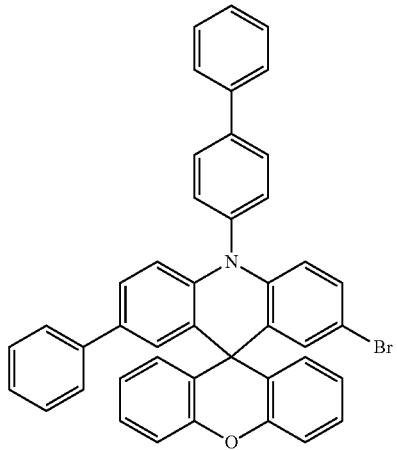 [SMILES: Brc1ccc2c(c1)C1(c3ccccc3Oc3ccccc31)c1cc(-c3ccccc3)ccc1N2c1ccc(-c2ccccc2)cc1]<br>100 mmol<br>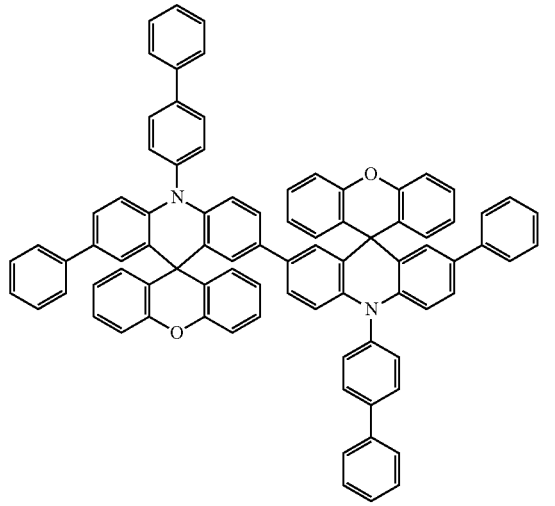 [SMILES: c1ccc(-c2ccc(N3c4ccc(-c5ccccc5)cc4C4(c5ccccc5Oc5ccccc54)c4cc(-c5ccc6c(c5)C5(c7ccccc7Oc7ccccc75)c5cc(-c7ccccc7)ccc5N6c5ccc(-c6ccccc6)cc5)ccc43)cc2)cc1]<br>110 mmol | 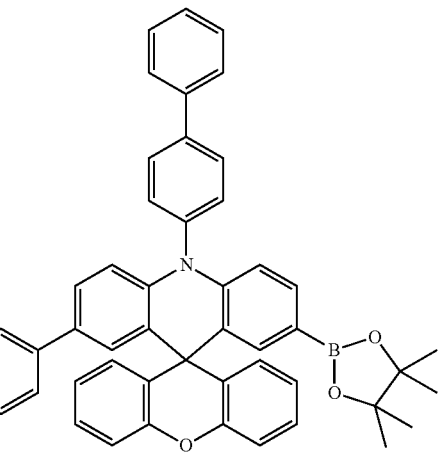 | 41% |
| 78 | 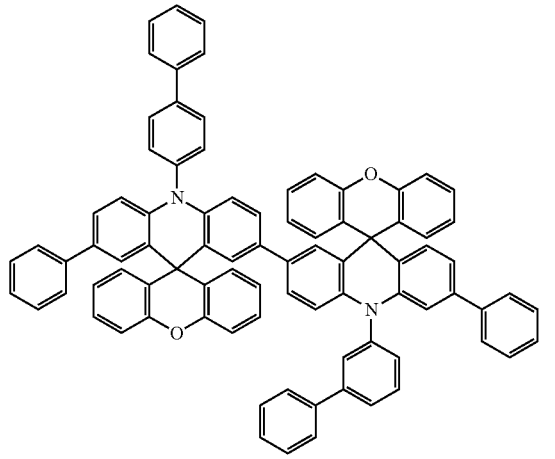 [SMILES: c1ccc(-c2ccc(N3c4ccc(-c5ccccc5)cc4C4(c5ccccc5Oc5ccccc54)c4cc(-c5ccc6c(c5)C5(c7ccccc7Oc7ccccc75)c5ccc(-c7ccccc7)cc5N6c5cccc(-c6ccccc6)c5)ccc43)cc2)cc1]<br>100 mmol | | 39% |

-continued
| Ex. | Starting materials bromide/boronic acid | Product | Yield |
|---|---|---|---|
| | 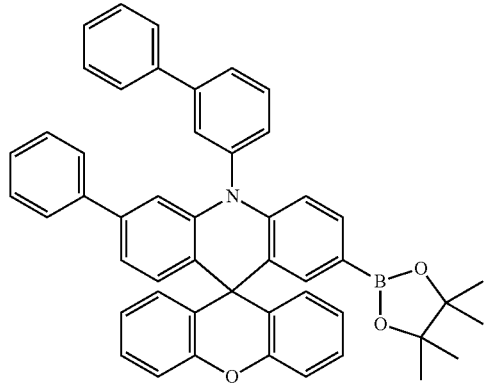 [SMILES: CC1(C)OB(c2ccc3c(c2)C2(c4ccccc4Oc4ccccc42)c2ccc(-c4ccccc4)cc2N3c2cccc(-c3ccccc3)c2)OC1(C)C]<br>110 mmol | | |
| 79 | 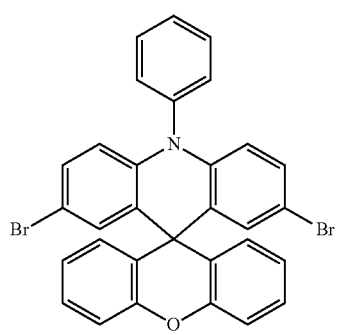 [SMILES: Brc1ccc2c(c1)C1(c3ccccc3Oc3ccccc31)c1cc(Br)ccc1N2c1ccccc1] | 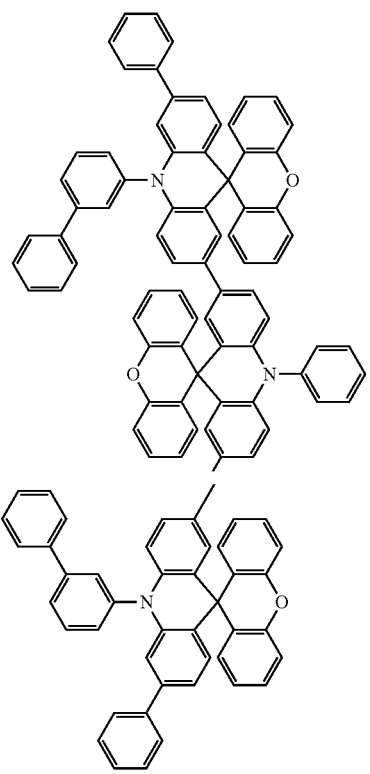<br>Comp. is heated in a high vacuum in order to remove solvent residues | 33% |

| Ex. | Starting materials bromide/boronic acid | Product | Yield |
|---|---|---|---|
| 80 | 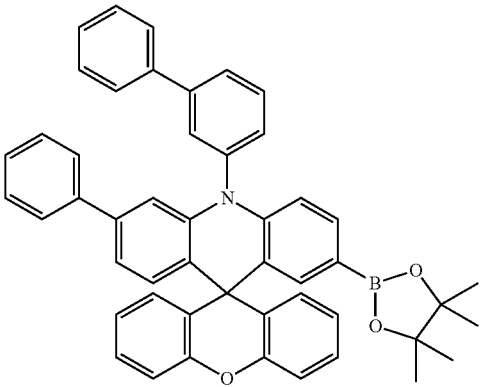 [SMILES: CC1(C)OB(c2ccc3c(c2)C2(c4ccccc4Oc4ccccc42)c2ccc(-c4ccccc4)cc2N3c2cccc(-c3ccccc3)c2)OC1(C)C]<br>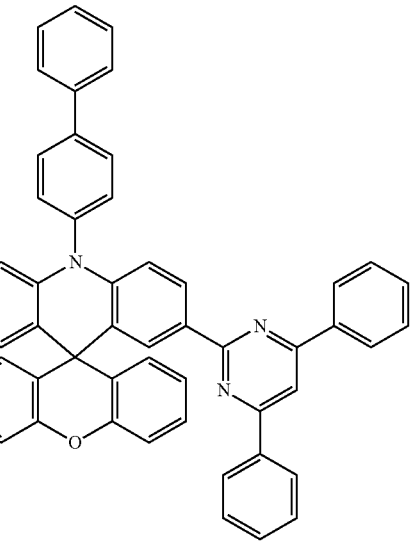<br>100 mmol<br><br>2915-16-4<br>130 mmol | 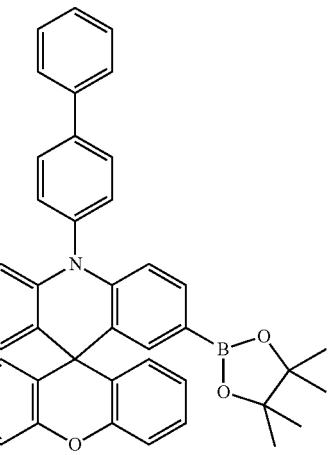 | 43% |

| Ex. | Starting materials bromide/boronic acid | Product | Yield |
|---|---|---|---|
| 81 | 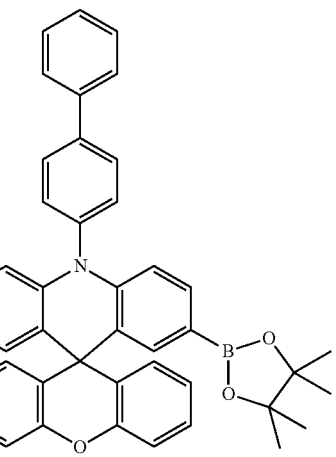 100 mmol 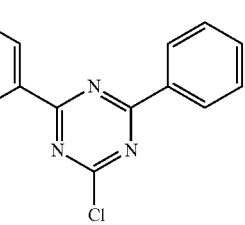 3842-55-5 130 mmol | 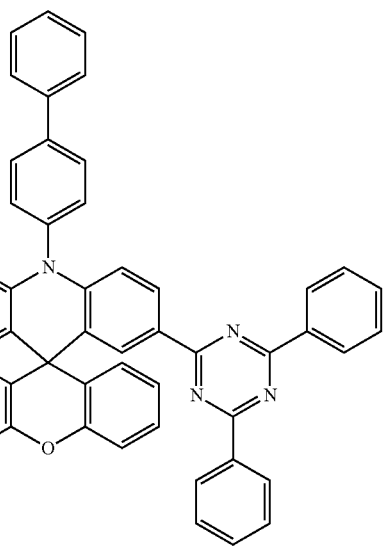 | 40% |
| 82 | 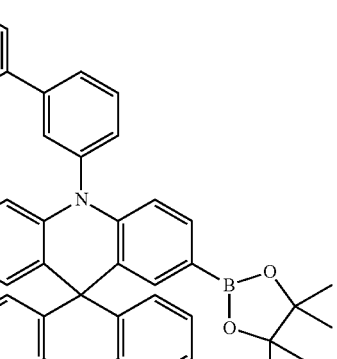 100 mmol 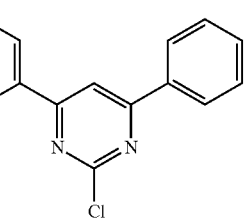 2915-16-4 130 mmol | 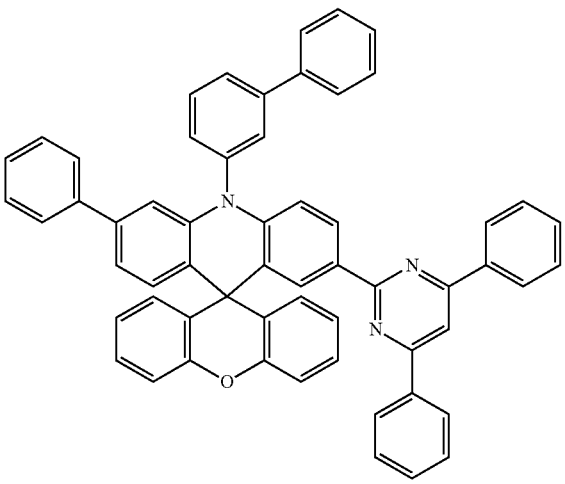 [SMILES: c1ccc(-c2cccc(N3c4cc(-c5ccccc5)ccc4C4(c5ccccc5Oc5ccccc54)c4cc(-c5nc(-c6ccccc6)cc(-c6ccccc6)n5)ccc43)c2)cc1] | 36% |

-continued
| Ex. | Starting materials bromide/boronic acid | Product | Yield |
|---|---|---|---|
| 83 | 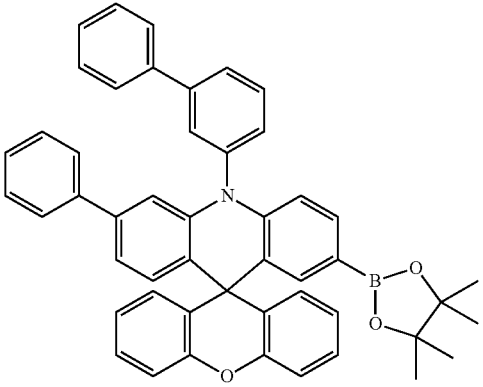 [SMILES: CC1(C)OB(c2ccc3c(c2)C2(c4ccccc4Oc4ccccc42)c2ccc(-c4ccccc4)cc2N3c2cccc(-c3ccccc3)c2)OC1(C)C] 3842-55-5 130 mmol | 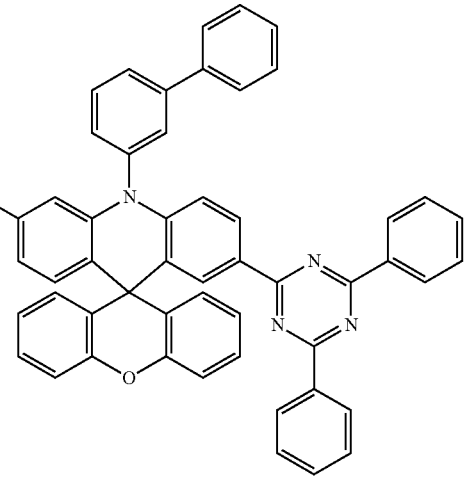 | 33% |
| 84 | 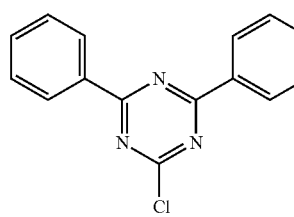 100 mmol 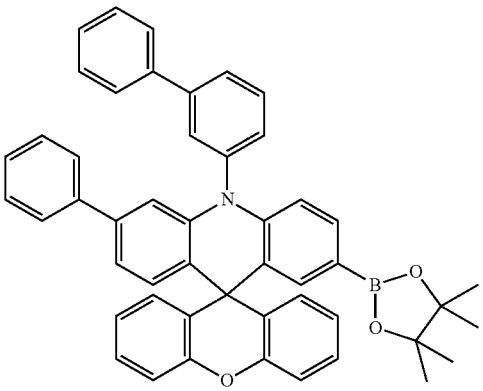 [SMILES: CC1(C)OB(c2ccc3c(c2)C2(c4ccccc4Oc4ccccc42)c2ccc(-c4ccccc4)cc2N3c2cccc(-c3ccccc3)c2)OC1(C)C] 864377-31-1 130 mmol | 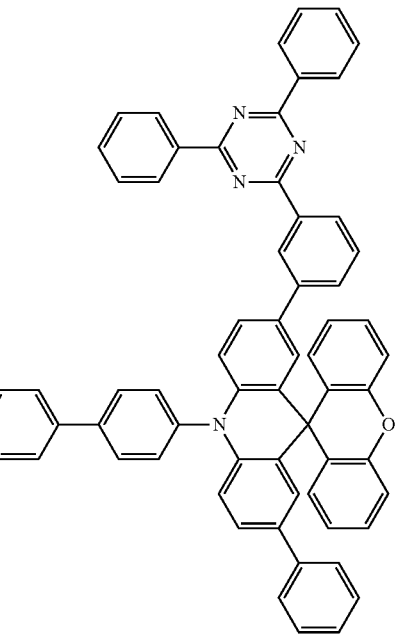 | 34% |

| Ex. | Starting materials bromide/boronic acid | Product | Yield |
|---|---|---|---|
| 85 | 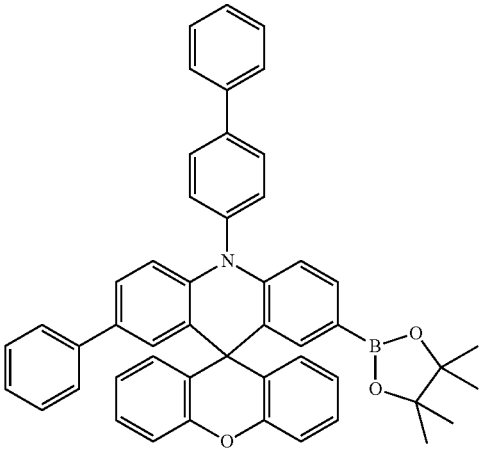 [SMILES: CC1(C)OB(c2ccc3c(c2)C2(c4ccccc4Oc4ccccc42)c2cc(-c4ccccc4)ccc2N3c2ccc(-c3ccccc3)cc2)OC1(C)C]<br>100 mmol<br>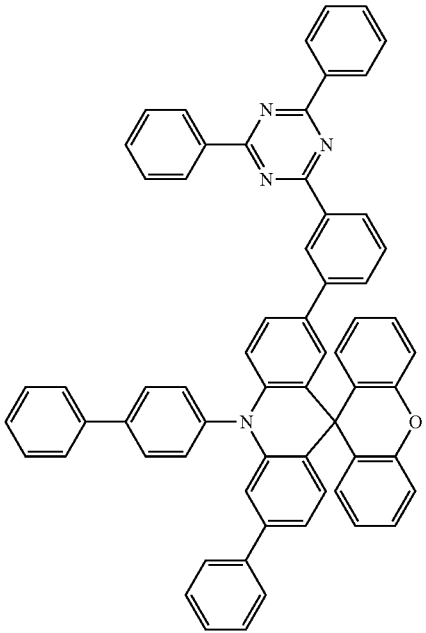<br>864377-31-1<br>130 mmol | 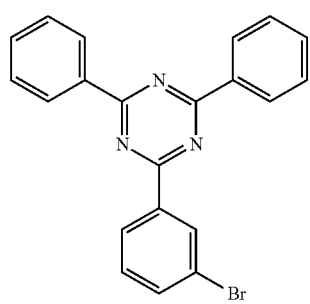 [SMILES: Brc1cccc(-c2nc(-c3ccccc3)nc(-c3ccccc3)n2)c1] | 29% |

Example 86: 3,6-Diphenyl-10-m-biphenylspiro[acridine-9(10H),9'-xanthene]

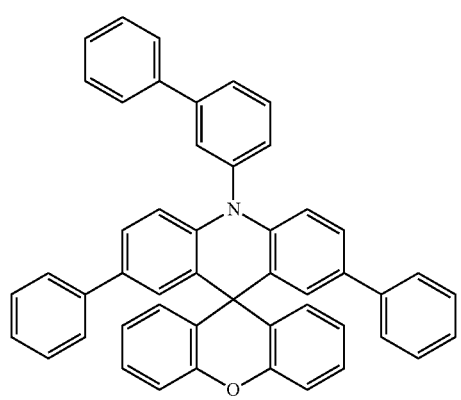 [SMILES: c1ccc(-c2cccc(N3c4ccc(-c5ccccc5)cc4C4(c5ccccc5Oc5ccccc54)c4cc(-c5ccccc5)ccc43)c2)cc1]

A mixture of 50.0 g (100 mmol) of 3,6-diphenylspiro[acridine-9(10H),9'-xanthene], Ex. 60, 30.3 g (130 mmol) of 3-bromo-1,1'-biphenyl [2113-57-7], 14.4 g (150 mmol) of sodium tert-butoxide, 526 mg (2.6 mmol) of tri-tert-butylphosphine, 449 mg (2 mmol) of palladium(II) acetate and 500 ml of o-xylene is heated under reflux for 8 h until the amine has been consumed. After cooling to 60° C., 500 ml of water are added, the organic phase is separated off, washed once with 500 ml of water and once with 500 ml of saturated sodium chloride solution and then dried over magnesium sulfate. The desiccant is filtered off via a Celite bed, rinsed with o-xylene, the o-xylene is removed in vacuo, and the residue is recrystallised five times from dioxane (3 ml/g) with addition of ethanol (1-2 ml/g) at the boiling point. The further purification is carried out by fractional sublimation twice (p about $10^{-6}$ mbar, T=300-320° C.). Yield: 26.7 g (41 mmol), 41%; purity: >99.9% according to HPLC.

The following compounds can be obtained analogously:

| Ex. | Starting materials amine/bromide | Product | Yield |
|---|---|---|---|
| 87 | 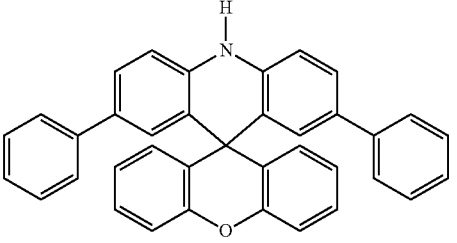 [SMILES: c1ccc(-c2ccc3c(c2)C2(c4cc(-c5ccccc5)ccc4N3)c3ccccc3Oc3ccccc32)cc1] 28320-31-2 | 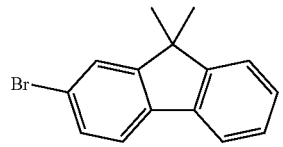 [SMILES: CC1(C)c2ccccc2-c2ccc(Br)cc21] | 48% |
| 88 | 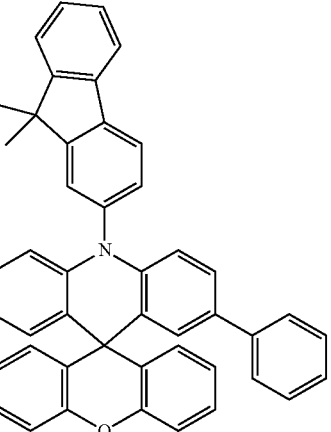 171408-76-7 | 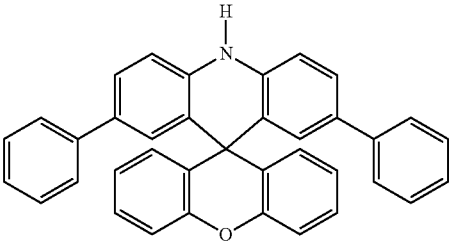 [SMILES: c1ccc(-c2ccc3c(c2)C2(c4cc(-c5ccccc5)ccc4N3)c3ccccc3Oc3ccccc32)cc1] | 45% |
| 89 | 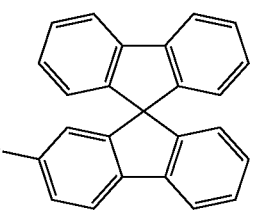 942615-32-9 | 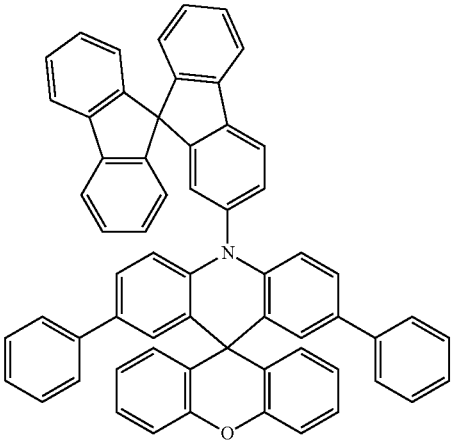 [SMILES: c1ccc(-c2ccc3c(c2)C2(c4ccccc4Oc4ccccc42)c2cc(-c4ccccc4)ccc2N3c2ccc3c(c2)C2(c4ccccc4-c4ccccc42)c2ccccc2-3)cc1] | 41% |

-continued
| Ex. | Starting materials amine/bromide | Product | Yield |
|---|---|---|---|
| 90 | 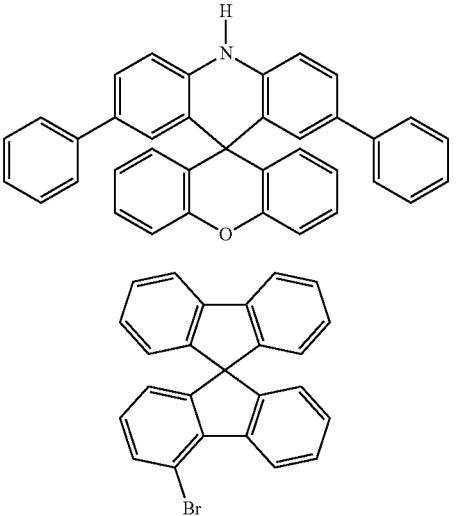 1161009-88-6 | 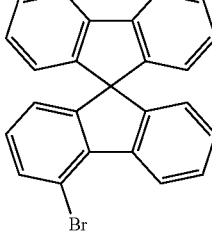 | 43% |
| 91 | 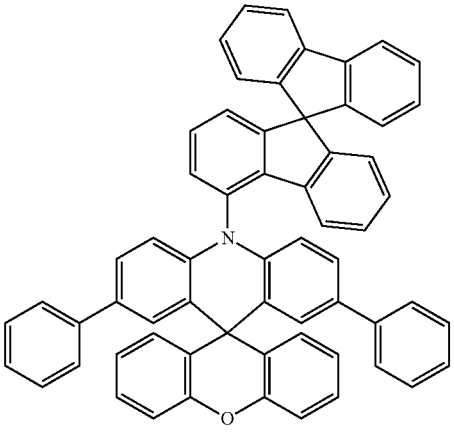 [SMILES: c1ccc(-c2ccc3c(c2)C2(c4ccccc4Oc4ccccc42)c2cc(-c4ccccc4)ccc2N3c2cccc3c2-c2ccccc2C32c3ccccc3-c3ccccc32)cc1] 50548-45-3 | 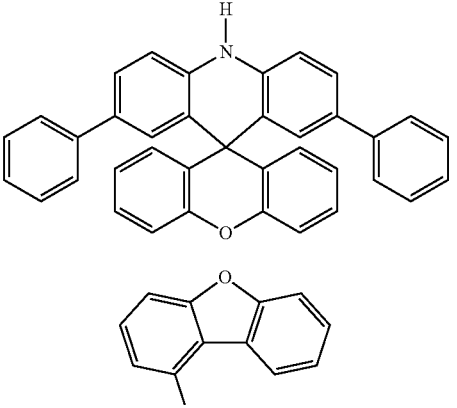 | 45% |

-continued
| Ex. | Starting materials amine/bromide | Product | Yield |
|---|---|---|---|
| 92 | 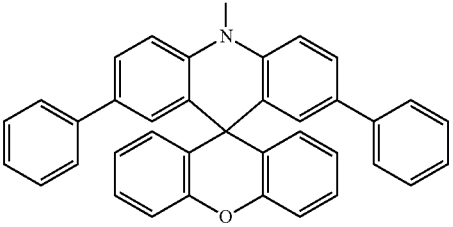 1097884-37-1 | 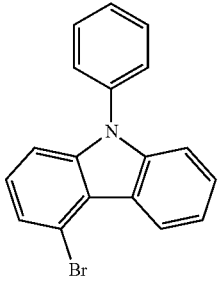 [SMILES: Brc1cccc2c1c1ccccc1n2-c1ccccc1] | 38% |
| 93 | 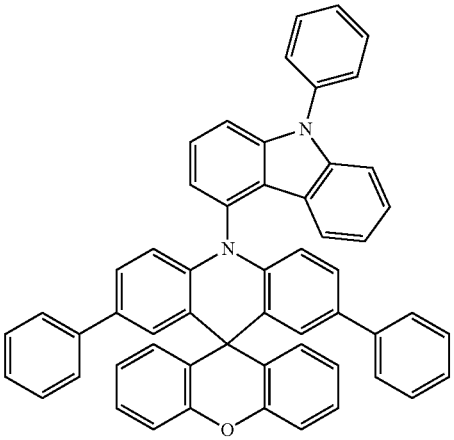 [SMILES: c1ccc(-c2ccc3c(c2)C2(c4ccccc4Oc4ccccc42)c2cc(-c4ccccc4)ccc2N3c2cccc3c2c2ccccc2n3-c2ccccc2)cc1] 868549-07-9 | 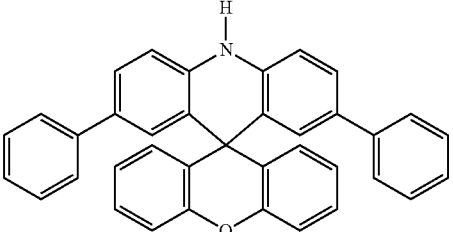 | 39% |

| Ex. | Starting materials amine/bromide | Product | Yield |
|---|---|---|---|
| 94 | 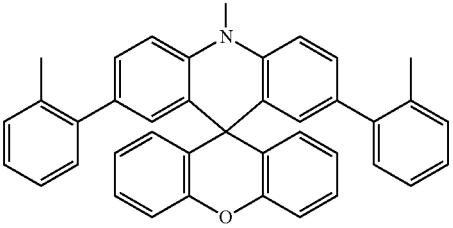 942615-32-9 | 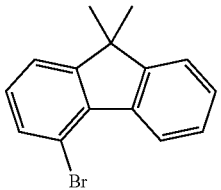 [SMILES: CC1(C)c2ccccc2-c2c(Br)cccc21] | 36% |
| 95 | 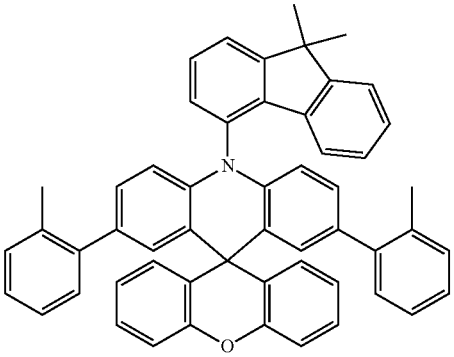 [SMILES: Cc1ccccc1-c1ccc2c(c1)C1(c3ccccc3Oc3ccccc31)c1cc(-c3ccccc3C)ccc1N2c1cccc2c1-c1ccccc1C2(C)C] 60631-83-6 | 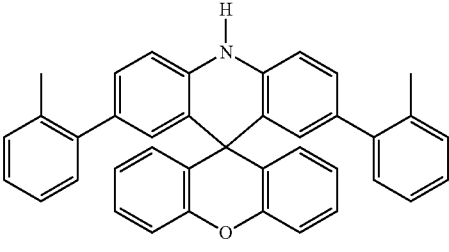 [SMILES: Cc1ccccc1-c1ccc2c(c1)C1(c3cc(-c4ccccc4C)ccc3N2)c2ccccc2Oc2ccccc21] | 37% |
| 96 | 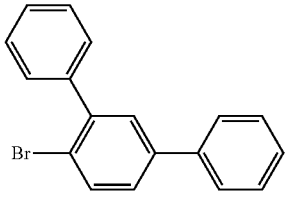 [SMILES: Brc1ccc(-c2ccccc2)cc1-c1ccccc1] 60631-83-6 | 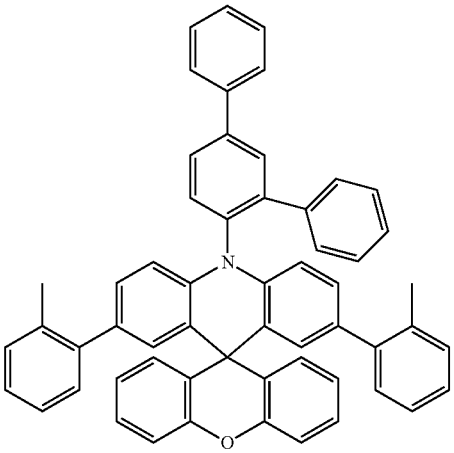 [SMILES: Cc1ccccc1-c1ccc2c(c1)C1(c3ccccc3Oc3ccccc31)c1cc(-c3ccccc3C)ccc1N2c1ccc(-c2ccccc2)cc1-c1ccccc1] | 28% |

-continued
| Ex. | Starting materials amine/bromide | Product | Yield |
|---|---|---|---|
| 97 | 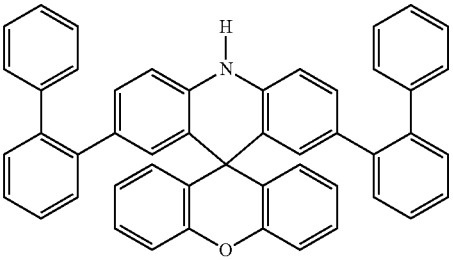 [SMILES: c1ccc(-c2ccccc2-c2ccc3c(c2)C2(c4cc(-c5ccccc5-c5ccccc5)ccc4N3)c3ccccc3Oc3ccccc32)cc1] 854952-41-3 | 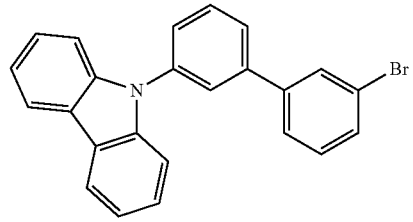 [SMILES: Brc1cccc(-c2cccc(-n3c4ccccc4c4ccccc43)c2)c1] Comp. is heated in a high vacuum in order to remove solvent residues | 28% |
| 98 | 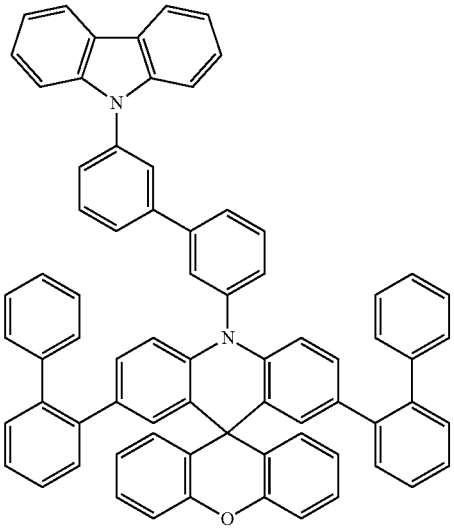 [SMILES: c1ccc(-c2ccccc2-c2ccc3c(c2)C2(c4ccccc4Oc4ccccc42)c2cc(-c4ccccc4-c4ccccc4)ccc2N3c2cccc(-c3cccc(-n4c5ccccc5c5ccccc54)c3)c2)cc1] 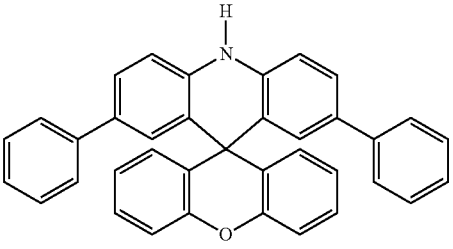 [SMILES: c1ccc(-c2ccc3c(c2)C2(c4cc(-c5ccccc5)ccc4N3)c3ccccc3Oc3ccccc32)cc1] 92-86-4 45 mmol | 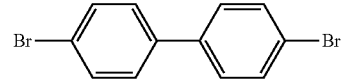 [SMILES: Brc1ccc(-c2ccc(Br)cc2)cc1] Comp. is heated in a high vacuum in order to remove solvent residues | 33% |

-continued
| Ex. | Starting materials amine/bromide | Product | Yield |
|---|---|---|---|
| 99 | 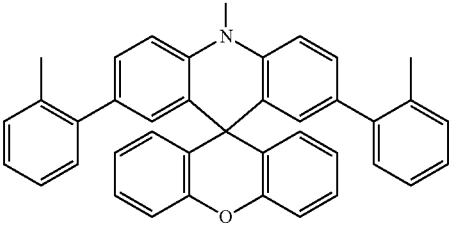 16400-51-4 45 mmol | 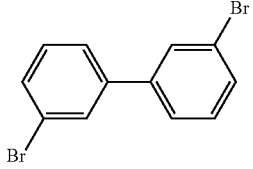 Comp. is heated in a high vacuum in order to remove solvent residues | 29% |
| 100 | 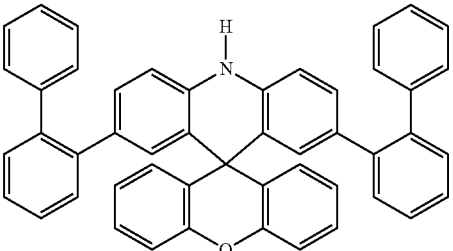 1257321-41-7 45 mmol | 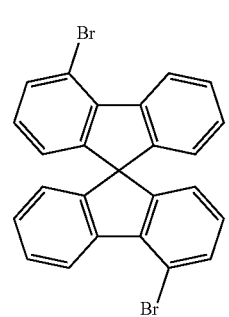 [SMILES: Brc1cccc2c1-c1ccccc1C21c2ccccc2-c2c(Br)cccc21] Comp. is heated in a high vacuum in order to remove solvent residues | 23% |

| Ex. | Starting materials amine/bromide | Product | Yield |
|---|---|---|---|
| 101 | 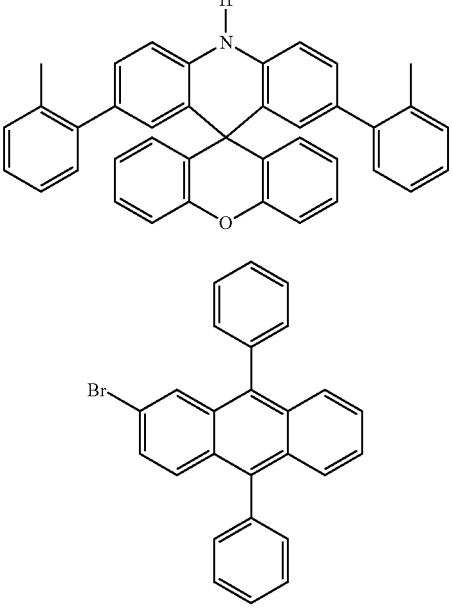 201731-79-5 90 mmol | 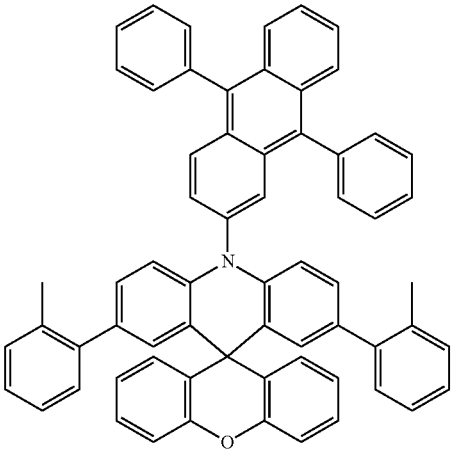 [SMILES: Cc1ccccc1-c1ccc2c(c1)C1(c3ccccc3Oc3ccccc31)c1cc(-c3ccccc3C)ccc1N2c1ccc2c(-c3ccccc3)c3ccccc3c(-c3ccccc3)c2c1] | 34% |
| 102 | 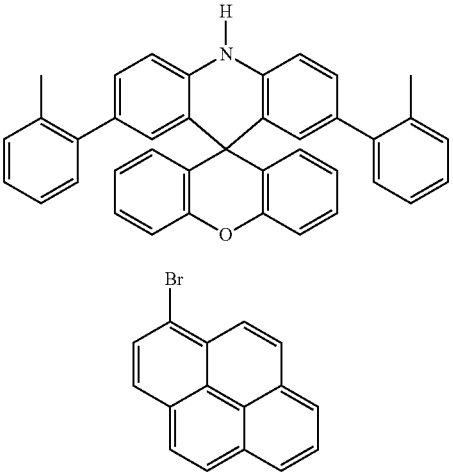 1714-29-0 90 mmol | 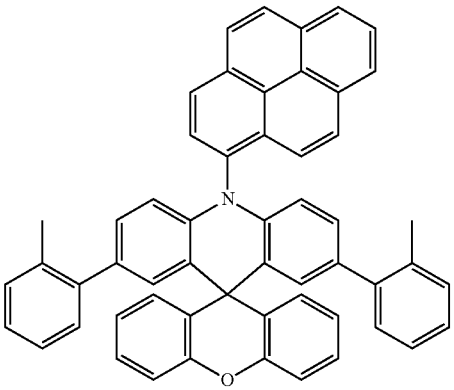 [SMILES: Cc1ccccc1-c1ccc2c(c1)C1(c3ccccc3Oc3ccccc31)c1cc(-c3ccccc3C)ccc1N2c1ccc2ccc3cccc4ccc1c2c34] | 38% |

-continued
| Ex. | Starting materials amine/bromide | Product | Yield |
|---|---|---|---|
| 103 | 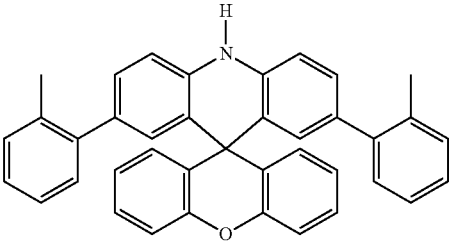 [SMILES: Cc1ccccc1-c1ccc2c(c1)C1(c3cc(-c4ccccc4C)ccc3N2)c2ccccc2Oc2ccccc21]<br>27973-29-1<br>45 mmol | 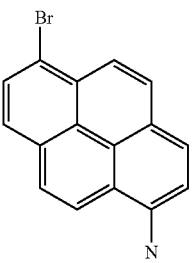 [SMILES: Nc1ccc2ccc3c(Br)ccc4ccc1c2c43] | 26% |
| 104 | 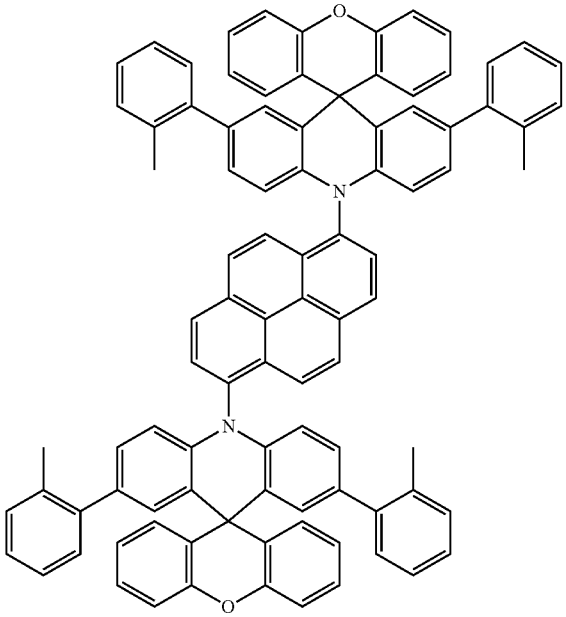 [SMILES: Cc1ccccc1-c1ccc2c(c1)C1(c3ccccc3Oc3ccccc31)c1cc(-c3ccccc3C)ccc1N2c1ccc2ccc3c(N4c5ccc(-c6ccccc6C)cc5C5(c6ccccc6Oc6ccccc65)c5cc(-c6ccccc6C)ccc54)ccc4ccc1c2c43]<br>27973-29-1<br>45 mmol | 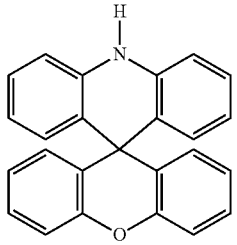 [SMILES: c1ccc2c(c1)Nc1ccccc1C21c2ccccc2Oc2ccccc21] | 31% |

-continued

| Ex. | Starting materials amine/bromide | Product | Yield |
|---|---|---|---|
| 105 | 1005771-04-9<br>45 mmol | | 33% |
| 106 | 1001911-20-1<br>45 mmol | | 30% |

| Ex. | Starting materials amine/bromide | Product | Yield |
|---|---|---|---|
| 107 | 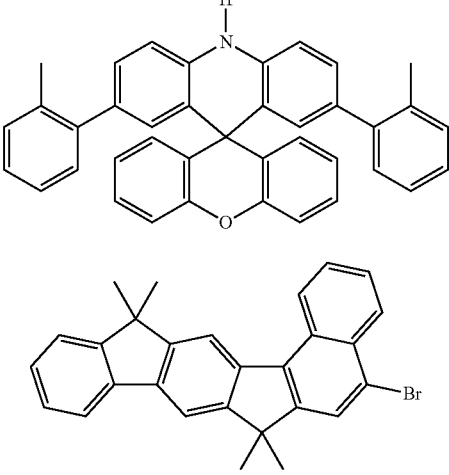 | 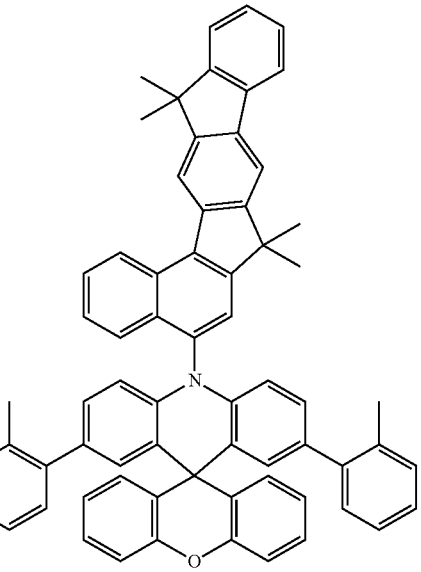 | 29% |

Example 108: 3-(4,4,5,5-Tetramethyl-1,3,2-dioxaborolan-2-yl)-6-phenyl-10-p-biphenylspiro[acridine-9(10H),9'-xanthene]

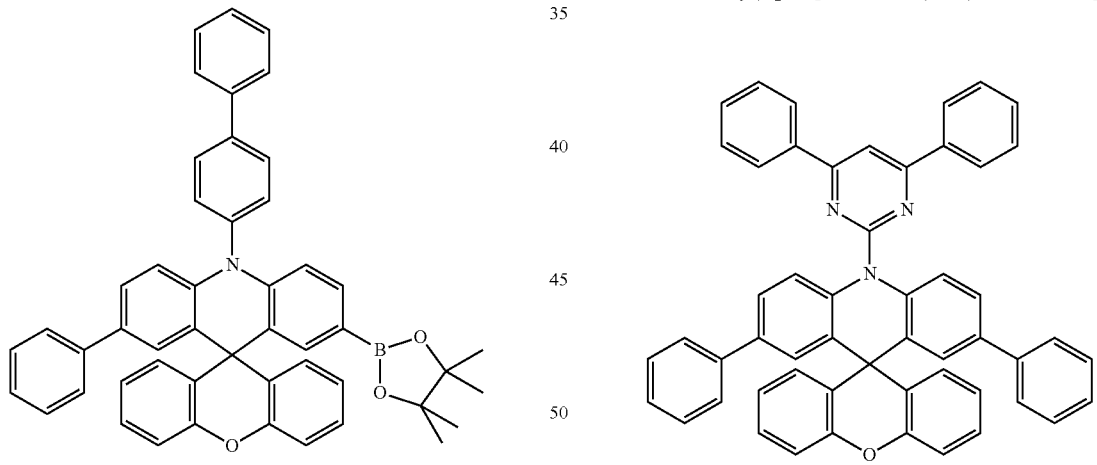

A mixture of 65.4 g (100 mmol) of 3-bromo-6-phenyl-10-p-biphenylspiro[acridine-9(10H),9'-xanthene], Ex. 12, 27.9 g (110 mmol) of bis(pinacolato)diborane [73183-34-3], 29.5 g (300 mmol) of potassium acetate, 200 g of glass beads (diameter 3 mm), 561 mg (2 mmol) of tricyclohexylphosphine, 249 mg (1 mmol) of palladium(III) acetate and 1000 ml of dioxane is stirred at 80° C. for 16 h until the bromide has been consumed. After cooling and removal of the solvent in vacuo, the residue is taken up in 1000 ml of ethyl acetate, filtered through a Celite bed, the filtrate is evaporated in vacuo to incipient crystallisation, and finally about 100 ml of methanol are added dropwise in order to complete the crystallisation. Yield: 61.0 g (87 mmol), 87%; purity: about 97% according to $^1$H-NMR.

The corresponding boronic acid ester, Ex. 109, can be prepared analogously from 3-bromo-7-phenyl-10-m-biphenylspiro[acridine-9(10H),9'-xanthene], Ex. 39.

Example 110: 3,6-Diphenyl-10-(4,6-diphenylpyrimidin-2-yl)spiro[acridine-9(10H),9'-xanthene]

4.8 g (120 mmol) of sodium hydride, dispersion in mineral oil, 60% by weight, are added in portions to a suspension of 50.0 g (100 mmol) of 3,6-diphenylspiro[acridine-9(10H),9'-xanthene], Ex. 60, in 500 ml of DMF, and the mixture is stirred at room temperature for 30 min. A solution of 32.0 g (120 mmol) of 2-chloro-4,6-diphenylpyrimidine [2915-16-4] in 500 ml of THF is then added dropwise over the course of 30 min., and the mixture is stirred at room temperature for a further 16 h. The reaction mixture is poured onto 2000 g of ice with vigorous stirring, the precipitated solid is filtered off with suction, washed three times with 300 ml of methanol each time and then three times with 300 ml of n-heptane each time and dried in vacuo. The crude product is taken up in 1000 ml of hot toluene, filtered through a Celite bed, the filtrate is evaporated in vacuo to incipient crystallisation, and finally about 100 ml of methanol are added dropwise in order to complete the crystallisation. The recrystallisation is carried out from dioxane, followed by fractional sublimation twice (p about $10^{-6}$ mbar, T=300-330° C.). Yield: 28.5 g (39 mmol), 39%; purity: >99.9% according to HPLC.

The following compounds can be obtained analogously:

| Ex. | Starting materials amine/chloride | Product | Yield |
|---|---|---|---|
| 111 | 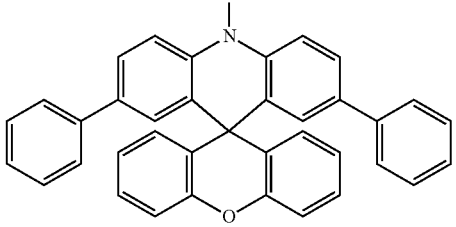 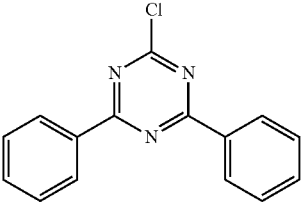 [SMILES: Clc1nc(-c2ccccc2)nc(-c2ccccc2)n1] 3842-55-5 | 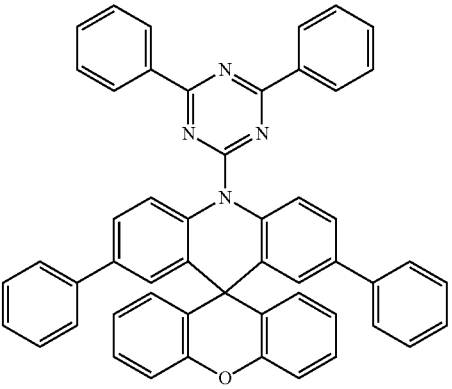 [SMILES: c1ccc(-c2ccc3c(c2)C2(c4ccccc4Oc4ccccc42)c2cc(-c4ccccc4)ccc2N3c2nc(-c3ccccc3)nc(-c3ccccc3)n2)cc1] | 46% |
| 112 | 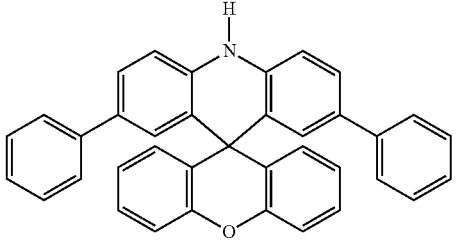 [SMILES: c1ccc(-c2ccc3c(c2)C2(c4cc(-c5ccccc5)ccc4N3)c3ccccc3Oc3ccccc32)cc1] 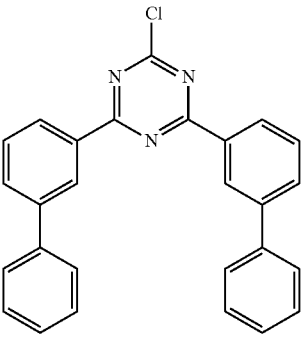 [SMILES: Clc1nc(-c2cccc(-c3ccccc3)c2)nc(-c2cccc(-c3ccccc3)c2)n1] 1205748-61-3 | 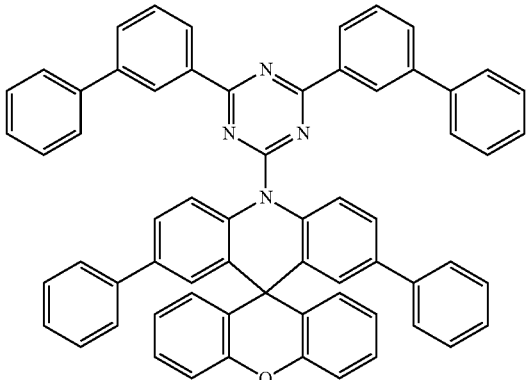 | 37% |

-continued
| Ex. | Starting materials amine/chloride | Product | Yield |
|---|---|---|---|
| 113 | 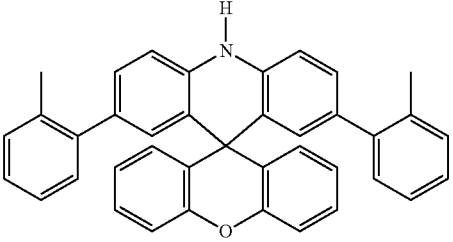 [SMILES: Cc1ccccc1-c1ccc2c(c1)C1(c3cc(-c4ccccc4C)ccc3N2)c2ccccc2Oc2ccccc21] 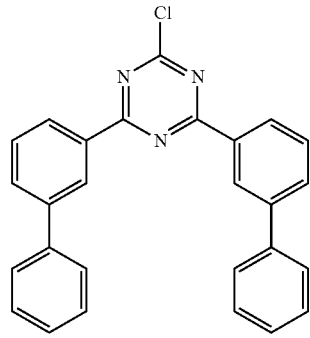 [SMILES: Clc1nc(-c2cccc(-c3ccccc3)c2)nc(-c2cccc(-c3ccccc3)c2)n1] 1205748-61-3 | 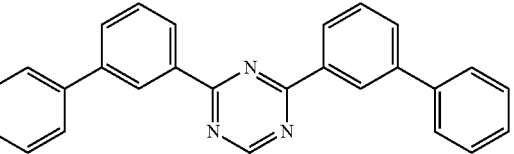 | 36% |
| 114 | 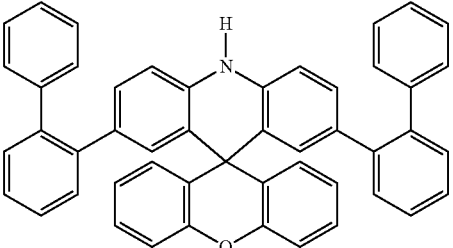 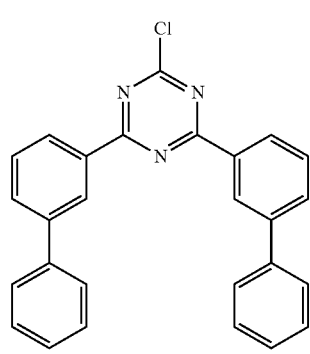 [SMILES: Clc1nc(-c2cccc(-c3ccccc3)c2)nc(-c2cccc(-c3ccccc3)c2)n1] 1205748-61-3 | 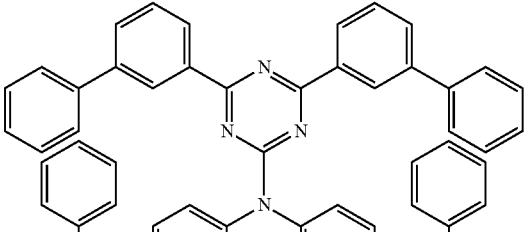 | 31% |

Example 115: 3,6-Bis(2-methylphenyl)-10-phenyl-spiro[acridine-9(10H),9'-(2,7-bisdiphenylphosinoyl)xanthene]

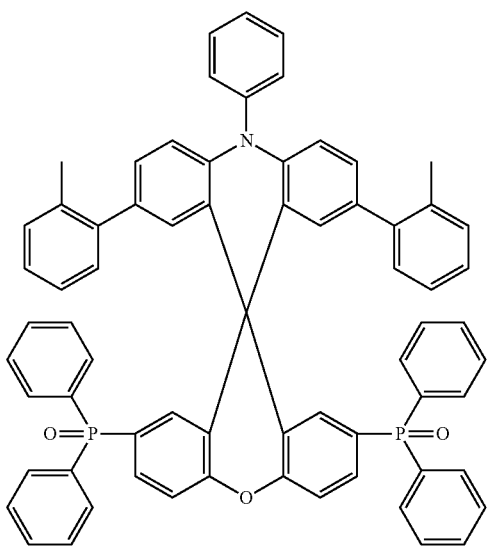 [SMILES: Cc1ccccc1-c1ccc2c(c1)C1(c3cc(P(=O)(c4ccccc4)c4ccccc4)ccc3Oc3ccc(P(=O)(c4ccccc4)c4ccccc4)cc31)c1cc(-c3ccccc3C)ccc1N2c1ccccc1]

a) 10-Phenylspiro[acridine-9(10H),9'-(2,7-bisdiphenylphosinoyl)xanthene], Ex. 116

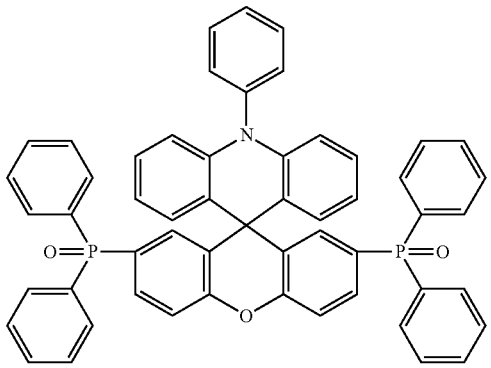 [SMILES: O=P(c1ccccc1)(c1ccccc1)c1ccc2c(c1)C1(c3cc(P(=O)(c4ccccc4)c4ccccc4)ccc3O2)c2ccccc2N(c2ccccc2)c2ccccc21]

80.0 ml (200 mmol) of n-BuLi, 2.5 molar in n-hexane, are added dropwise to a vigorously stirred solution, cooled to −78° C., of 58.1 g (100 mmol) of 10-phenylspiro[acridine-9(10H),9'-(2,7-dibromo)xanthene], Ex. 28, in 1000 ml of THF, and the mixture is then stirred for a further 1 h. A mixture of 48.5 g (220 mmol) of chlorodiphenylphosphine [1079-66-7] and 100 ml of THF is then slowly added dropwise, the mixture is stirred for a further 30 min., allowed to warm to room temperature, the THF is then removed in vacuo, the residue is taken up in 1000 ml of ethyl acetate, and a mixture of 100 ml of water and 20.6 ml (200 mmol) of 30% by weight hydrogen peroxide is added with very vigorous stirring. After stirring for 16 h, the reaction mixture is evaporated to about 200 ml in vacuo, 300 ml of ethanol are then added, and the mixture is stirred for a further 2 h. The precipitated solid is filtered off with suction, washed with ethanol and dried in vacuo. The solid obtained in this way is recrystallised once from DMF/ethanol. Yield: 48.6 g (59 mmol), 59%; purity: >98% according to 1H-NMR.

b) 3,6-Dibromo-10-phenylspiro[acridine-9(10H),9'-(bis-2,7-diphenylphosinoyl)xanthene]

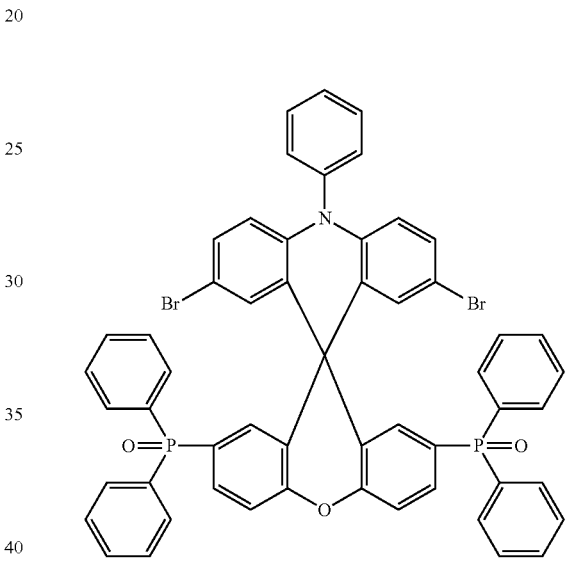

NBS bromination: procedure analogous to Ex. 11. Batch 41.2 g (50 mmol) of 10-phenylspiro[acridine-9(10H),9'-(bis-2,7-diphenylphosinoyl)xanthene], step a) and 19.6 g (110 mmol) of NBS. Yield: 47.1 g (48 mmol), 96%; purity: >98% according to $^1$H-NMR.

c) 3,6-Bis(2-methylphenyl)-10-phenylspiro[acridine-9(10H),9'-(bis-2,7-diphenylphosinoyl)xanthene]

Suzuki coupling: procedure analogous to Ex. 14. Batch 47.1 g (48 mmol) of 3,6-dibromo-10-phenylspiro[acridine-9(10H),9'-(bis-2,7-diphenylphosinoyl)xanthene], step b) and 17.0 g (125 mmol) of 2-tolylboronic acid [16419-60-6]. Yield: 17.0 g (17 mmol), 35%; purity: >99.9% according to HPLC.

The following compounds can be obtained analogously:

| Ex. | Starting materials phosphine or borane/ boronic acid | Product | Yield |
|---|---|---|---|
| 117 | 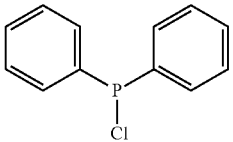 [SMILES: ClP(c1ccccc1)c1ccccc1] 1079-66-9<br><br>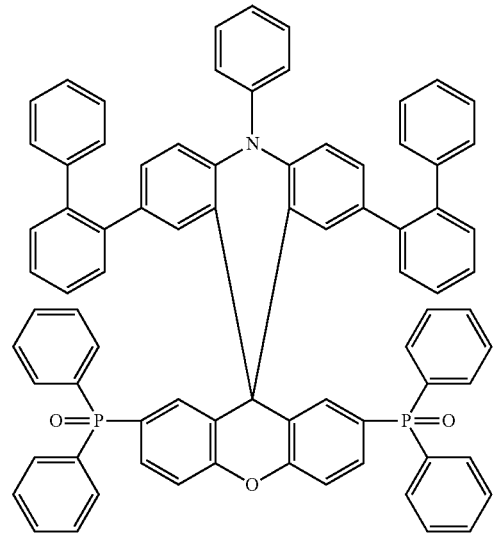 [SMILES: O=P(c1ccccc1)(c1ccccc1)c1ccc2c(c1)C1(c3cc(P(=O)(c4ccccc4)c4ccccc4)ccc3O2)c2cc(-c3ccccc3-c3ccccc3)ccc2N(c2ccccc2)c2ccc(-c3ccccc3-c3ccccc3)cc21] 4688-76-0 | 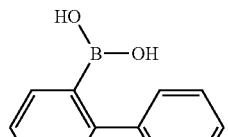 | 36% |
| 118 | 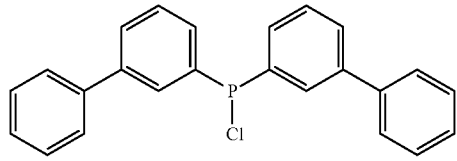 [SMILES: ClP(c1cccc(-c2ccccc2)c1)c1cccc(-c2ccccc2)c1] 1190100-29-8<br><br>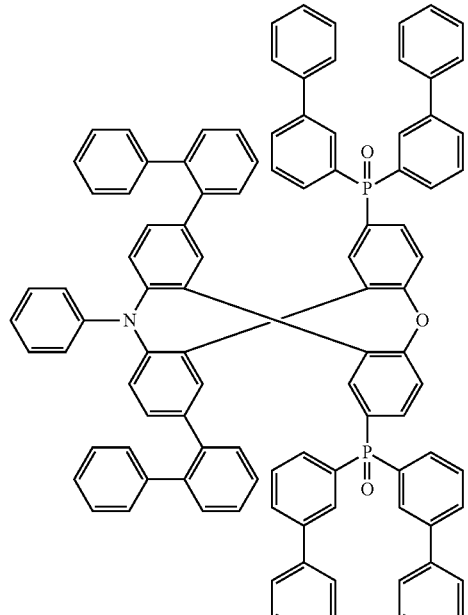 4688-76-0 | 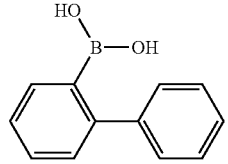 [SMILES: OB(O)c1ccccc1-c1ccccc1]<br><br>Comp. is heated in a high vacuum in order to remove solvent residues | 27% |

| Ex. | Starting materials phosphine or borane/ boronic acid | Product | Yield |
|---|---|---|---|
| 119 | 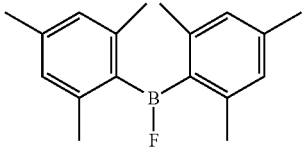 436-59-9 The H₂O₂ oxidation is omitted 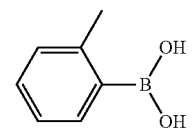 16419-60-6 | 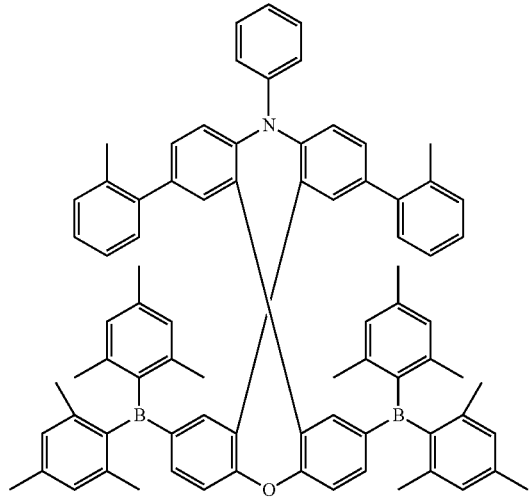 | 33% |

Example 120

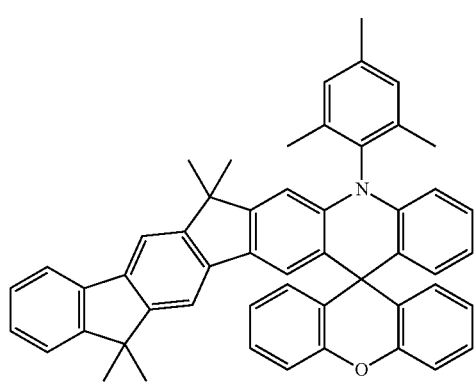 [SMILES: Cc1cc(C)c(N2c3ccccc3C3(c4ccccc4Oc4ccccc43)c3cc4c(cc32)C(C)(C)c2cc3c(cc2-4)C(C)(C)c2ccccc2-3)c(C)c1]

a) (6,6,12,12-Tetramethyl-6,12-dihydroindeno[1,2-b]fluoren-2yl)(2,4,6-trimethylphenyl)amine

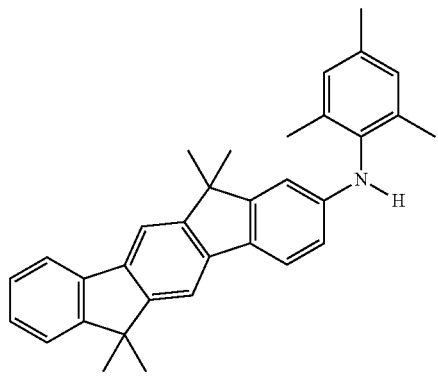 [SMILES: Cc1cc(C)c(Nc2ccc3c(c2)C(C)(C)c2cc4c(cc2-3)C(C)(C)c2ccccc2-4)c(C)c1]

404 mg (2 mmol) of tri-tert-butylphosphine and then 225 mg (1 mmol) of palladium(II) acetate are added to a mixture of 38.9 g (100 mmol) of 2-bromo-6,6,12,12-tetramethyl-6,12-dihydroindeno[1,2-b]fluorene, 13.5 g (100 mmol) of 2,4,6-trimethylphenylamine, 12.5 g (130 mmol) of sodium tert-butoxide and 500 ml of toluene, and the mixture is heated under reflux for 16 h. After cooling, 300 ml of water are added, the org. phase is separated off, dried over magnesium sulfate, then filtered off via a Celite bed, and the toluene is removed in vacuo. Yield: 38.7 g (87 mmol), 87%; purity: about 95% according to ¹H-NMR.

b) (2-Bromophenyl)-(6,6,12,12-tetramethyl-6,12-dihydroindeno-[1,2-b]fluoren-2yl)-(2,4,6-trimethylphenyl)amine

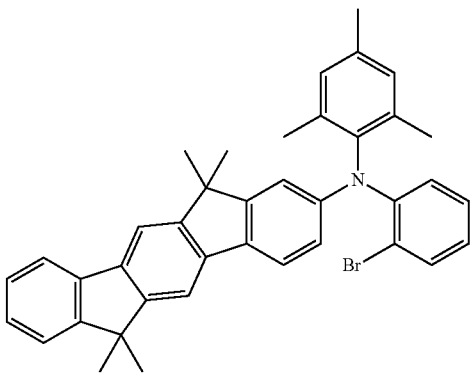 [SMILES: Cc1cc(C)c(N(c2ccc3c(c2)C(C)(C)c2cc4c(cc2-3)C(C)(C)c2ccccc2-4)c2ccccc2Br)c(C)c1]

Buchwald coupling: procedure analogous to Ex. 1. Batch 22.2 g (50 mmol) of (6,6,12,12-tetramethyl-6,12-dihydroindeno[1,2-b]fluoren-2yl)-(2,4,6-trimethylphenyl)amine, step a). Yield: 19.8 g (33 mmol), 66%; purity: >98% according to ¹H-NMR.

c)

Procedure analogous to Ex. 6. Batch 18.0 g (30 mmol) of (2-bromophenyl)(6,6,12,12-tetramethyl-6,12-dihydroindeno[1,2-b]fluoren-2yl)-(2,4,6-trimethylphenyl)amine, step b). Purification by recrystallisation four times from DMF and fractional sublimation twice (p about $10^{-6}$ mbar, T=300-320° C.). Yield: 6.3 g (9 mmol), 30%, purity: >99.9% according to HPLC.

The following compounds can be obtained analogously:

| Ex. | Starting materials bromide—step a) bromoiodoaromatic compound step b) | Product | Yield |
|---|---|---|---|
| 121 | 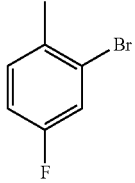<br>202865-73-4 | 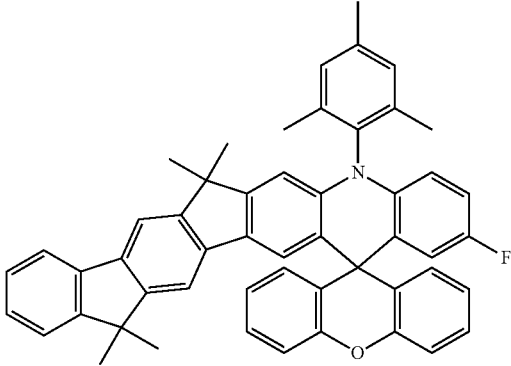 [SMILES: Cc1cc(C)c(N2c3ccc(F)cc3C3(c4ccccc4Oc4ccccc43)c3cc4c(cc32)C(C)(C)c2cc3c(cc2-4)C(C)(C)c2ccccc2-3)c(C)c1] | 26% |
| 122 | 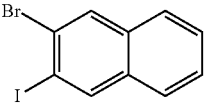 [SMILES: Brc1cc2ccccc2cc1I]<br>102153-44-6 | 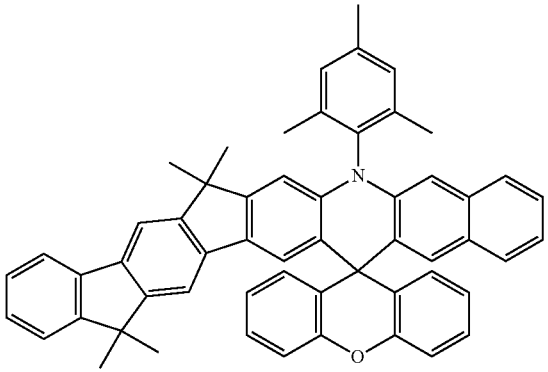 [SMILES: Cc1cc(C)c(N2c3cc4c(cc3C3(c5ccccc5Oc5ccccc53)c3cc5ccccc5cc32)-c2cc3c(cc2C4(C)C)-c2ccccc2C3(C)C)c(C)c1] | 27% |
| 123 | 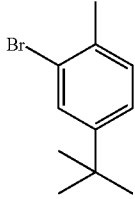<br>860435-39-8 | 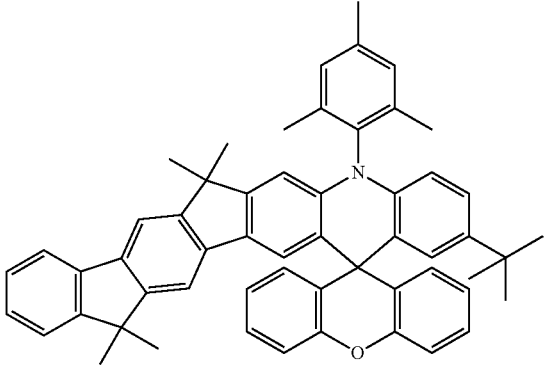 [SMILES: Cc1cc(C)c(N2c3ccc(C(C)(C)C)cc3C3(c4ccccc4Oc4ccccc43)c3cc4c(cc32)C(C)(C)c2cc3c(cc2-4)C(C)(C)c2ccccc2-3)c(C)c1] | 29% |

-continued

| Ex. | Starting materials bromide—step a) bromoiodoaromatic compound step b) | Product | Yield |
|---|---|---|---|
| 124 | 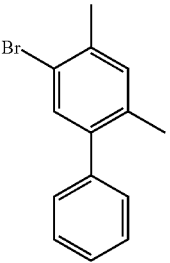 1238830-99-3 | 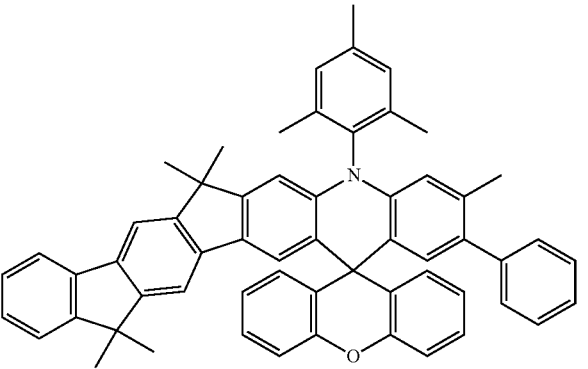 [SMILES: Cc1cc(C)c(N2c3cc(C)c(-c4ccccc4)cc3C3(c4ccccc4Oc4ccccc43)c3cc4c(cc32)C(C)(C)c2cc3c(cc2-4)C(C)(C)c2ccccc2-3)c(C)c1] | 25% |
| 125 | 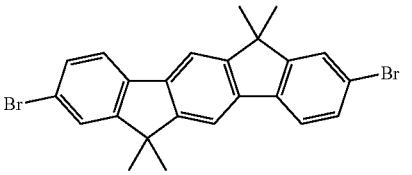 [SMILES: CC1(C)c2cc(Br)ccc2-c2cc3c(cc21)-c1ccc(Br)cc1C3(C)C] 872705-64-1<br>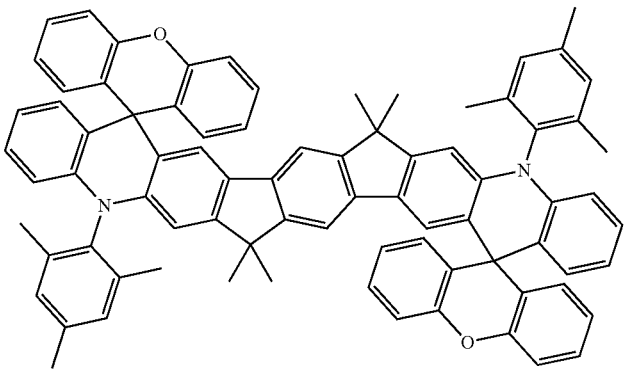 [SMILES: Cc1cc(C)c(N2c3ccccc3C3(c4ccccc4Oc4ccccc43)c3cc4c(cc32)C(C)(C)c2cc3c(cc2-4)C(C)(C)c2cc4c(cc2-3)C2(c3ccccc3Oc3ccccc32)c2ccccc2N4c2c(C)cc(C)cc2C)c(C)c1] 583-55-1 | 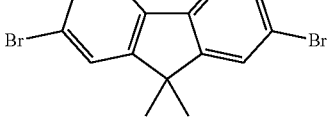 | 33% |
| 126 | 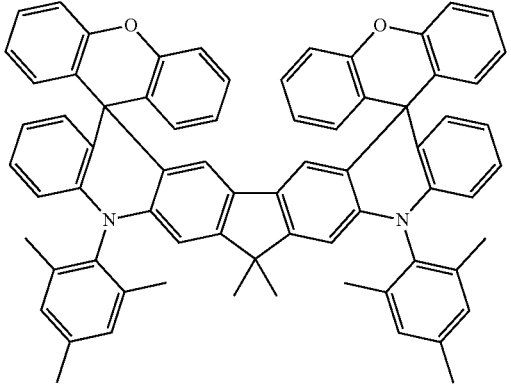 28320-32-3<br>583-55-1 | | 30% |

Production of the OLEDs

OLEDs according to the invention and OLEDs in accordance with the prior art are produced by a general process in accordance with WO 2004/058911, which is adapted to the circumstances described here (layer-thickness variation, materials).

The structure and data of various OLEDs are presented in the following examples (see Tables 1 to 11). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates for experiments V1, V2 and D1-D15, those which do not have an additional PEDOT layer are used in Examples D16-D119 and in D-W1. The OLEDs are applied to them.

All materials are applied by thermal vapour deposition in a vacuum chamber. The materials required for the production of the OLEDs are shown in Table 12. The emission layer here always consists of at least one matrix material (host material) and an emitting dopant (emitter), which is admixed with the matrix material or matrix materials in a certain proportion by volume by co-evaporation. An expression such as H1(95%):SEB(5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U @ 1000 cd/m$^2$ in Table 2 and 4 denotes the voltage required for a luminous density of 1000 cd/m$^2$. Finally, EQE 1000 cd/m$^2$ denotes the external quantum efficiency at an operating luminous density of 1000 cd/m$^2$. LT80 @ 6000 cd/m2 is the lifetime by which the OLED has dropped at a luminance of 6000 cd/m$^2$ to 80% of the initial intensity, i.e. to 4800 cd/m$^2$.

Use of the Compounds According to the Invention in Fluorescent and Phosphorescent OLEDs The OLEDs have in principle the following layer structure: substrate/optional hole-injection layer (IL)/hole-transport layer (HTL)/interlayer (IL)/hole-transport layer (HTL2)/electron-blocking layer (EBL)/emission layer (EML)/electron-transport layer (ETL)/optional electron-injection layer (EIL) and finally a cathode. The cathode is formed by an aluminium layer with a thickness of 100 nm. The precise structure of the OLEDs is shown in the tables.

The compounds according to the invention are particularly suitable as HTM (hole-transport material) or EBM (electron-blocking material) in OLEDs. They are suitable for use in a single layer, but also as mixed component as HTM, EBM or as constituent of the emitting layer. Compared with comparative devices in accordance with the prior art (V1 and V2), all samples comprising the compounds according to the invention exhibit higher efficiencies and/or improved lifetimes. Compared with the reference material NPB, the compounds according to the invention exhibit better efficiencies and better lifetimes.

TABLE 1

Structure of the OLEDs

| Ex. | IL Thickness/nm | HTL Thickness/nm | IL Thickness/nm | HTL2 Thickness/nm | EBL Thickness/nm | EML Thickness/nm | ETL Thickness/nm |
|---|---|---|---|---|---|---|---|
| V1 | HIL1 6 nm | HIL2 130 nm | HIL1 5 nm | NPB 10 nm | NPB 20 nm | H1(95%):SEB1(5%) 20 nm | ETM1(50%):LIQ(50%) 30 nm |
| D1 | HIL1 5 nm | HIL2 130 nm | HIL1 5 nm | NPB 10 nm | Ex. 15 20 nm | H1(95%):SEB1(5%) 20 nm | ETM1(50%):LIQ(50%) 30 nm |
| D2 | HIL1 5 nm | HIL2 130 nm | HIL1 5 nm | — | Ex. 15 30 nm | H1(95%):SEB1(5%) 20 nm | ETM1(50%):LIQ(50%) 30 nm |
| D3 | HIL1 5 nm | HIL2 130 nm | HIL1 5 nm | NPB 10 nm | Ex. 17 20 nm | H1(95%):SEB1(5%) 20 nm | ETM1(50%):LIQ(50%) 30 nm |
| D4 | HIL1 5 nm | HIL2 130 nm | HIL1 5 nm | — | Ex. 17 30 nm | H1(95%):SEB1(5%) 20 nm | ETM1(50%):LIQ(50%) 30 nm |

TABLE 2

Data of the OLEDs

| Ex. | U @ 1000 cd/m2 V | EQE @ 1000 cd/m2 % | LT80 @ 6000 cd/m$^2$ [h] | CIE x | CIE y |
|---|---|---|---|---|---|
| V1 | 4.7 | 4.8 | 70 | 0.14 | 0.17 |
| D1 | 4.4 | 6.2 | 70 | 0.14 | 0.16 |
| D2 | 4.3 | 6.6 | 80 | 0.14 | 0.16 |
| D3 | 4.4 | 7.4 | 90 | 0.14 | 0.16 |
| D4 | 4.4 | 7.3 | 105 | 0.14 | 0.16 |

TABLE 3

Structure of the OLEDs

| Ex. | HTL Thickness/nm | IL Thickness/nm | HTL2 Thickness/nm | EBL Thickness/nm | EML Thickness/nm | ETL Thickness/nm |
|---|---|---|---|---|---|---|
| V2 | HIL2 70 nm | HIL1 5 nm | — | NPB 90 nm | H2(88%):Irpy(12%) 30 nm | ETM1(50%):LIQ(50%) 40 nm |
| D5 | HIL2 70 nm | HIL1 5 nm | NPB 10 nm | Ex. 15 80 nm | H2(88%):Irpy(12%) 30 nm | ETM1(50%):LIQ(50%) 40 nm |
| D6 | HIL2 70 nm | HIL1 5 nm | NPB 10 nm | Ex. 17 80 nm | H2(88%):Irpy(12%) 30 nm | ETM1(50%):LIQ(50%) 40 nm |
| D7 | HIL2 70 nm | HIL1 5 nm | — | Ex. 15 90 nm | H2(70%):Ex. 7(25%):Irpy(5%) 30 nm | ETM1(50%):LIQ(50%) 40 nm |

TABLE 3-continued

Structure of the OLEDs

| Ex. | HTL Thickness/nm | IL Thickness/nm | HTL2 Thickness/nm | EBL Thickness/nm | EML Thickness/nm | ETL Thickness/nm |
|---|---|---|---|---|---|---|
| D8 | HIL2 70 nm | HIL1 5 nm | — | Ex. 15 90 nm | H2(70%):Ex. 8(25%):Irpy(5%) 30 nm | ETM1(50%):LIQ(50%) 40 nm |
| D9 | HIL2 70 nm | HIL1 5 nm | — | Ex. 15 90 nm | H2(70%):Ex. 9(25%):Irpy(5%) 30 nm | ETM1(50%):LIQ(50%) 40 nm |
| D10 | HIL2 70 nm | HIL1 5 nm | — | Ex. 15 90 nm | H2(75%):Ex. 10(20%):Irpy(5%) 30 nm | ETM1(50%):LIQ(50%) 40 nm |
| D11 | HIL2 70 nm | HIL1 5 nm | — | Ex. 15 90 nm | H2(50%):Ex14(40%):Irpy(10%) 30 nm | ETM1(50%):LIQ(50%) 40 nm |
| D12 | HIL2 70 nm | HIL1 5 nm | — | Ex. 15 90 nm | H2(70%):Ex15(25%):Irpy(5%) 30 nm | ETM1(50%):LIQ(50%) 40 nm |
| D13 | HIL2 70 nm | HIL1 5 nm | — | Ex. 15 90 nm | H2(60%):Ex16(35%):Irpy(5%) 30 nm | ETM1(50%):LIQ(50%) 40 nm |
| D14 | HIL2 70 nm | HIL1 5 nm | — | Ex. 15 90 nm | H2(75%):Ex17(20%):Irpy(5%) 30 nm | ETM1(50%):LIQ(50%) 40 nm |
| D15 | HIL2 70 nm | HIL1 5 nm | — | Ex. 15 90 nm | H2(45%):Ex18(50%):Irpy(15%) 30 nm | ETM1(50%):LIQ(50%) 40 nm |

TABLE 4

Data of the OLEDs

| Ex. | U @ 1000 cd/m2 V | EQE @ 1000 cd/m2 % | LT80 @ 8000 cd/m$^2$ [h] | CIE x | CIE y |
|---|---|---|---|---|---|
| V2 | 3.6 | 14.4 | 85 | 0.32 | 0.63 |
| D5 | 3.2 | 17.9 | 120 | 0.33 | 0.63 |
| D6 | 3.4 | 18.4 | 110 | 0.33 | 0.63 |
| D7 | 3.2 | 18.8 | 140 | 0.33 | 0.64 |
| D8 | 3.3 | 19.0 | 130 | 0.33 | 0.63 |
| D9 | 3.2 | 18.0 | 110 | 0.33 | 0.64 |
| D10 | 3.2 | 18.2 | 115 | 0.33 | 0.63 |
| D11 | 3.4 | 18.7 | 100 | 0.33 | 0.63 |
| D12 | 3 2 | 16.5 | 145 | 0.33 | 0.64 |
| D13 | 3.3 | 18.8 | 125 | 0.33 | 0.64 |
| D14 | 3.2 | 17.0 | 160 | 0.33 | 0.63 |
| D15 | 3.3 | 18.2 | 120 | 0.33 | 0.63 |

Use of the Compounds According to the Invention in Fluorescent and Phosphorescent OLEDs Having a p-Doped Hole-Transport Layer Structure OLEDs having p-doped hole-transport layers have the following structure: substrate/hole-injection layer (HTL1, 20 nm)/hole-transport layer (HIL3, 140 nm for devices having a blue singlet emitter or 190 nm for devices having a green or yellow triplet emitter)/hole-transport layer (HTL according to the invention, doped with NPD-9 (3%) from Novaled, 20 nm)/hole-transport layer (HTL according to the invention, 20 nm)/emission layer (EML, 20 nm or 40 nm, see tables)/hole-blocking layer (HBL, in the case of blue triplet devices, 10 nm, see tables) electron-transport layer (ETL, 30 nm)/optional electron-injection layer (EIL) and finally a cathode. The cathode is formed by an aluminium layer with a thickness of 100 nm. The precise structure of the OLEDs and the results are shown in Tables 5 to 8. The materials required for the production of the OLEDs are shown in Table 12.

TABLE 5

Structure of the OLEDs

| Ex. | HTL 3% NDP-9 20 nm | HTL 20 nm | EML 20 nm | ETL 30 nm |
|---|---|---|---|---|
| D16 | Ex. 7 | Ex. 7 | H1(95%):SEB1(5%) | ETM1(50%):LiQ(50%) |
| D17 | Ex. 8 | Ex. 8 | H1(95%):SEB1(5%) | ETM1(50%):LiQ(50%) |
| D18 | Ex. 9 | Ex. 9 | H1(95%):SEB1(5%) | ETM1(50%):LiQ(50%) |
| D19 | Ex. 10 | Ex. 10 | H1(95%):SEB1(5%) | ETM1(50%):LiQ(50%) |
| D20 | Ex. 17 | Ex. 17 | H1(95%):SEB1(5%) | ETM1(50%):LiQ(50%) |
| D21 | Ex. 18 | Ex. 18 | H1(95%):SEB1(5%) | ETM1(50%):LiQ(50%) |
| D22 | Ex. 24 | Ex. 25 | H1(95%):SEB1(5%) | ETM1(50%):LiQ(50%) |
| D23 | Ex. 25 | Ex. 25 | H1(95%):SEB1(5%) | ETM1(50%):LiQ(50%) |
| D24 | Ex. 52 | Ex. 52 | H1(95%):SEB1(5%) | ETM1(50%):LiQ(50%) |
| D25 | Ex. 53 | Ex. 53 | H1(95%):SEB1(5%) | ETM1(50%):LiQ(50%) |
| D26 | Ex. 54 | Ex. 54 | H1(95%):SEB1(5%) | ETM1(50%):LiQ(50%) |
| D27 | Ex. 55 | Ex. 55 | H1(95%):SEB1(5%) | ETM1(50%):LiQ(50%) |
| D28 | Ex. 58 | Ex. 58 | H1(95%):SEB1(5%) | ETM1(50%):LiQ(50%) |
| D29 | Ex. 59 | Ex. 59 | H1(95%):SEB1(5%) | ETM1(50%):LiQ(50%) |
| D30 | Ex. 66 | Ex. 66 | H1(95%):SEB1(5%) | ETM1(50%):LiQ(50%) |
| D31 | Ex. 67 | Ex. 67 | H1(95%):SEB1(5%) | ETM1(50%):LiQ(50%) |
| D32 | Ex. 68 | Ex. 68 | H1(95%):SEB1(5%) | ETM1(50%):LiQ(50%) |
| D33 | Ex. 69 | Ex. 69 | H1(95%):SEB1(5%) | ETM1(50%):LiQ(50%) |
| D34 | Ex. 71 | Ex. 71 | H1(95%):SEB1(5%) | ETM1(50%):LiQ(50%) |
| D35 | Ex. 72 | Ex. 72 | H1(95%):SEB1(5%) | ETM1(50%):LiQ(50%) |
| D36 | Ex. 73 | Ex. 73 | H1(95%):SEB1(5%) | ETM1(50%):LiQ(50%) |
| D37 | Ex. 74 | Ex. 74 | H1(95%):SEB1(5%) | ETM1(50%):LiQ(50%) |

TABLE 5-continued

Structure of the OLEDs

| Ex. | HTL 3% NDP-9 20 nm | HTL 20 nm | EML 20 nm | ETL 30 nm |
|---|---|---|---|---|
| D38 | Ex. 77 | Ex. 77 | H1(95%):SEB1(5%) | ETM1(50%):LiQ(50%) |
| D39 | Ex. 86 | Ex. 86 | H1(95%):SEB1(5%) | ETM1(50%):LiQ(50%) |
| D40 | Ex. 87 | Ex. 87 | H1(95%):SEB1(5%) | ETM1(50%):LiQ(50%) |
| D41 | Ex. 88 | Ex. 88 | H1(95%):SEB1(5%) | ETM1(50%):LiQ(50%) |
| D42 | Ex. 89 | Ex. 89 | H1(95%):SEB1(5%) | ETM1(50%):LiQ(50%) |
| D43 | Ex. 90 | Ex. 90 | H1(95%):SEB1(5%) | ETM1(50%):LiQ(50%) |
| D45 | Ex. 91 | Ex. 81 | H1(95%):SEB1(5%) | ETM1(50%):LiQ(50%) |
| D46 | Ex. 92 | Ex. 92 | H1(95%):SEB1(5%) | ETM1(50%):LiQ(50%) |
| D47 | Ex. 93 | Ex. 93 | H1(95%):SEB1(5%) | ETM1(50%):LiQ(50%) |
| D48 | Ex. 94 | Ex. 94 | H1(95%):SEB1(5%) | ETM1(50%):LiQ(50%) |
| D49 | Ex. 95 | Ex. 95 | H1(95%):SEB1(5%) | ETM1(50%):LiQ(50%) |
| D50 | Ex. 96 | Ex. 96 | H1(95%):SEB1(5%) | ETM1(50%):LiQ(50%) |
| D51 | Ex. 69 | Ex. 69 | H1(95%):Ex. 101(5%) | ETM1(50%):LiQ(50%) |
| D52 | Ex. 69 | Ex. 69 | H1(95%):Ex. 102(5%) | ETM1(50%):LiQ(50%) |
| D53 | Ex. 72 | Ex. 72 | H1(95%):Ex. 103(5%) | ETM1(50%):LiQ(50%) |
| D54 | Ex. 88 | Ex. 88 | H1(95%):Ex. 104(5%) | ETM1(50%):LiQ(50%) |
| D55 | Ex. 69 | Ex. 69 | H1(95%):Ex. 105(5%) | ETM1(50%):LiQ(50%) |
| D56 | Ex. 90 | Ex. 90 | H1(95%):Ex. 106(5%) | ETM1(50%):LiQ(50%) |
| D57 | Ex. 69 | Ex. 69 | H1(95%):Ex. 107(5%) | ETM1(50%):LiQ(50%) |
| D58 | Ex. 90 | Ex. 90 | H1(95%):Ex. 120(5%) | ETM1(50%):LiQ(50%) |
| D59 | Ex. 90 | Ex. 90 | H1(95%):Ex. 121(5%) | ETM1(50%):LiQ(50%) |
| D60 | Ex. 90 | Ex. 90 | H1(95%):Ex. 122(5%) | ETM1(50%):LiQ(50%) |
| D61 | Ex. 69 | Ex. 69 | H1(95%):Ex. 123(5%) | ETM1(50%):LiQ(50%) |
| D62 | Ex. 69 | Ex. 69 | H1(95%):Ex. 124(5%) | ETM1(50%):LiQ(50%) |
| D63 | Ex. 90 | Ex. 90 | H1(95%):Ex. 125(5%) | ETM1(50%):LiQ(50%) |
| D64 | Ex. 90 | Ex. 90 | H1(95%):Ex. 126(5%) | ETM1(50%):LiQ(50%) |

TABLE 6

Data of the OLEDs

| Ex. | U @ 1000 cd/m2 V | EQE @ 1000 cd/m2 % | LT80 @ 1000 cd/m² [h] | CIE x | CIE y |
|---|---|---|---|---|---|
| D16 | 3.9 | 8.2 | 3300 | 0.14 | 0.14 |
| D17 | 4.0 | 8.3 | 3200 | 0.14 | 0.14 |
| D18 | 3.8 | 8.4 | 3900 | 0.14 | 0.13 |
| D19 | 3.9 | 7.6 | 2700 | 0.14 | 0.14 |
| D20 | 4.0 | 8.0 | 4600 | 0.14 | 0.14 |
| D21 | 3.9 | 8.1 | 4400 | 0.14 | 0.15 |
| D22 | 3.9 | 8.0 | 3100 | 0.14 | 0.14 |
| D23 | 3.8 | 8.1 | 4500 | 0.14 | 0.14 |
| D24 | 3.9 | 7.4 | 4000 | 0.14 | 0.14 |
| D25 | 3.8 | 7.5 | 2000 | 0.14 | 0.16 |
| D26 | 4.2 | 7.8 | 3800 | 0.14 | 0.14 |
| D27 | 4.3 | 7.9 | 3400 | 0.14 | 0.14 |
| D28 | 3.8 | 7.4 | 4100 | 0.14 | 0.14 |
| D29 | 3.9 | 7.1 | 4300 | 0.14 | 0.14 |
| D30 | 4.0 | 8.2 | 4100 | 0.14 | 0.14 |
| D31 | 4.2 | 8.3 | 4200 | 0.14 | 0.14 |
| D32 | 4.4 | 7.7 | 3600 | 0.14 | 0.14 |
| D33 | 3.9 | 7.6 | 4200 | 0.14 | 0.14 |
| D34 | 4.0 | 7.0 | 2200 | 0.14 | 0.14 |
| D35 | 3.9 | 7.5 | 4200 | 0.14 | 0.14 |
| D36 | 3.8 | 7.7 | 4100 | 0.14 | 0.14 |
| D37 | 3.8 | 7.8 | 4000 | 0.14 | 0.14 |
| D38 | 4.0 | 7.8 | 4500 | 0.14 | 0.14 |
| D39 | 3.9 | 7.8 | 4200 | 0.14 | 0.14 |
| D40 | 3.8 | 8.1 | 4400 | 0.14 | 0.13 |
| D41 | 4.1 | 8.3 | 4600 | 0.14 | 0.14 |
| D42 | 3.8 | 8.1 | 4900 | 0.14 | 0.13 |
| D43 | 3.9 | 8.0 | 5100 | 0.14 | 0.14 |
| D45 | 4.0 | 7.8 | 3900 | 0.14 | 0.14 |
| D46 | 4.0 | 7.9 | 3700 | 0.14 | 0.14 |
| D47 | 4.0 | 7.6 | 3000 | 0.14 | 0.14 |
| D48 | 3.9 | 8.2 | 4700 | 0.14 | 0.14 |
| D49 | 3.9 | 8.0 | 4000 | 0.14 | 0.14 |
| D50 | 4.2 | 8.0 | 4100 | 0.14 | 0.14 |
| D51 | 4.0 | 5.3 | 6100 | 0.17 | 0.33 |
| D52 | 3.9 | 6.7 | 1600 | 0.14 | 0.11 |
| D53 | 3.9 | 8.0 | 4600 | 0.14 | 0.15 |
| D54 | 3.9 | 8.1 | 4000 | 0.14 | 0.15 |
| D55 | 3.9 | 8.3 | 3800 | 0.14 | 0.13 |
| D56 | 4.2 | 7.7 | 4700 | 0.14 | 0.16 |
| D57 | 3.9 | 8.0 | 3900 | 0.14 | 0.13 |
| D58 | 4.2 | 8.1 | 3900 | 0.14 | 0.13 |
| D59 | 4.3 | 7.8 | 3900 | 0.14 | 0.13 |
| D60 | 4.2 | 8.4 | 4400 | 0.14 | 0.15 |
| D61 | 3.9 | 8.1 | 3700 | 0.14 | 0.14 |
| D62 | 3.9 | 8.0 | 4600 | 0.14 | 0.14 |
| D63 | 4.2 | 7.7 | 4000 | 0.15 | 0.17 |
| D64 | 4.3 | 8.0 | 3400 | 0.14 | 0.12 |

TABLE 7

Structure of the OLEDs

| Ex. | HTL 3% NDP-9 20 nm | HTL 20 nm | EML HBL 40 nm | ETL 30 nm |
|---|---|---|---|---|
| D65 | Ex. 7 | Ex. 7 | H3(50%):H4(45%):Irpy(5%) | ETM1(50%):LiQ(50%) |
| D66 | Ex. 8 | Ex. 8 | H3(50%):H4(45%):Irpy(5%) | ETM1(50%):LiQ(50%) |
| D67 | Ex. 16 | Ex. 16 | H3(50%):H4(45%):Irpy(5%) | ETM1(50%):LiQ(50%) |
| D68 | Ex. 17 | Ex. 17 | H2(90%):Irpy(10%) | ETM1(50%):LiQ(50%) |
| D69 | Ex. 18 | Ex. 18 | H3(50%):H4(45%):Irpy(5%) | ETM1(50%):LiQ(50%) |
| D70 | Ex. 54 | Ex. 54 | H3(50%):H4(45%):Irpy(5%) | ETM1(50%):LiQ(50%) |
| D71 | Ex. 64 | Ex. 64 | H3(50%):H4(45%):Irpy(5%) | ETM1(50%):LiQ(50%) |
| D72 | Ex. 66 | Ex. 66 | H3(50%):H4(45%):Irpy(5%) | ETM1(50%):LiQ(50%) |
| D73 | Ex. 67 | Ex. 67 | H3(50%):H4(45%):Irpy(5%) | ETM1(50%):LiQ(50%) |
| D74 | Ex. 69 | Ex. 69 | H3(50%):H4(45%):Irpy(5%) | ETM1(50%):LiQ(50%) |
| D75 | Ex. 70 | Ex. 70 | H3(50%):H4(45%):Irpy(5%) | ETM1(50%):LiQ(50%) |
| D76 | Ex. 72 | Ex. 72 | H3(50%):H4(45%):Irpy(5%) | ETM1(50%):LiQ(50%) |
| D77 | Ex. 73 | Ex. 73 | H3(50%):H4(45%):Irpy(5%) | ETM1(50%):LiQ(50%) |
| D78 | Ex. 78 | Ex. 78 | H3(50%):H4(45%):Irpy(5%) | ETM1(50%):LiQ(50%) |
| D79 | Ex. 86 | Ex. 86 | H3(50%):H4(45%):Irpy(5%) | ETM1(50%):LiQ(50%) |
| D80 | Ex. 87 | Ex. 87 | H3(50%):H4(45%):Irpy(5%) | ETM1(50%):LiQ(50%) |
| D81 | Ex. 88 | Ex. 88 | H3(50%):H4(45%):Irpy(5%) | ETM1(50%):LiQ(50%) |
| D82 | Ex. 89 | Ex. 89 | H3(50%):H4(45%):Irpy(5%) | ETM1(50%):LiQ(50%) |
| D83 | Ex. 90 | Ex. 90 | H3(50%):H4(45%):Irpy(5%) | ETM1(50%):LiQ(50%) |
| D84 | Ex. 91 | Ex. 91 | H3(50%):H4(45%):Irpy(5%) | ETM1(50%):LiQ(50%) |
| D85 | Ex. 96 | Ex. 96 | H3(50%):H4(45%):Irpy(5%) | ETM1(50%):LiQ(50%) |
| D86 | Ex. 59 | Ex. 59 | H3(45%):H4(45%):Irppy(10%) | ETM1(50%):LiQ(50%) |
| D87 | Ex. 86 | Ex. 86 | H3(45%):H4(45%):Irppy(10%) | ETM1(50%):LiQ(50%) |
| D88 | Ex. 87 | Ex. 87 | H3(45%):H4(45%):Irppy(10%) | ETM1(50%):LiQ(50%) |
| D89 | Ex. 88 | Ex. 88 | H3(45%):H4(45%):Irppy(10%) | ETM1(50%):LiQ(50%) |
| D90 | Ex. 89 | Ex. 89 | H3(45%):H4(45%):Irppy(10%) | ETM1(50%):LiQ(50%) |
| D91 | Ex. 90 | Ex. 90 | H3(45%):H4(45%):Irppy(10%) | ETM1(50%):LiQ(50%) |
| D92 | Ex. 30 | Ex. 30 | H5(30%):H6(65%):Irbic(10%) HBL | ETM1(50%):LiQ(50%) |
| D93 | Ex. 36 | Ex. 36 | H5(30%):H6(65%):Irbic(10%) HBL | ETM1(50%):LiQ(500%) |
| D94 | Ex. 37 | Ex. 37 | H5(30%):H6(65%):Irbic(10%) HBL | ETM1(50%):LiQ(50%) |
| D95 | Ex. 52 | Ex. 52 | H5(30%):H6(65%):Irbic(10%) HBL | ETM1(50%):LiQ(50%) |
| D96 | Ex. 55 | Ex. 55 | H5(30%):H6(65%):Irbic(10%) HBL | ETM1(50%):LiQ(50%) |
| D97 | Ex. 56 | Ex. 56 | H5(30%):H6(65%):Irbic(10%) HBL | ETM1(50%):LiQ(50%) |
| D98 | Ex. 57 | Ex. 57 | H5(30%):H6(65%):Irbic(10%) HBL | ETM1(50%):LiQ(50%) |
| D99 | Ex. 94 | Ex. 94 | H5(30%):H6(65%):Irbic(10%) HBL | ETM1(50%):LiQ(50%) |
| D100 | Ex. 95 | Ex. 95 | H5(30%):H6(65%):Irbic(10%) HBL | ETM1(50%):LiQ(50%) |
| D101 | Ex. 96 | Ex. 96 | H5(30%):H6(65%):Irbic(10%) HBL | ETM1(5G %):LiQ(50%) |
| D102 | Ex. 69 | Ex. 69 | Ex. 80(50%):H4(45%):Irpy(5%) | ETM1(50%):LiQ(50%) |
| D103 | Ex. 69 | Ex. 69 | Ex. 81(50%):H4(45%):Irpy(5%) | ETM1(50%):LiQ(50%) |
| D104 | Ex. 69 | Ex. 69 | Ex. 82(50%):H4(45%):Irpy(5%) | ETM1(50%):LiQ(50%) |
| D105 | Ex. 69 | Ex. 69 | Ex. 83(50%):H4(45%):Irpy(5%) | ETM1(50%):LiQ(50%) |
| D106 | Ex. 69 | Ex. 69 | Ex. 84(90%) Irpy(10%) | ETM1(50%):LiQ(50%) |
| D107 | Ex. 69 | Ex. 69 | Ex. 85(50%):H4(45%):Irpy(5%) | ETM1(50%):LiQ(50%) |
| D108 | Ex. 69 | Ex. 69 | Ex. 111(10%):Irpy(10%) | ETM1(50%):LiQ(50%) |
| D109 | Ex. 69 | Ex. 69 | Ex. 112(50%):H4(45%):Irpy(5%) | ETM1(50%):LiQ(50%) |
| D110 | Ex. 69 | Ex. 69 | Ex. 113(50%):H4(45%):Irpy(5%) | ETM1(50%):LiQ(50%) |
| D111 | Ex. 69 | Ex. 69 | Ex. 114(50%):H4(45%):Irpy(5%) | ETM1(50%):LiQ(50%) |
| D112 | Ex. 57 | Ex. 57 | Ex. 65(10%):Irbic(10%) HBL | ETM1(50%):LiQ(50%) |
| D113 | Ex. 57 | Ex. 57 | Ex. 85(10%):Irbic(10%) HBL | ETM1(50%):LiQ(50%) |
| D114 | Ex. 57 | Ex. 57 | H5(30%):Ex97(65%):Irbic(5%) HBL | ETM1(50%):LiQ(50%) |
| D115 | Ex. 57 | Ex. 57 | Ex. 113(30%):Ex. 97(65%):Irbic(5%) Ex. 113 | ETM1(50%):LiQ(50%) |
| D116 | Ex. 57 | Ex. 57 | Ex. 115(10%):Irbic(10%) HBL | ETM1(50%):LiQ(50%) |
| D117 | Ex. 57 | Ex. 57 | Ex. 116(10%):Irbic(10%) HBL | ETM1(50%):LIQ(50%) |

TABLE 7-continued

Structure of the OLEDs

| Ex. | HTL 3% NDP-9 20 nm | HTL 20 nm | EML HBL 40 nm 10 nm | ETL 30 nm |
|---|---|---|---|---|
| D118 | Ex. 57 | Ex. 57 | Ex. 117(10%):Irbic(10%) HBL | ETM1(50%):LiQ(50%) |
| D119 | Ex. 57 | Ex. 57 | Ex. 119(10%):Irbic(10%) HBL | ETM1(50%):LiQ(50%) |

TABLE 8

Data of the OLEDs

| Ex. | U @ 1000 cd/m$^2$ V | EQE @ 1000 cd/m$^2$ % | LT80 @ 1000 cd/m$^2$ [h] | CIE x | CIE y |
|---|---|---|---|---|---|
| D65 | 3.1 | 20.3 | 16000 | 0.35 | 0.62 |
| D66 | 3.3 | 20.4 | 17000 | 0.35 | 0.62 |
| D67 | 3.1 | 19.5 | 60000 | 0.33 | 0.63 |
| D68 | 3.0 | 20.0 | 2300 | 0.36 | 0.61 |
| D69 | 3.1 | 19.4 | 54000 | 0.33 | 0.63 |
| D70 | 3.2 | 19.8 | 58000 | 0.33 | 0.64 |
| D71 | 3.2 | 18.8 | 41000 | 0.33 | 0.64 |
| D72 | 3.1 | 19.3 | 48000 | 0.33 | 0.63 |
| D73 | 3.3 | 19.7 | 51000 | 0.34 | 0.63 |
| D74 | 3.0 | 20.4 | 61000 | 0.34 | 0.63 |
| D75 | 3.1 | 19.7 | 63000 | 0.34 | 0.63 |
| D76 | 3.0 | 20.5 | 59000 | 0.34 | 0.63 |
| D77 | 3.0 | 20.1 | 60000 | 0.34 | 0.63 |
| D78 | 3.0 | 18.4 | 33000 | 0.34 | 0.65 |
| D79 | 3.1 | 19.7 | 62000 | 0.34 | 0.63 |
| D80 | 3.0 | 20.7 | 66000 | 0.34 | 0.63 |
| D81 | 3.2 | 21.1 | 65000 | 0.33 | 0.63 |
| D82 | 3.0 | 21.3 | 67000 | 0.34 | 0.63 |
| D83 | 3.2 | 20.8 | 66000 | 0.33 | 0.63 |
| D84 | 3.0 | 21.4 | 62000 | 0.34 | 0.63 |
| D85 | 3.0 | 21.0 | 58000 | 0.34 | 0.63 |
| D86 | 3.0 | 23.5 | 46000 | 0.44 | 0.55 |
| D87 | 2.9 | 23.6 | 60000 | 0.43 | 0.55 |
| D88 | 2.9 | 23.5 | 61000 | 0.44 | 0.55 |
| D89 | 3.1 | 24.0 | 58000 | 0.44 | 0.55 |
| D90 | 2.9 | 23.7 | 67000 | 0.44 | 0.55 |
| D91 | 3.2 | 23.9 | 65000 | 0.43 | 0.55 |
| D92 | 4.7 | 13.4 | 180 | 0.15 | 0.30 |
| D93 | 4.8 | 13.6 | 160 | 0.15 | 0.30 |
| D94 | 4.6 | 12.9 | 150 | 0.15 | 0.30 |
| D95 | 4.7 | 13.1 | 180 | 0.15 | 0.31 |
| D96 | 4.7 | 13.2 | 210 | 0.15 | 0.30 |
| D97 | 4.8 | 13.3 | 200 | 0.15 | 0.29 |
| D98 | 4.8 | 13.4 | 230 | 0.15 | 0.30 |
| D99 | 4.7 | 12.8 | 220 | 0.15 | 0.30 |
| D100 | 5.0 | 13.6 | 200 | 0.15 | 0.30 |
| D101 | 4.8 | 13.7 | 200 | 0.15 | 0.30 |
| D102 | 3.0 | 22.4 | 66000 | 0.34 | 0.63 |
| D103 | 2.9 | 22.0 | 65000 | 0.34 | 0.63 |
| D104 | 3.0 | 21.9 | 68000 | 0.34 | 0.64 |
| D105 | 2.9 | 22.2 | 69000 | 0.34 | 0.63 |
| D106 | 3.3 | 21.5 | 48000 | 0.34 | 0.63 |
| D107 | 2.9 | 22.5 | 63000 | 0.34 | 0.63 |
| D108 | 3.3 | 21.9 | 45000 | 0.34 | 0.63 |
| D109 | 2.9 | 21.5 | 60000 | 0.34 | 0.63 |
| D110 | 2.9 | 22.2 | 64000 | 0.35 | 0.63 |
| D111 | 3.1 | 22.1 | 62000 | 0.34 | 0.63 |
| D112 | 4.8 | 13.0 | 200 | 0.15 | 0.30 |
| D113 | 5.2 | 13.9 | 170 | 0.15 | 0.29 |
| D114 | 4.5 | 13.6 | 230 | 0.15 | 0.30 |
| D115 | 4.6 | 13.8 | 210 | 0.15 | 0.29 |
| D116 | 4.5 | 13.6 | 180 | 0.15 | 0.30 |
| D117 | 4.5 | 13.4 | 150 | 0.15 | 0.30 |
| D118 | 4.5 | 13.7 | 200 | 0.15 | 0.30 |
| D119 | 4.8 | 13.4 | 160 | 0.15 | 0.30 |

Use of the Compounds According to the Invention in White OLEDs

A white-emitting OLED having the following layer structure is produced by the general processes: substrate/hole-injection layer (HIL1, 20 nm)/hole-transport layer (HIL3, 40 nm)/hole-transport layer (HTL according to the invention, doped with NPD-9 (3%) from Novaled, 20 nm)/hole-transport layer (HTL according to the invention, 200 nm)/emission layers (EML, see table)/hole-blocking layer (HBL, 10 nm, see table) electron-transport layer (ETL, 30 nm)/optional electron-injection layer (EIL) and finally a cathode. The cathode is formed by an aluminium layer with a thickness of 100 nm. The precise structure of the OLEDs and the results are shown in Tables 9 and 10. The materials required for the production of the OLEDs are shown in Table 12.

TABLE 9

Structure of the white OLEDs

| Ex. | HTL Thickness | EML Red Thickness | EML Blue Thickness | EML Green Thickness | HBL Thickness | ETL Thickness |
|---|---|---|---|---|---|---|
| D-W1 | Ex. 88 200 nm | Ex. 88.Ir-R (97%:3%) 9 nm | H6:HBL:Irbic$_3$ (45%:50%:5%) 8 nm | Ex. 110:Irpy (90%:10%) 7 nm | HBL 10 nm | ETM1(50%):LiQ(50%) 30 nm |

TABLE 10

| | Device results | | | |
|---|---|---|---|---|
| Ex. | EQE (%) 1000 cd/m$^2$ | Voltage (V) 1000 cd/m$^2$ | CIE x/y 1000 cd/m$^2$ CRI | LT50 (h) 1000 cd/m$^2$ |
| D-W1 | 14.1 | 6.3 | 0.45/0.43 80 | 2500 |

Use of the Compounds According to the Invention OLEDs Processed from Solution

The compounds according to the invention can also be processed from solution, where they result in OLEDs which are significantly simpler in processing terms, compared with the vacuum-processed OLEDs, with nevertheless good properties. The production of components of this type is based on the production of polymeric light-emitting diodes (PLEDs), which has already been described many times in the literature (for example in WO 2004/037887).

The structure is composed of substrate/ITO/PEDOT (80 nm)/interlayer (80 nm)/emission layer (80 nm)/cathode. To this end, substrates from Technoprint (soda-lime glass) are used, to which the ITO structure (indium tin oxide, a transparent, conductive anode) is applied. The substrates are cleaned in a clean room with DI water and a detergent (Deconex 15 PF) and then activated by a UV/ozone plasma treatment. An 80 nm layer of PEDOT (PEDOT is a polythiophene derivative (Baytron P VAI 4083sp.) from H. C. Starck, Goslar, which is supplied as aqueous dispersion) is then applied as buffer layer by spin coating, likewise in the clean room. The spin rate required depends on the degree of dilution and the specific spin-coater geometry (typically for 80 nm: 4500 rpm). In order to remove residual water from the layer, the substrates are dried by heating at 180° C. on a hotplate for 10 minutes. The interlayer used serves for hole injection, in this case HIL-012 from Merck is used. The interlayer may alternatively also be replaced by one or more layers, which merely have to satisfy the condition of not being detached again by the subsequent processing step of EML deposition from solution. In order to produce the emission layer, the emitters according to the invention are dissolved in toluene together with the matrix materials. The typical solids content of such solutions is between 16 and 25 g/l if, as here, the typical layer thickness of 80 nm for a device is to be achieved by means of spin coating. The solution-processed devices comprise an emission layer (EML) comprising (polystyrene): Ex.:H7:IrL (D-L1-D-L6) or (polystyrene): Ex.:Ex.:IrL (D-L7) (15%:25%:50%:10%). The emission layer is applied by spin coating in an inert-gas atmosphere, in the present case argon, and dried by heating at 130° C. for 30 min. Finally, a cathode comprising barium (5 nm) and then aluminium (100 nm) (high-purity metals from Aldrich, particularly barium 99.99% (Order No. 474711); vapour-deposition units from Lesker or others, typical vapour-deposition pressure 5×10$^{-6}$ mbar) is applied by vapour deposition. Firstly a hole-blocking layer and then an electron-transport layer and only then the cathode (for example Al or LiF/Al) can optionally be applied by vacuum vapour deposition. In order to protect the device against air and atmospheric moisture, the device is finally encapsulated and then characterised. The OLED examples given have not yet been optimised, Table 11 summarises the data obtained.

TABLE 11

| | | Data of the OLEDs | | | | |
|---|---|---|---|---|---|---|
| Ex. | EML Ex. | U @ 1000 cd/m2 V | EQE @ 1000 cd/m2 % | LT80 @ 1000 cd/m$^2$ [h] | CIE x | CIE y |
| D-L1 | 75 | 3.6 | 17.9 | 16000 | 0.32 | 0.63 |
| D-L2 | 76 | 3.8 | 18.2 | 18000 | 0.33 | 0.63 |
| D-L3 | 79 | 3.7 | 18.0 | 17000 | 0.32 | 0.64 |
| D-L4 | 98 | 3.7 | 16.4 | 19000 | 0.32 | 0.64 |
| D-L5 | 99 | 3.8 | 19.2 | 20000 | 0.33 | 0.63 |
| D-L6 | 10 | 4.0 | 19.7 | 24000 | 0.33 | 0.63 |
| D-L7 | 100 + 118 | 3.7 | 17.2 | 14000 | 0.33 | 0.63 |

TABLE 12

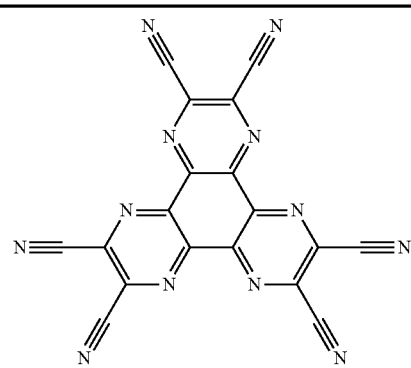

HIL1

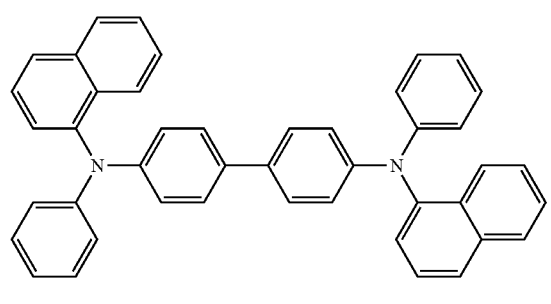 [SMILES: c1ccc(N(c2ccc(-c3ccc(N(c4ccccc4)c4cccc5ccccc45)cc3)cc2)c2cccc3ccccc23)cc1]

NPB

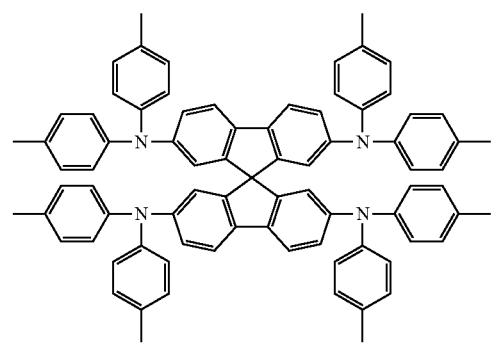

HIL2

TABLE 12-continued
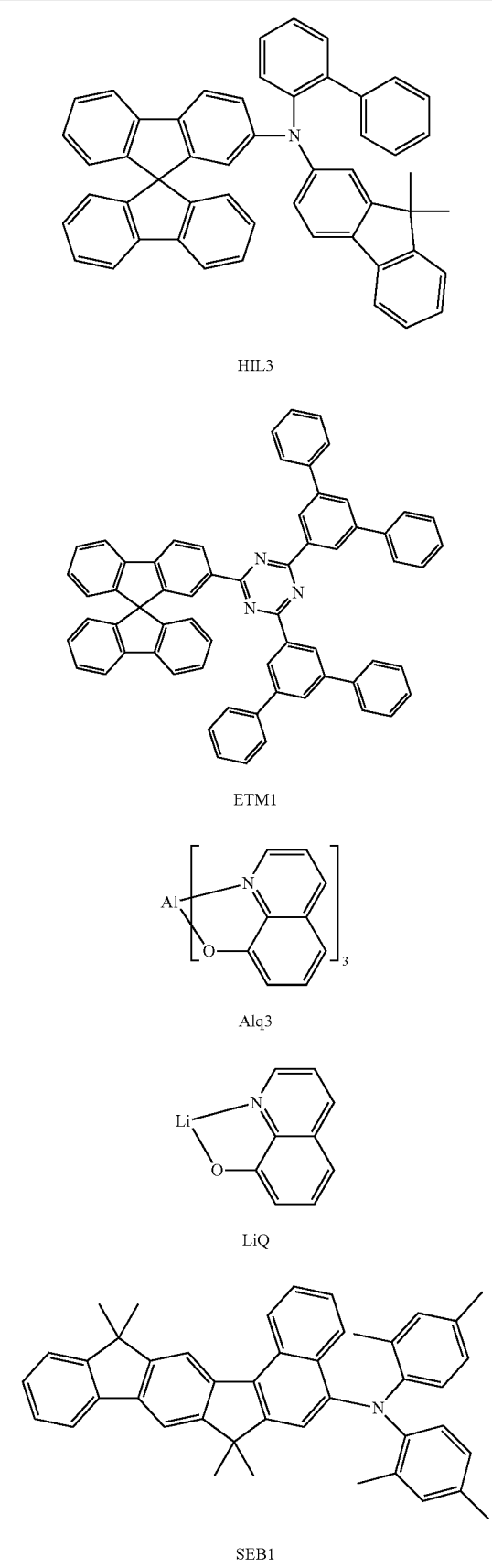
HIL3
ETM1
Alq3
LiQ
SEB1
TABLE 12-continued
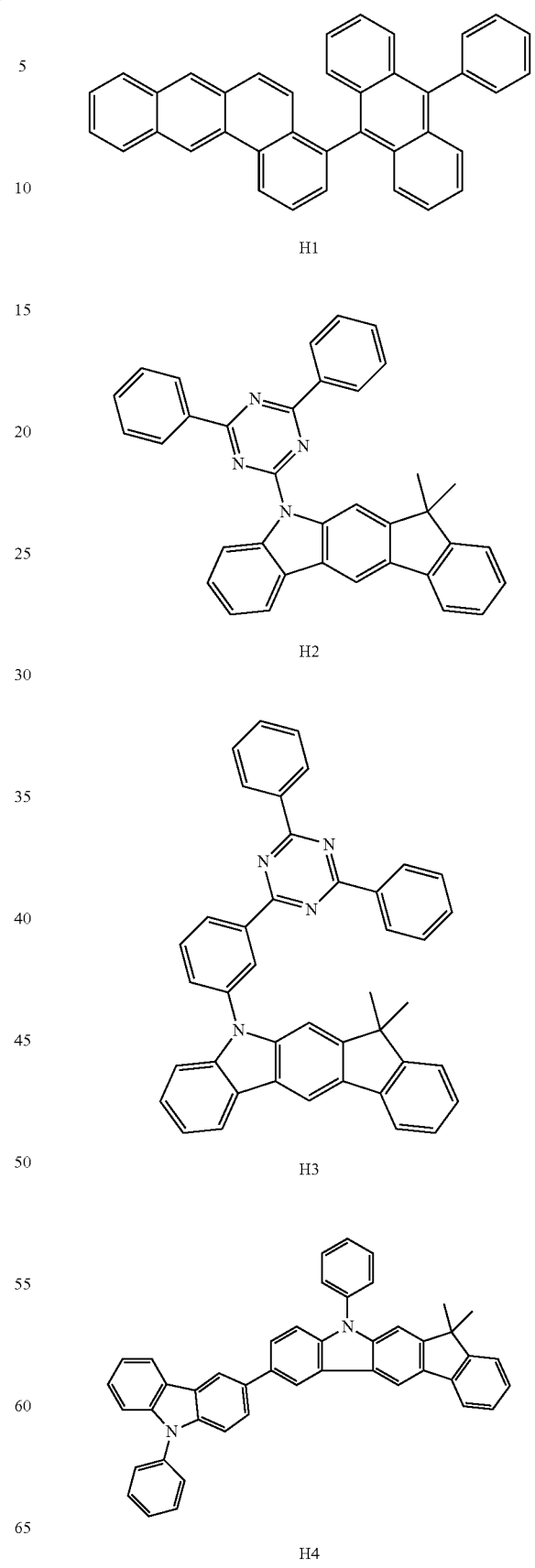
H1
H2
H3
H4

TABLE 12-continued
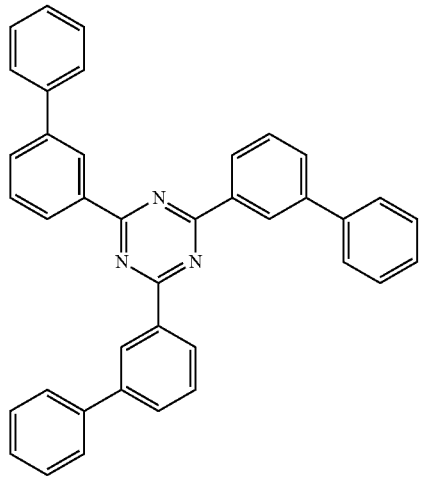 [SMILES: c1ccc(-c2cccc(-c3nc(-c4cccc(-c5ccccc5)c4)nc(-c4cccc(-c5ccccc5)c4)n3)c2)cc1]
H5
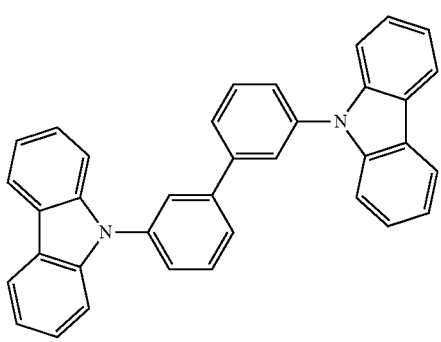 [SMILES: c1cc(-c2cccc(-n3c4ccccc4c4ccccc43)c2)cc(-n2c3ccccc3c3ccccc32)c1]
H6
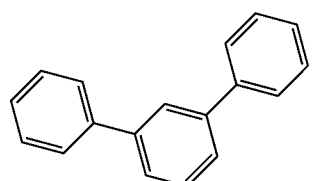
H7
TABLE 12-continued
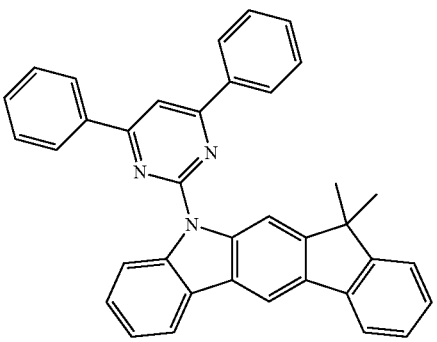 [SMILES: CC1(C)c2ccccc2-c2cc3c4ccccc4n(-c4nc(-c5ccccc5)cc(-c5ccccc5)n4)c3cc21]
HBL
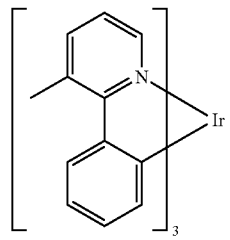
Irpy
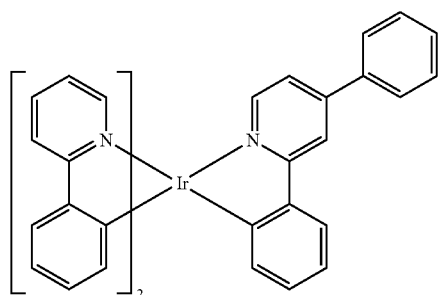
Irppy
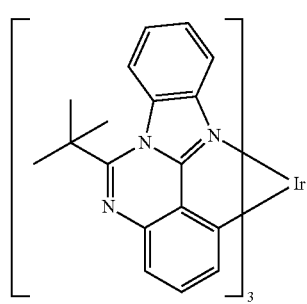
Irbic TABLE 12-continued

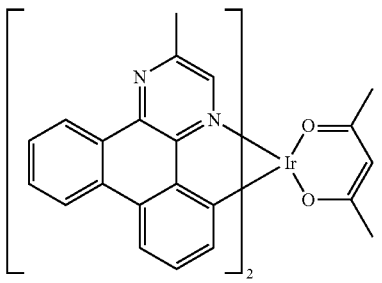

IrR

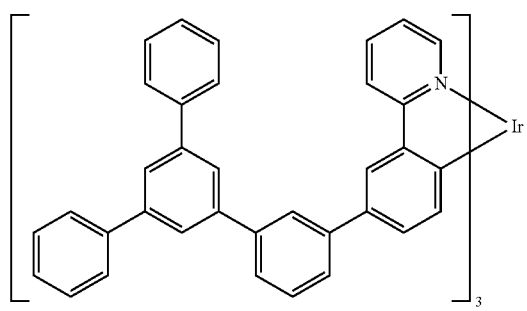

IrL

The invention claimed is:

1. A compound of the formula (1), (2) or (3)

formula (1)

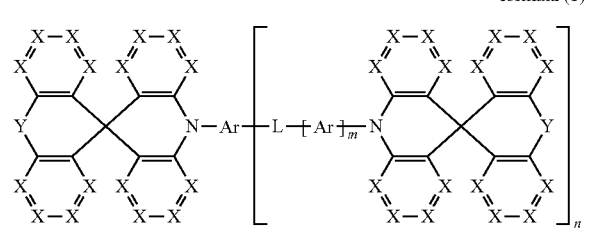

formula (2)

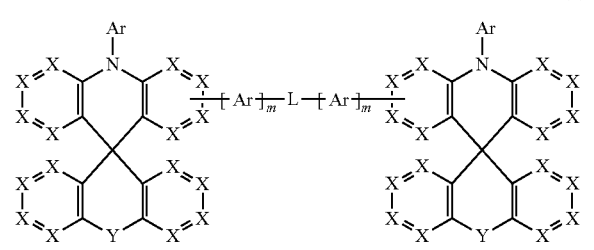

formula (3)

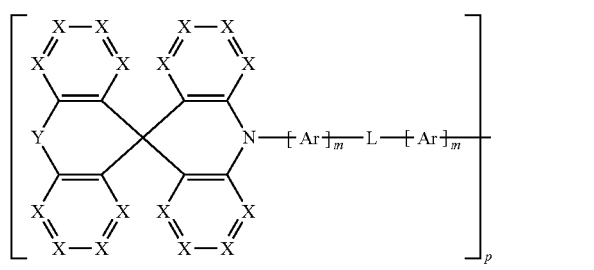

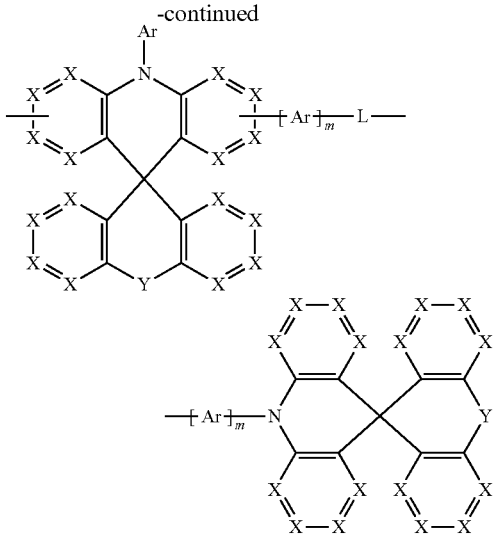

where the following applies to the symbols and indices used:

Y is O;

X is on each occurrence, identically or differently, $CR^2$

Ar is on each occurrence, identically or differently, an aromatic or heteroaromatic ring system having 5 to 40 aromatic ring atoms, which is optionally substituted by one or more radicals $R^3$; the group Ar and the adjacent group X, which in this case stands for C, may also be bridged to one another here by a single bond or a divalent group selected from $C(R^3)_2$, $NR^3$, O or S;

L is on each occurrence, identically or differently, a single bond or a divalent group;

$R^2$, $R^3$ is selected on each occurrence, identically or differently, from the group consisting of H, D, F, Cl, Br, I, CN, $NO_2$, $N(Ar^1)_2$, $N(R^4)_2$, $C(=O)Ar^1$, $C(=O)R^4$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^4$, where one or more non-adjacent $CH_2$ groups is optionally replaced by $R^4C=CR^4$, $Si(R^4)_2$, C=O, C=S, C=$NR^4$, $P(=O)(R^4)$, SO, $SO_2$, $NR^4$, O, S or $CONR^4$ and where one or more H atoms is optionally replaced by D, F, Cl, Br, I, CN or $NO_2$, an aromatic or heteroaromatic ring system having 5 to 60, aromatic ring atoms, which may in each case be substituted by one or more radicals $R^4$, an aryloxy or heteroaryloxy group having 5 to 60 aromatic ring atoms, which is optionally substituted by one or more radicals $R^4$, where two or more adjacent substituents $R^1$ or $R^3$ may optionally form a monocyclic or polycyclic, aliphatic ring system or $R^2$ may form a monocyclic or polycyclic, aliphatic, aromatic or heteroaromatic ring system, which is optionally substituted by one or more radicals $R^4$;

wherein at least one of the radicals $R^2$ is selected from aromatic ring systems having 6 to 24 aromatic ring atoms and said aromatic ring systems do not contain any heteroatoms;

$R^4$ is selected on each occurrence, identically or differently, from the group consisting of H, D, F, Cl, Br, I, CN, $NO_2$, $N(Ar^1)_2$, $N(R^5)_2$, $C(=O)Ar^1$, $C(=O)R^5$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^5$, where one or more non-adjacent $CH_2$ groups is optionally replaced by $R^5C$=$CR^5$, C≡C, $Si(R^5)_2$, C=O, C=S, C=$NR^5$, P(=O)($R^5$), SO, $SO_2$, $NR^5$, O, S or $CONR^5$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^5$, an aryloxy or heteroaryloxy group having 5 to 60 aromatic ring atoms, which is optionally substituted by one or more radicals $R^5$, or a combination of these systems, where two or more adjacent substituents $R^4$ may optionally form a monocyclic or polycyclic, aliphatic ring system, which is optionally substituted by one or more radicals $R^5$;

$Ar^1$ is on each occurrence, identically or differently, an aromatic or heteroaromatic ring system having 5-30 aromatic ring atoms, which is optionally substituted by one or more non-aromatic radicals $R^5$; two radicals $Ar^1$ which are bonded to the same N atom or P atom may also be bridged to one another here by a single bond or a bridge selected from $N(R^5)$, $C(R^5)_2$, O or S;

$R^5$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^3$ may form a mono- or polycyclic, aliphatic ring system with one another;

m is on each occurrence, identically or differently, 0 or 1;

n is 0;

p is 0 or 1.

2. The compound according to claim 1, wherein $R^2$, $R^3$ is selected on each occurrence, identically or differently, from the group consisting of H, D, F, Cl, Br, I, CN, $NO_2$, $N(Ar^1)_2$, $N(R^4)_2$, C(=O)$Ar^1$, C(=O)$R^4$, P(=O)($Ar^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^4$, where one or more non-adjacent $CH_2$ groups is optionally replaced by $R^4C$=$CR^4$, C≡C, $Si(R^4)_2$, C=O, C=S, C=$NR^4$, P(=O)($R^4$), SO, $SO_2$, $NR^4$, O, S or $CONR^4$ and where one or more H atoms is optionally replaced by D, F, Cl, Br, I, CN or $NO_2$, an aromatic or heteroaromatic ring system having 5 to 60, aromatic ring atoms, which may in each case be substituted by one or more radicals $R^4$, an aryloxy or heteroaryloxy group having 5 to 60 aromatic ring atoms, which is optionally substituted by one or more radicals $R^4$;

$R^4$ is selected on each occurrence, identically or differently, from the group consisting of H, D, F, Cl, Br, I, CN, $NO_2$, $N(Ar^1)_2$, $N(R^5)_2$, C(=O)$Ar^1$, C(=O)$R^5$, P(=O)($Ar^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^5$, where one or more non-adjacent $CH_2$ groups is optionally replaced by $R^5C$=$CR^5$, C≡C, $Si(R^5)_2$, C=O, C=S, C=$NR^5$, P(=O)($R^5$), SO, $SO_2$, $NR^5$, O, S or $CONR^5$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^5$, an aryloxy or heteroaryloxy group having 5 to 60 aromatic ring atoms, which is optionally substituted by one or more radicals $R^5$;

$R^5$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN.

3. The compound according to claim 1, wherein L stands, identically or differently on each occurrence, for a straight-chain alkylene, alkylidene, alkyleneoxy or thioalkyleneoxy group having 1 to 10 C atoms or a branched or cyclic alkylene, alkylidene, alkyleneoxy or thioalkyleneoxy group having 3 to 40 C atoms or an alkenylene or alkynylene group having 2 to 40 C atoms, which is optionally substituted by in each case one or more radicals $R^4$, where one or more non-adjacent $CH_2$ groups is optionally replaced by —$R^4C$=$CR^4$—, —C≡C—, $Si(R^4)_2$, C=O, C=$NR^4$, P(=O)$R^4$, S=O, $SO_2$, —O—, —S— or —$CONR^4$— and where one or more H atoms is optionally replaced by D, F, Cl, Br, I, CN or $NO_2$, or P($R^4$), P(=O)($R^4$), $N(Ar^1)$; or L is a single bond.

4. The compound according to claim 1, selected from the compounds of the formulae (6) to (12), formula (6)

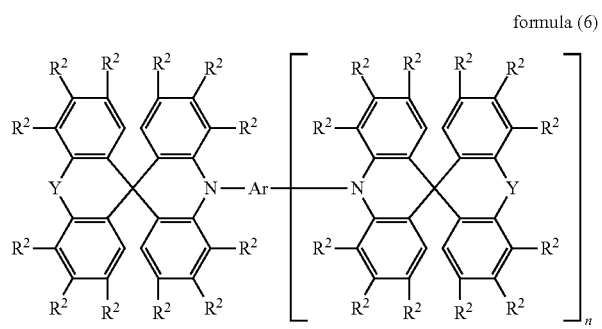

formula (7)

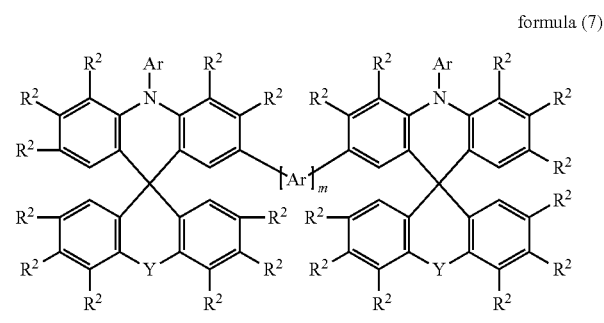

formula (8)
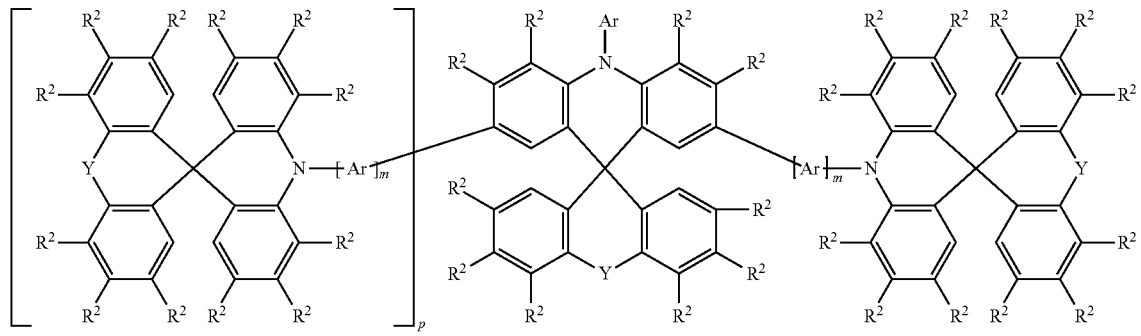
formula (9)
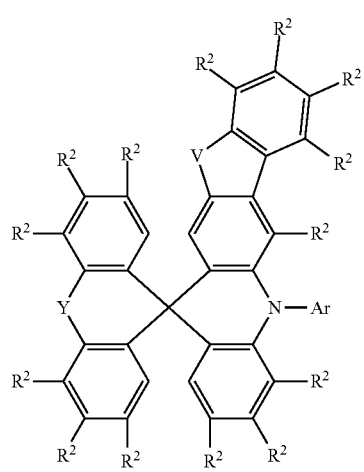
formula (10)
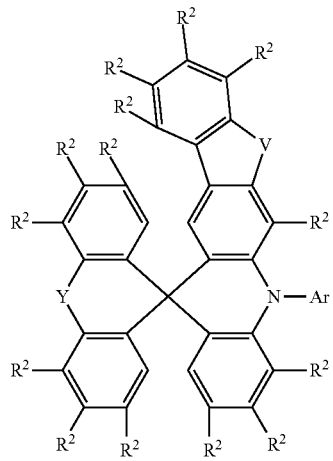
formula (11)
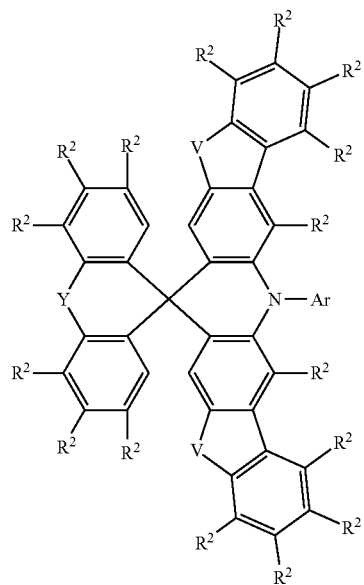
formula (12)
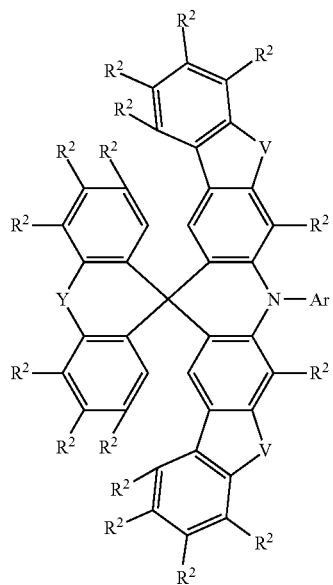
where the symbols and indices used have the meanings given in claim 1.
5. The compound according to claim 1, selected from the compounds of the formulae (6a) to (12a), formula (6a)
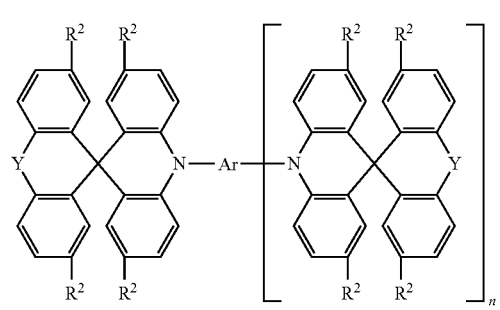
formula (7a)
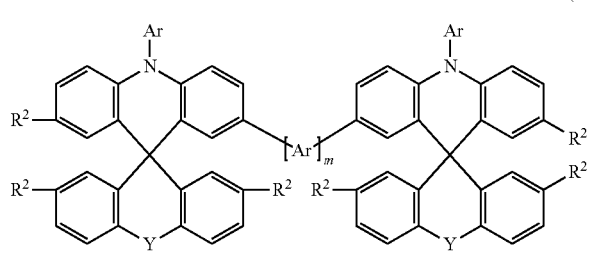
formula (8a)
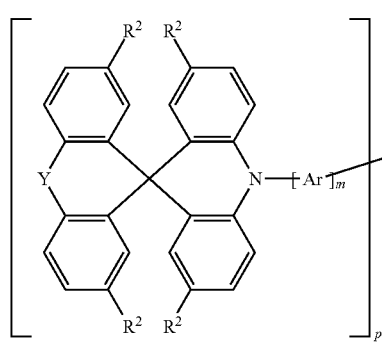
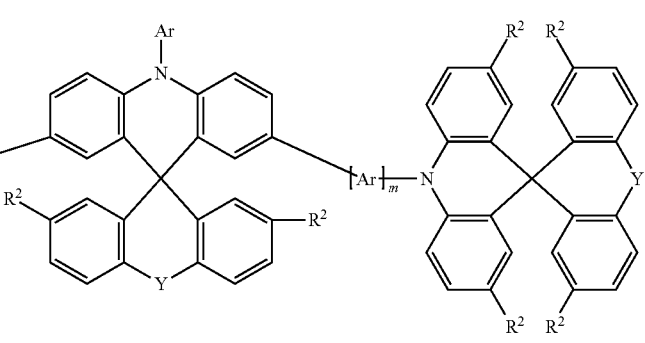
formula (9a)
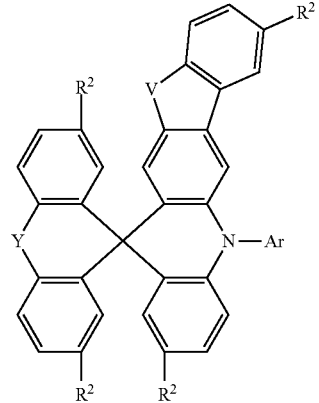
formula (10a)
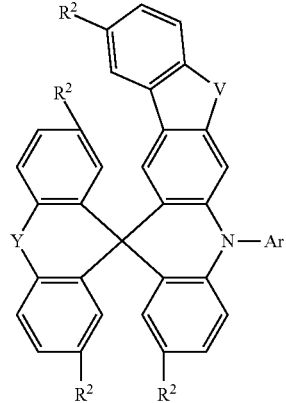
formula (11a)
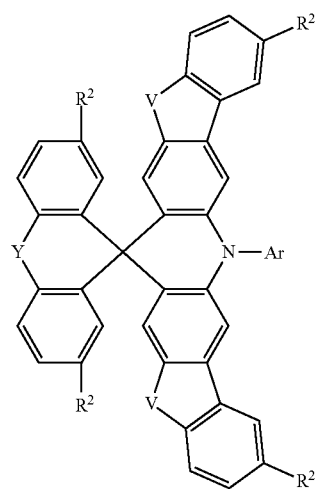
formula (12a)
where the symbols and indices used have the meanings given in claim 1.
6. The compound according to claim 5, wherein Ar is selected from the group consisting of benzene, ortho-, metaor para-biphenyl, ortho-, meta-, para- or branched terphenyl, ortho-, meta- para- or branched quaterphenyl, 1- or 2-naphthyl, pyrrole, furan, thiophene, indole, benzothiophene, benzofuran, carbazole, dibenzofuran, dibenzothiophene, pyridine, pyrimidine, pyrazine, pyridazine, triazine, anthracene, phenanthrene, pyrene, benzanthracene or combinations of two or three of these groups, each of which is optionally substituted by one or more radicals R³.

7. The compound according to claim 1, wherein Ar is selected from the group consisting of aromatic or heteroaromatic ring systems having 5 to 24 aromatic ring atoms, which may in each case be substituted by one or more radicals R³.

8. The compound according to claim 1, wherein Ar is selected from the group consisting of benzene, ortho-, meta- or para-biphenyl, ortho-, meta-, para- or branched terphenyl, ortho-, meta- para- or branched quaterphenyl, 1- or 2-naphthyl, pyrrole, furan, thiophene, indole, benzothiophene, benzofuran, carbazole, dibenzofuran, dibenzothiophene, pyridine, pyrimidine, pyrazine, pyridazine, triazine, anthracene, phenanthrene, pyrene, benzanthracene or combinations of two or three of these groups, each of which is optionally substituted by one or more radicals R³.

9. The compound according to claim 1, wherein at least one substituent R² and/or R³ or a monovalent group Ar is selected from structures of the formulae (13) to (16) for R¹ to R³ or the formulae (13), (15) or (16) for Ar,

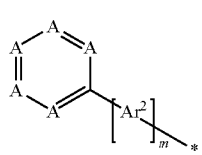

formula (13)

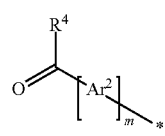

formula (14)

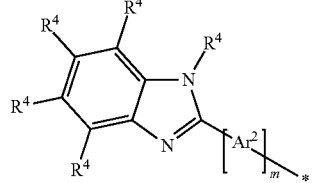

formula (15)

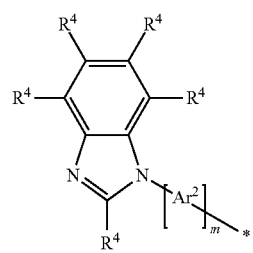

formula (16)

and/or at least one divalent or trivalent group Ar is selected from the groups of the formulae (17) to (19),

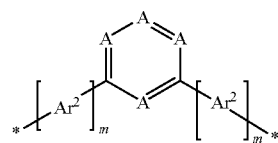

formula (17)

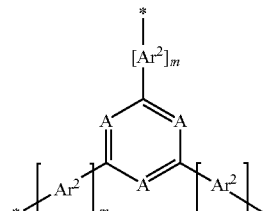

formula (18)

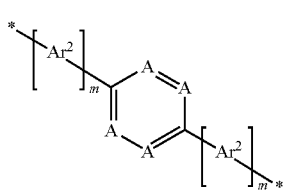

formula (19)

where R³, R⁴ and m have the meaning given in claim 1, * indicates the position of the bonding of the group of the formula (13) to (19) and furthermore:

A is on each occurrence, identically or differently, CR⁴ or N, with the proviso that one group A, two groups A or three groups A stand for N;

Ar² is, identically or differently on each occurrence, a divalent aromatic or heteroaromatic ring system having 5 to 16 C atoms, which is optionally substituted by one or more radicals R⁴;

and/or in that at least one of the radicals R¹, R², R³ or Ar is selected from the groups of the formulae (20) to (26), and/or at least one of the radicals Ar is selected from groups of the formulae (27) to (34),

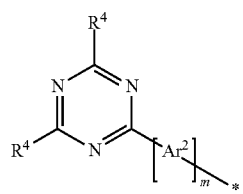

formula (20)

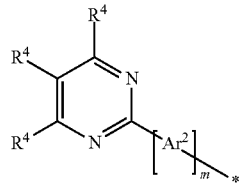

formula (21)

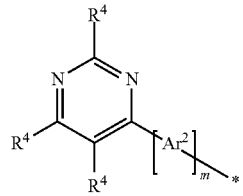

formula (22)

-continued
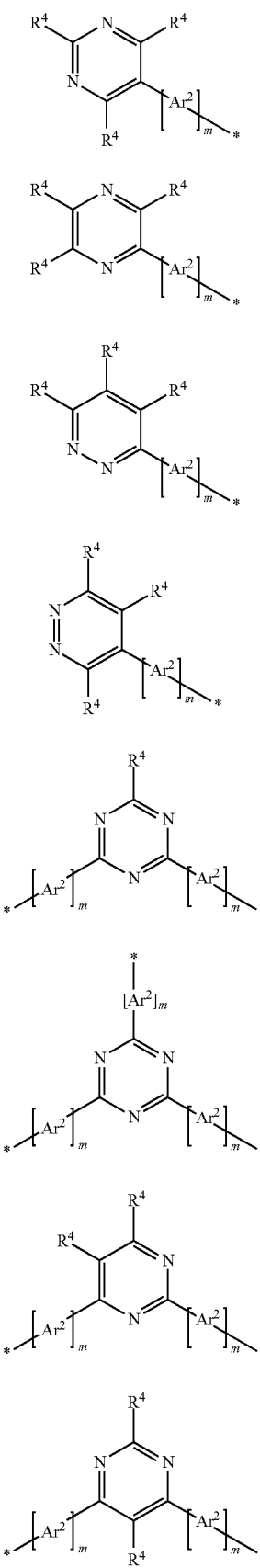
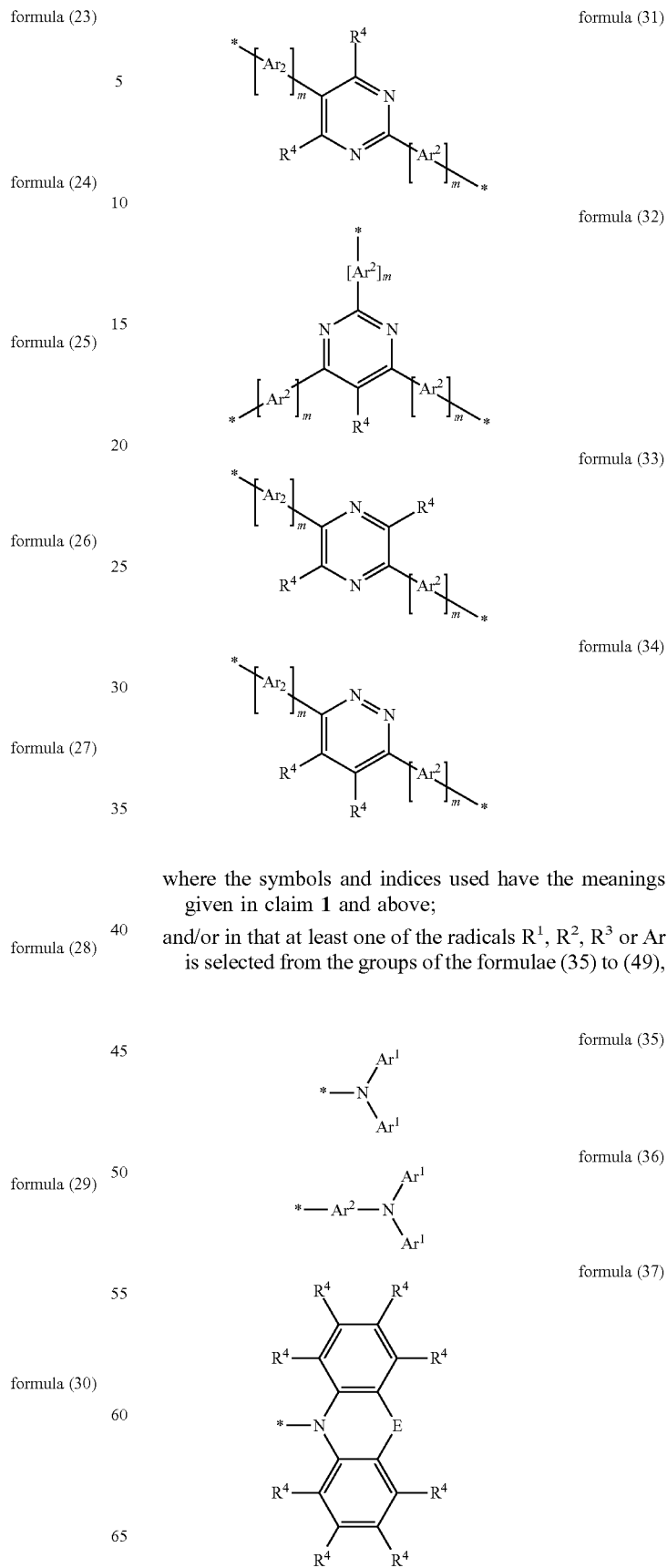
where the symbols and indices used have the meanings given in claim 1 and above;
and/or in that at least one of the radicals $R^1$, $R^2$, $R^3$ or Ar is selected from the groups of the formulae (35) to (49),

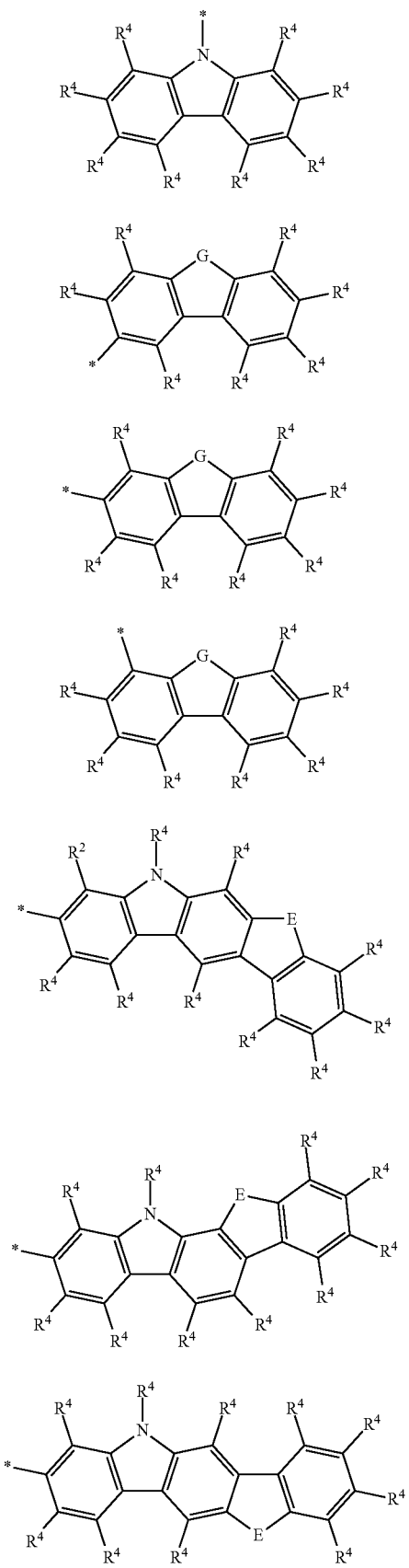
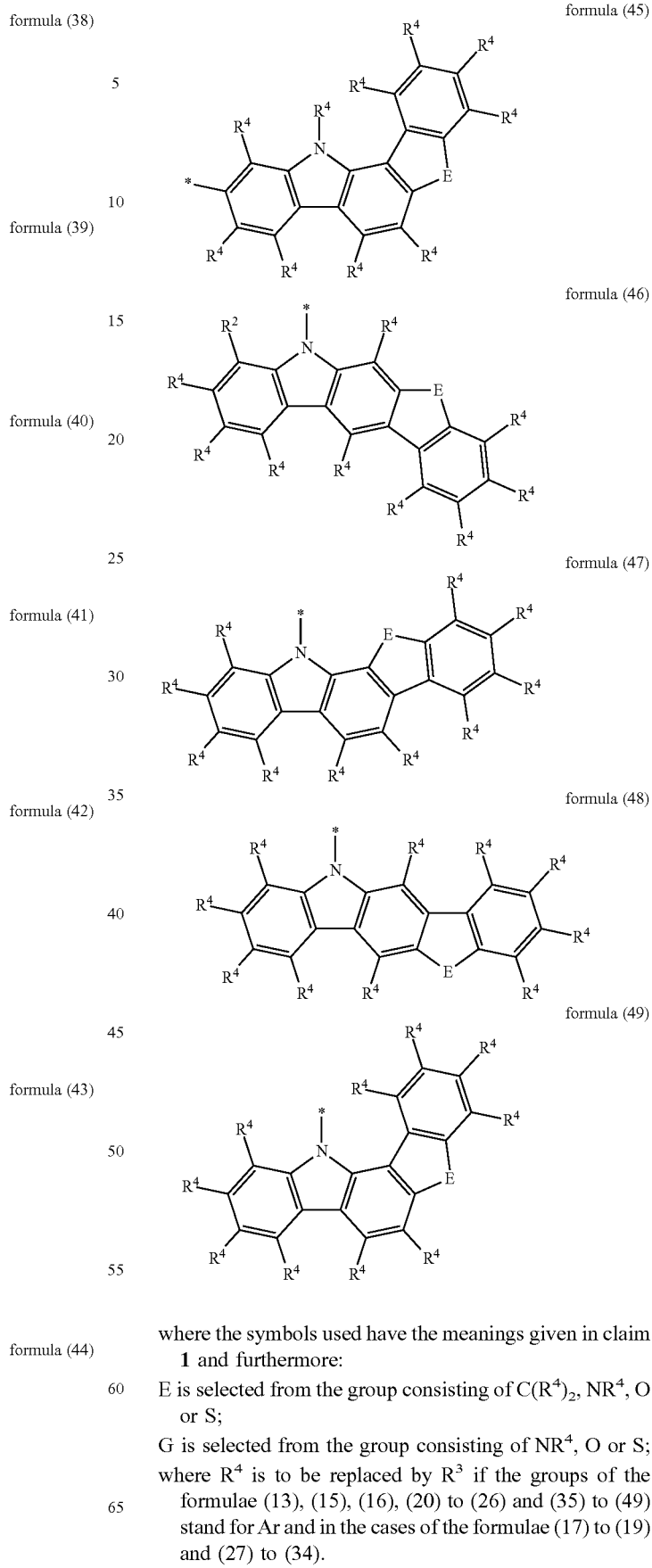
where the symbols used have the meanings given in claim 1 and furthermore:
E is selected from the group consisting of $C(R^4)_2$, $NR^4$, O or S;
G is selected from the group consisting of $NR^4$, O or S;
where $R^4$ is to be replaced by $R^3$ if the groups of the formulae (13), (15), (16), (20) to (26) and (35) to (49) stand for Ar and in the cases of the formulae (17) to (19) and (27) to (34).

10. A process for the preparation of the compound according to claim 1, comprising the reaction steps:
   a) building-up the halogenated skeleton; and
   b) introducing substituents via a transition-metal-catalysed coupling reaction.

11. An oligomer, polymer or dendrimer containing one or more compounds according to claim 1, where one or more bonds are present from the compound to the polymer, oligomer or dendrimer.

12. An electronic device which comprises the compound according to claim 1.

13. The electronic device as claimed in claim 12, wherein the device is selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

14. An organic electroluminescent device in which the compound according to claim 1 is employed as matrix material for fluorescent or phosphorescent emitters and/or as fluorescent emitter and/or in an electron-blocking or exciton-blocking layer and/or in a hole-transport layer and/or in a hole-blocking layer and/or in an electron-transport layer and/or in an optical coupling-out layer.

15. A compound of the formula (2) or (3)

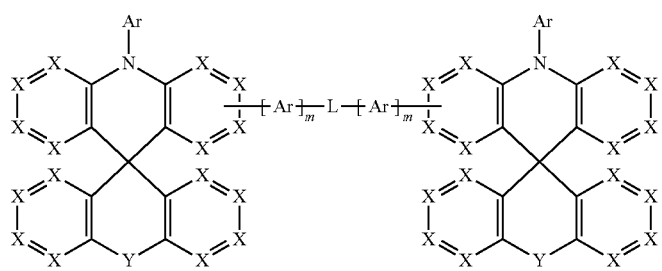

formula (2)

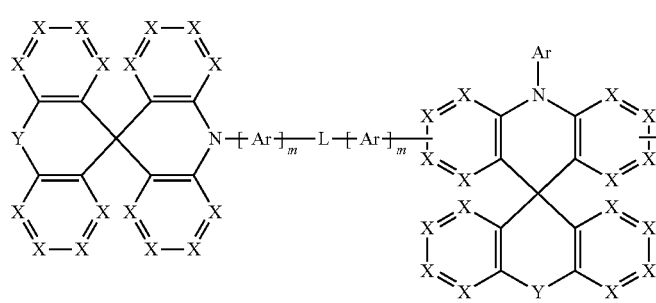

formula (3)

where the following applies to the symbols and indices used:

Y is on each occurrence, identically or differently, O or S;

X is on each occurrence, identically or differently, $CR^2$ or N; or two adjacent X stand for S, O or $NR^2$, so that a five-membered ring arises; or two adjacent X stand for a group of the following formula (4) or (5),

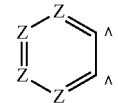

formula (4)

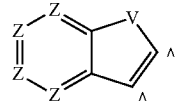

formula (5)

where ^ indicates the corresponding adjacent groups X in the formula (1), (2) or (3);

X here stands for C if a group Ar or L is bonded to this group X in formula (2) or (3);

V is on each occurrence, identically or differently, $C(R^2)_2$, $NR^2$, O or S;

Z is on each occurrence, identically or differently, $CR^2$ or N;

Ar is on each occurrence, identically or differently, an aromatic or heteroaromatic ring system having 5 to 40 aromatic ring atoms, which is optionally substituted by one or more radicals $R^3$; the group Ar and the adjacent group X, which in this case stands for C, may also be bridged to one another here by a single bond or a divalent group selected from $C(R^3)_2$, $NR^3$, O or S;

L is on each occurrence, identically or differently, a single bond or a divalent group;

$R^2$, $R^3$ is selected on each occurrence, identically or differently, from the group consisting of H, D, F, Cl, Br, I, CN, $NO_2$, $N(Ar^1)_2$, $N(R^4)_2$, $C(=O)Ar^1$, $C(=O)R^4$, $P(=O)(Ar^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^4$, where one or more non-adjacent $CH_2$ groups is optionally replaced by $R^4C=CR^4$, C≡C, $Si(R^4)_2$, C=O, C=S, C=$NR^4$, P(=O)($R^4$), SO, $SO_2$, $NR^4$, O, S or $CONR^4$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^4$, an aryloxy or heteroaryloxy group having 5 to 60 aromatic ring atoms, which is optionally substituted by one or more radicals $R^4$, where two or more adjacent substituents $R^1$ or $R^3$ may optionally form a monocyclic or polycyclic, aliphatic ring system or $R^2$ may form a monocyclic or polycyclic, aliphatic, aromatic or heteroaromatic ring system, which is optionally substituted by one or more radicals $R^4$;

wherein at least one of the radicals $R^2$ is selected from aromatic ring systems having 6 to 24 aromatic ring atoms and said aromatic ring systems do not contain any heteroatoms;

$R^4$ is selected on each occurrence, identically or differently, from the group consisting of H, D, F, Cl, Br, I, CN, $NO_2$, N($Ar^1$)$_2$, N($R^5$)$_2$, C(=O)$Ar^1$, C(=O)$R^5$, P(=O)($Ar^1$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^5$, where one or more non-adjacent $CH_2$ groups is optionally replaced by $R^5C$=$CR^5$, $Si(R^5)_2$, C=O, C=S, C=$NR^5$, P(=O)($R^5$), SO, $SO_2$, $NR^5$, O, S or $CONR^5$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^5$, an aryloxy or heteroaryloxy group having 5 to 60 aromatic ring atoms, which is optionally substituted by one or more radicals $R^5$, or a combination of these systems, where two or more adjacent substituents $R^4$ may optionally form a monocyclic or polycyclic, aliphatic ring system, which is optionally substituted by one or more radicals $R^5$;

$Ar^1$ is on each occurrence, identically or differently, an aromatic or heteroaromatic ring system having 5-30 aromatic ring atoms, which is optionally substituted by one or more non-aromatic radicals $R^5$; two radicals $Ar^1$ which are bonded to the same N atom or P atom may also be bridged to one another here by a single bond or a bridge selected from N($R^5$), C($R^5$)$_2$, O or S;

$R^5$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^3$ may form a mono- or polycyclic, aliphatic ring system with one another;

m is on each occurrence, identically or differently, 0 or 1;

n is 0, 1, 2, 3, 4 or 5;

p is 0 or 1.

16. The compound according to claim 15, wherein Y is O.

17. The compound according to claim 15, wherein all groups Y are selected identically.

18. The compound according to claim 15, wherein X, identically or differently on each occurrence, stands for $CR^2$ or N, where a maximum of one group X per ring stands for N; or two adjacent groups X stand for a group of the formula (4) or (5), where Z stands, identically or differently on each occurrence, for $CR^2$ and V stands, identically or differently on each occurrence, for $NR^2$ or C($R^2$)$_2$.

* * * * *